(12) United States Patent
Shabat et al.

(10) Patent No.: US 9,341,630 B2
(45) Date of Patent: May 17, 2016

(54) ACTIVATABLE FLUOROGENIC COMPOUNDS AND USES THEREOF AS NEAR INFRARED PROBES

(71) Applicant: Ramot at Tel-Aviv University Ltd., Tel-Aviv (IL)

(72) Inventors: Doron Shabat, Tel-Aviv (IL); Ronit Satchi-Fainaro, Tel-Aviv (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 14/027,219

(22) Filed: Sep. 15, 2013

(65) Prior Publication Data

US 2014/0010763 A1 Jan. 9, 2014

Related U.S. Application Data

(63) Continuation-in-part of application No. PCT/IB2012/051255, filed on Mar. 15, 2012.

(60) Provisional application No. 61/452,684, filed on Mar. 15, 2011, provisional application No. 61/452,688, filed on Mar. 15, 2011, provisional application No. 61/556,335, filed on Nov. 7, 2011.

(51) Int. Cl.
| | |
|---|---|
| A61K 49/00 | (2006.01) |
| G01N 33/58 | (2006.01) |
| A61K 47/48 | (2006.01) |
| C09B 23/01 | (2006.01) |
| C09B 23/08 | (2006.01) |
| C09B 23/12 | (2006.01) |

(52) U.S. Cl.
CPC ........ *G01N 33/582* (2013.01); *A61K 47/48153* (2013.01); *A61K 49/0021* (2013.01); *A61K 49/0032* (2013.01); *A61K 49/0052* (2013.01); *A61K 49/0056* (2013.01); *C09B 23/0066* (2013.01); *C09B 23/086* (2013.01); *C09B 23/12* (2013.01)

(58) Field of Classification Search
CPC ....... A61K 49/00; A61K 49/0021; A61B 5/00
See application file for complete search history.

(56) References Cited

U.S. PATENT DOCUMENTS

| | | | |
|---|---|---|---|
| 6,110,630 A | 8/2000 | Reddy et al. | |
| 6,217,848 B1 | 4/2001 | Achilefu et al. | |
| 7,553,959 B2 | 6/2009 | Stavrianopoulos et al. | |
| 2009/0076278 A1 | 3/2009 | Dan-Oh et al. | |
| 2009/0124792 A1* | 5/2009 | Achilefu et al. | 530/391.3 |
| 2009/0148386 A1 | 6/2009 | Mao et al. | |
| 2010/0278739 A1 | 11/2010 | Bornhop et al. | |

FOREIGN PATENT DOCUMENTS

WO WO 2012/123916 9/2012

OTHER PUBLICATIONS

International Preliminary Report on Patentability Dated Sep. 26, 2013 From the International Bureau of WIPO Re. Application No. PCT/B2012/051255.
International Search Report and the Written Opinion Dated Jan. 30, 2013 From the International Searching Authority Re. Application No. PCT/IB2012/051255.
Avital-Shmilovici et al. "Dendritic Chain Reaction: Responsive Release of Hydrogen Peroxide Upon Generation and Enzymatic Oxidation of Methanol", Bioorganic & Medicinal Chemistry, 18(11): 3643-3647, Jun. 1, 2010.
Dickinson et al. "A Palette of Fluorescent Probes With Verying Emission Colors for Imaging Hydrogen Peroxide Signaling in Living Cells", Journal of the American Chemical Society, JACS, 132(16): 5906-5915, Apr. 28, 2010.
Dickinson et al. "NOX2 Redox Signaling Maintains Essential Cell Populations in the Brain", Nature Chemical Biology, 7(2): 106-112, Feb. 2011.
Ho et al. "Development of a Dual Fluorogenic and Chromogenic Dipeptidyl Peptidase IV Substrate", Bioorganic & Medicinal Chemistry Letters, 16: 2599-2602, 2006.
Huenig et al. "1-Alkoxy- und 1.3-Dialkoxy-Phenalenium-Ionen und ihre Reaktionen", Justus Liebigs Annalen der Chemie, XP055035622, 732: 7-25, Mar. 1, 1970. p. 15, Compounds 30, 33, p. 17, Compound 42.
Karton-Lifshin et al. "A Unique Paradigm for a Turn-On Near-Infrared Cyanine-Based Probe: Noninvasive Intravital Optical Imaging of Hydrogen Peroxide", Journal of the American Chemical Society, JACS, 133(28): 10960-10965, Jul. 20, 2011.
Karton-Lifshin et al. "Ultrafast Excited-State Intermolecular Proton Transfer of Cyanine Fluorochrome Dyes", The Journal of Physical Chemistry A, X0055036753, 116(1): 85-92, Jan. 12, 2012.
Katritzky et al. "Bridged Cyanine Dyes. Part 2 [1]. 1-(N-Methyl-2-Benzothiazolylinio)-3-(N-Methyl-2-Benzothiazolylene) and 1-(N-Methyl-4-Pyridinio)-3-(N-Methyl-4-Pyriylene)Cyclopenta-1,4-Dienes With Fused Rings", Journal of Heterocyclic Chemistry, XP055045242, 25(5): 1315-1319, Sep. 1, 1988. Scheme 1, p. 1315, Schemes 2, 3, p. 1317.

(Continued)

*Primary Examiner* — Michael G Hartley
*Assistant Examiner* — Jagadishwar Samala

(57) ABSTRACT

Novel fluorogenic compounds designed such that upon a chemical event, compounds capable of emitting NIR light are generated, are disclosed. The compounds comprise two or more acceptor-containing moieties and a cleavable donor-containing moiety, being in complete pi-electrons conjugation and being such that no delocalization of pi-electrons is enabled. Also disclosed are fluorescent compounds generated upon subjecting the fluorogenic compounds to a chemical event (e.g., deprotonation). Also disclosed are uses of the fluorogenic compounds as NIR probed with a Turn-ON mechanism in monitoring presence and/or level of various analytes.

24 Claims, 46 Drawing Sheets
(37 of 46 Drawing Sheet(s) Filed in Color)

(56) References Cited

OTHER PUBLICATIONS

Kundu et al. "A Significant Improvement of the Efficacy of Radical Oxidant Probes by the Kinetic Isotope Effect", Angewandte Chemie, International Edition, 49: 6134-6138, 2010.

Kundu et al. "Hydrocyanines: A Class of Fluorescent Sensors That Can Image Reactive Oxygen Species in Cell Culture, Tissue, and In Vivo", Angewnadte Chemie, International Edition, 48: 299-303, 2009.

Maity et al. "A Turn-On NIR Fluorescence and Colourimetric Cyanine Probe for Monitoring the Thiol Content in Serum and the Glutathione Reductase Assisted Glutathione Redox Process", Organic & Biomolecular Chemistry, 11(13): 2098-2104, Apr. 7, 2013.

Miller et al. "Molecular Imaging of Hydrogen Peroxide Produced for Cell Signaling", Nature Chemical Biology, 3(5): 263-267, May 2007.

Richard et al. "7-Hydroxycoumarin-Hemicyanine Hybrids: A New Class of Far-Red Emitting Fluorogenic Dyes", Organic Letters, 10(19): 4175-4178, 2008.

Samanta et al. "Development of Photostable Near-infrared Cyanine Dyes", Chemical Communications, 46(39): 7406-7408, Oct. 21, 2010.

Sella et al. "Dendritic Chain Reaction", Journal of the American Chemical Society, JACS, 131: 9934-9936, 2009.

Sella et al. "Self-Immolative Dendritic Probe for Direct Detection of Triacetone Tripcroxidc", Chcmical Communications, 44: 5701-5703, Nov. 30, 2008.

Sella et al. "Two-Component Dendritic Chain Reactions: Experiment and Theory", Journal of the American Chemical Society, JACS, 132: 3945-3952, 2010.

Shi et al. "A Novel Near-Infrared Fluorescent Probe for Selectively Sensing Nitroreductase (NTR) in an Aqueous Medium", Analyst, 138: 1952-1955, 2013.

Tung et al. "Preparation of a Cathepsin D Sensitive Near-Infrared Fluorescence Probe for Imaging", Bioconjugate Chemistry, 10: 892-896, 1999.

Van de Bittner et al. "In Vivo Imaging of Hydrogen Peroxide Production in a Murine Tumor Model With a Chemoselective Bioluminescent Reporter", Proc. Natl. Acad. Sci. USA, PNAS, 107(50): 21316-21321, Dec. 14, 2010.

Weinstain et al. "Real-Time Monotoring of Drug Release", Chemical Communications, 46: 553-555, 2010.

\* cited by examiner

Cy7

Acceptors

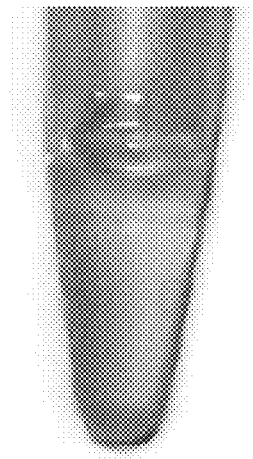 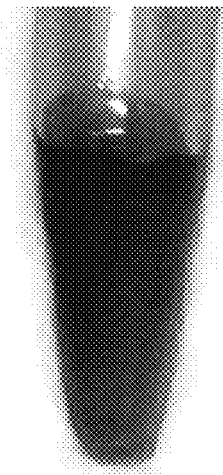
FIG. 19A
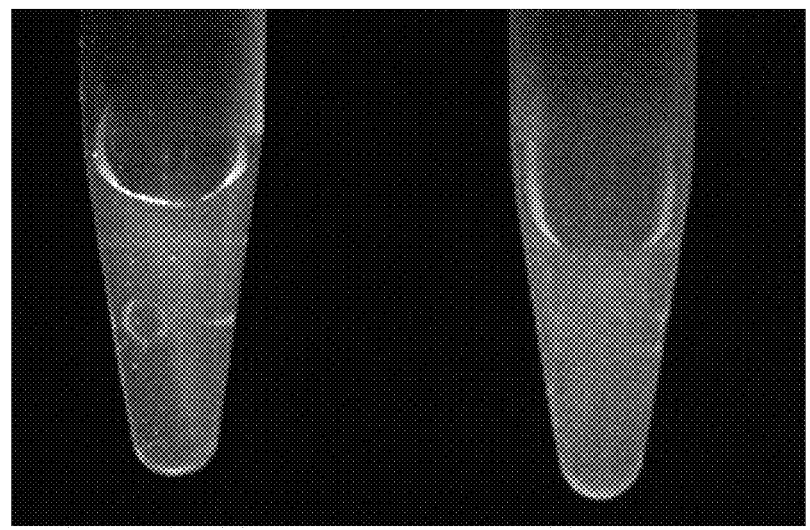
FIG. 19B

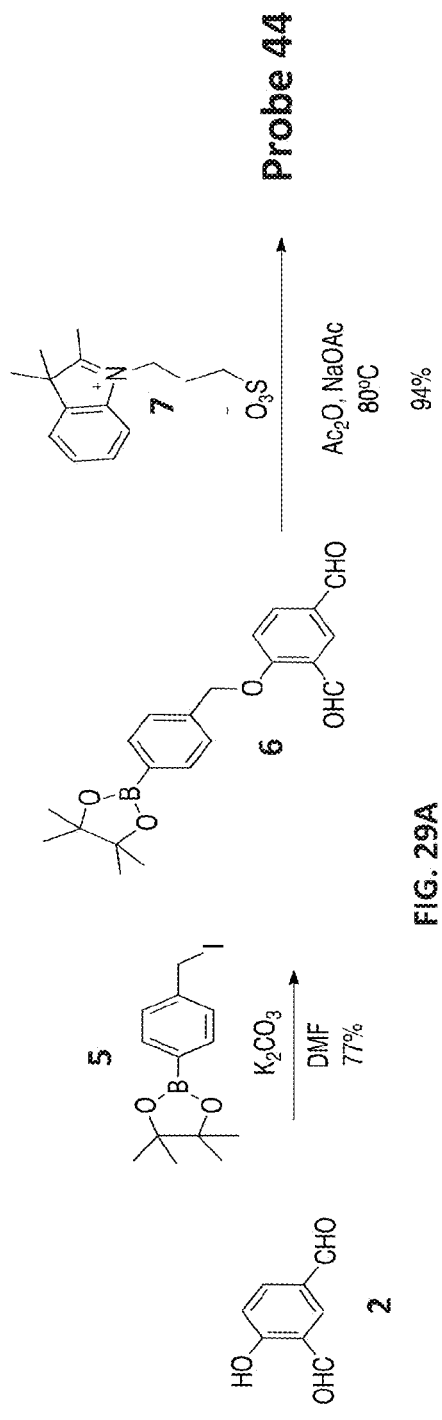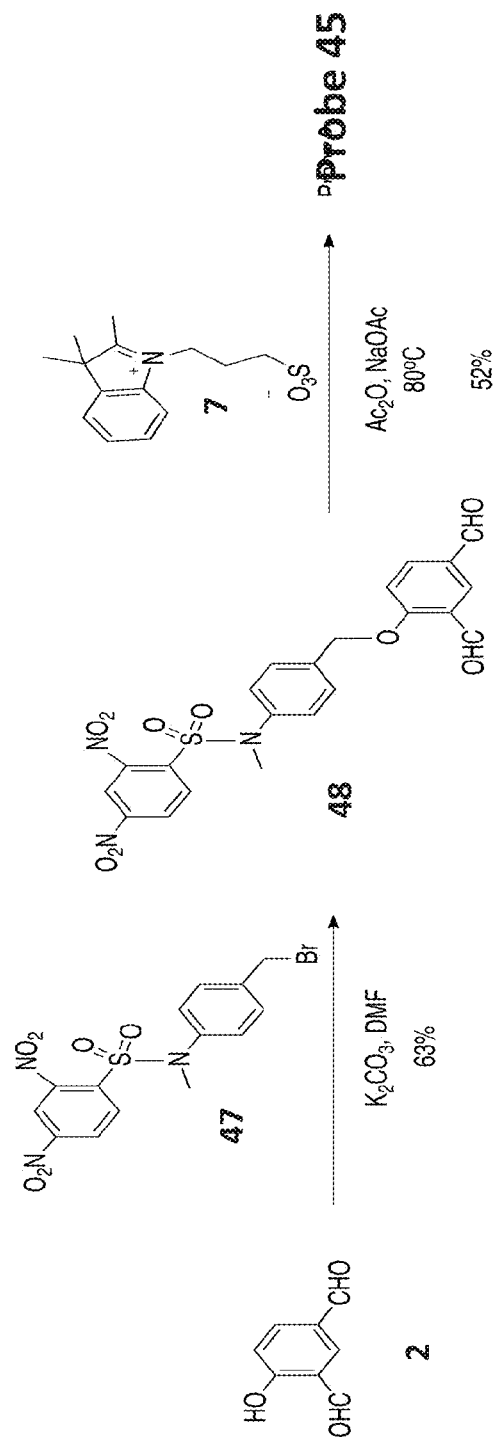
FIG. 29A
FIG. 29B

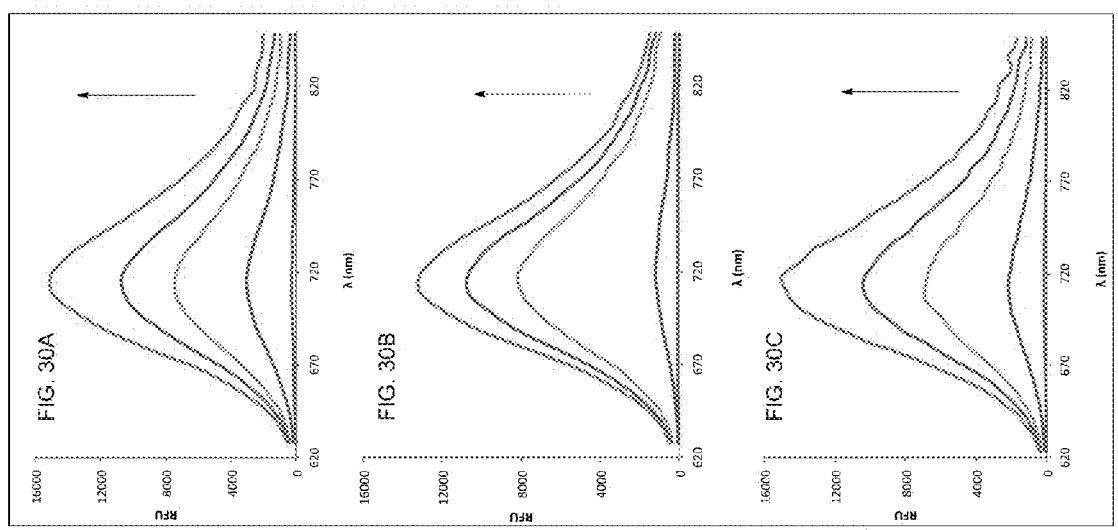

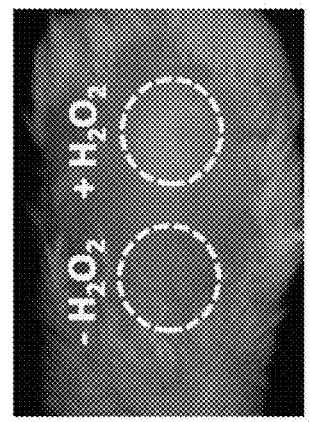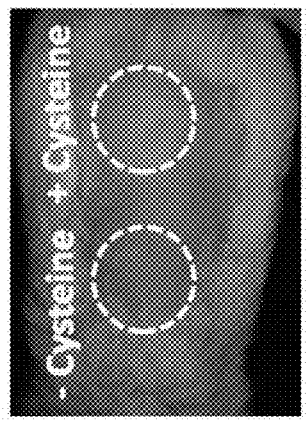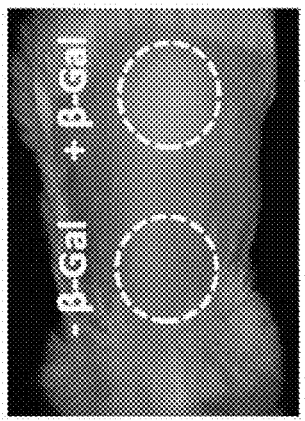
FIG. 34A
FIG. 34B
FIG. 34C

US 9,341,630 B2

ACTIVATABLE FLUOROGENIC COMPOUNDS AND USES THEREOF AS NEAR INFRARED PROBES

RELATED APPLICATIONS

This application is a Continuation-In-Part (CIP) of PCT Patent Application No. PCT/IB2012/051255 having International filing date of Mar. 15, 2012, which claims the benefit of priority under 35 USC 119(e) of U.S. Provisional Patent Application Nos. 61/452,684 filed Mar. 15, 2011, 61/452,688 filed on Mar. 15, 2011 and 61/556,335 filed on Nov. 7, 2011. The contents of the above applications are all incorporated by reference as if fully set forth herein in their entirety.

FIELD AND BACKGROUND OF THE INVENTION

The present invention, in some embodiments thereof, relates to fluorogenic compounds and, more particularly, but not exclusively, to chemically-activatable fluorogenic compounds which upon a chemical event rearrange so as produce a near infrared probe, and to uses thereof.

The use of non-radioactive labels in biochemistry and molecular biology has grown exponentially in recent years. Among the various compounds used as non-radioactive labels, aromatic dyes that produce fluorescent or luminescent signal are especially useful.

Near-infrared spectroscopy (NIRS) is a spectroscopic method that uses the near-infrared region of the electromagnetic spectrum (from about 700 nm to 1400 nm). NIR can typically penetrate much farther into a sample than mid infrared radiation, and is particularly useful in probing bulk material with little or no sample preparation. Optical imaging in a near-infrared (NIR) range of between 650 nm and 900 nm is highly suitable for biological applications since it enables detection of molecular activity in vivo due to high penetration of NIR photons through organic tissues and low autofluorescence background at this range.

Fluorochromes suitable for use in NIRS include, for example, fluorescein labels, Alexa Fluor dyes, cyanine dyes such as Cy2, Cy3, Cy5, Cy7, optionally substituted coumarin, R-phycoerythrin, allophycoerythrin, Texas Red and Princeton Red.

Cyanine dyes have been recognized as useful for NIR imaging, due to the biological compatibility, environmental stability, the large extinction coefficient, narrow emission bands and relatively high quantum yield thereof [Mujumdar ET AL. *Bioconjugate Chem.* 4, 105-11 (1993)], which allow them to penetrate deep tissues and serve as attractive probes for intravital non-invasive imaging.

The cyanine dyes are comprised of two nitrogen-containing moieties (e.g., indolenine based rings), one being in a form of an acceptor moiety (e.g., ammonium) and one in the form of a donor moiety (e.g., amine), which are connected by a series of conjugated double bonds. The dyes are classified by the number (n) of central double bonds connecting the two ring structures; monocarbocyanine or trimethinecarbocyanine when n=1; dicarbocyanine or pentamethinecarbocyanine when n=2; and tricarbocyanine or heptamethinecarbocyanine when n=3.

Cyanine dyes have been developed for use in Fluorescence Resonance Energy Transfer (FRET) assays. Briefly, FRET assays depend on an interaction between two fluorophores, a donor fluorophore and an acceptor fluorophore. When the donor and acceptor molecules are in close enough proximity, the fluorescence of the donor molecule is transferred to the acceptor molecule with a resultant decrease in the lifetime and a quenching of fluorescence of the donor species and a concomitant increase in the fluorescence intensity of the acceptor species. In the case of peptide cleavage reactions, a fluorescent donor molecule and a fluorescent acceptor molecule are attached to a peptide substrate on either side of the peptide bond to be cleaved and at such a distance that energy transfer takes place. A peptide cleavage reaction will separate the donor and acceptor molecules and thus the fluorescence of the donor molecule will be restored.

Cyanine dyes suitable for use as acceptor or "quencher" molecules in a FRET assay have been developed by making certain modifications to cyanine dyes through introduction of chemical groups which have the effect of diminishing or abolishing the fluorescence of the molecule.

For example, a Turn-ON system for a cyanine molecule which utilizes FRET comprises a cyanine dye and a quencher attached to one another through an enzymatically-cleavable linker, to obtain a quenched fluorophore. Once the linker is cleaved by a specific enzyme, the fluorophore separates from the quencher and thus, turn-ON of a fluorescence signal is effected. This approach, however, requires an additional dye (the quencher) apart from the cyanine.

Efforts to design alternative Turn-ON cyanine probes typically had limitations of low quantum yield, low extinction coefficient and complex synthesis [see, for example, Ho et al. *Bioorg. Med. Chem. Lett.* 16, 2599-602 (2006); and Richard et al. *Org. Lett.* 10, 4175-8 (2008)], and only limited specific examples for cyanine probes that involve changes with the π-electrons conjugation have been reported [see, Kundu et al. *Angew. Chem. Int. Ed.* 49, 6134-8 (2010); and Kundu et al. *Angew. Chem. Int. Ed.* 48, 299-303 (2009)].

Cyanine molecules coupled to targeting peptides have been reported. See, for example, Tung et al., Bioconjug Chem. 1999 10(5):892-6, which discloses a cathepsin-sensitive system that comprises a cyanine-peptide conjugate; and U.S. Pat. No. 6,217,848, which disclosed dye-peptide conjugates, including several cyanine dyes with a variety of bis- and tetrakis (carboxylic acid) homologues, for targeted delivery.

Additional background art includes Samanta et al. *Chem. Commun.*, 2010, 46, 7406-7408; Dickinson et al. *J. Am. Chem. Soc.* 132, 5906-15 (2010); Dickinson et al. *Nat. Chem. Biol.* 7, 106-12 (2011); Miller et al. *Nat. Chem. Biol.* 3, 263-7 (2007); Van de Bittner et al. *Proc. Natl. Acad. Sci.* (2010)]; Avital-Shmilovici, M. & Shabat, D. *Biorg. Med. Chem.* 18, 3643-7 (2010); Sella, E. & Shabat, D. *Chem. Commun.*, 5701-3 (2008); Sella, E. & Shabat, D. *J. Am. Chem. Soc.* 131, 9934-6 (2009); Wainstein et al., *Chem. Commun.* 2010; 46: 553-5; Karton-Lifshin et al., *J. Phys. Chem. A.* 2012 Jan. 12; 116(1):85-92; Karton-Lifshin et al., *J. Am. Chem. Soc.* 2011 Jul. 20; 133(28):10960-5; and Sella et al., *J. Am. Chem. Soc.*, 132, 3945-3952.

SUMMARY OF THE INVENTION

Previous efforts to design such Turn-ON probes typically had limitations of low quantum yield, low extinction coefficient and complex synthesis.

In a search for an improved approach to a Turn-ON mechanism for molecules with cyanine spectroscopic characteristics, the present inventors have designed and successfully prepared and practiced a cyanine-based Turn-ON NIR probe with a modular triggering mechanism. This modular approach for cyanine-based probe can be adjusted as desired, by introducing a trigger unit suitable for a desired analyte. Depending on the trigger unit in the probe, NIR imaging of a variety of organs and tissues can be applied and utilized in a variety of medical and diagnosis applications.

The novel cyanine-based NIR probes described herein can be synthesized through a simple (e.g., two-step) procedure and have a relative high quantum yield and large extinction coefficient. The probe's design allows formation of a cyanine-like dye through π-electrons relocation, upon a chemical event that is induced by an appropriate analyte.

The NIR probes disclosed herein are based on relocalization of π-electrons in a system that comprises a donor-containing moiety and two or more acceptor-containing moieties, which is effected by a chemical event. The donor-containing moiety and the acceptor-containing moieties form a conjugated π-electron system with no delocalization of the π-electrons (no resonating electrons), such that the probe is incapable of emitting light (e.g., near infrared light). Upon a chemical event, the donor-containing moiety rearranges such that it transfers electrons to an acceptor-containing moiety and as a result, a π-electron system between the former two or more acceptor-containing moieties, with delocalized, resonating electrons between these moieties, is obtained. As a result of the presence of delocalized, resonating electrons, capability to emit light at the desired near IR range (e.g., between 650 nm and 900 nm) is obtained, as illustrated in FIG. 19.

According to an aspect of some embodiments of the present invention there is provided a fluorogenic compound comprising at least two acceptor-containing moieties and a donor-containing moiety arranged such that: (i) the at least two acceptor-containing moieties and the donor-containing moiety form a conjugated π-electron system devoid of resonating electrons, such that the compound is incapable of emitting NIR infrared light; and (ii) upon a chemical event, the donor-containing moiety rearranges so as to transfer π-electrons to one of the acceptor-containing moieties and, as a result, the acceptor-containing moiety becomes a donor-containing moiety to at least one another acceptor-containing moiety, to thereby enable emission of near infrared light.

According to some embodiments of the invention, the donor-containing moiety comprises an aromatic moiety.

According to some embodiments of the invention, the donor-containing moiety comprises an aromatic moiety substituted by an electron-donating group such as hydroxyl.

According to some embodiments of the invention, the donor-containing moiety is such that upon the chemical event, it rearranges by undergoing a 1,4-elimination.

According to some embodiments of the invention, the chemical event is generated by an analyte.

According to some embodiments of the invention, the chemical event comprises cleavage in the donor-containing moiety.

According to some embodiments of the invention, the donor-containing moiety comprises a trigger unit, and wherein the chemical event comprises cleavage of the trigger unit.

According to some embodiments of the invention, the cleavage of the trigger unit is effected in the presence of an analyte.

According to some embodiments of the invention, the analyte is associated with a medical condition.

According to some embodiments of the invention, the analyte is an enzyme overexpressed in organs or tissues afflicted by the medical condition.

According to some embodiments of the invention, the medical condition is cancer.

According to some embodiments of the invention, the enzyme is selected from the group consisting of a cathepsin, a caspase, a histone deacetylase, a matrix metalloproteinase, a serine or threonine kinase and a serine kinase.

According to some embodiments of the invention, the analyte is a substance that is produced in organs or tissues in response to the medical condition.

According to some embodiments of the invention, the medical condition is selected from the group consisting of inflammation, hypoxia, apoptosis, cerebral ischemia, osteoporosis, an angiogenesis-dependent disease or disorder and an autoimmune disease or disorder.

According to some embodiments of the invention, the fluorogenic compound further comprises a therapeutically active agent being attached to the donor-containing moiety.

According to some embodiments of the invention, the therapeutically active agent is attached to the donor-containing moiety such that upon the chemical event, the therapeutically active agent is released.

According to some embodiments of the invention, the fluorogenic compound has the general Formula I:

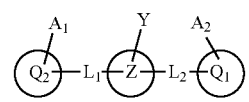

Formula I wherein:

$Q_1$ and $Q_2$ are each independently an acceptor-containing moiety;

$A_1$ and $A_2$ are each an acceptor group in the acceptor-containing moieties;

Z and Y form the donor-containing moiety; and $L_2$ and $L_1$ are each independently a linking moiety or absent, and each is such that the $Q_1$ and $Q_2$ acceptor-containing moieties and the Z—Y donor containing moiety form the conjugated π-electron system.

According to some embodiments of the invention, the acceptor-containing moieties and the donor-containing moiety form together a modified cyanine structure.

According to some embodiments of the invention, the modified cyanine structure comprises two acceptor-containing moieties linked therebetween via a carbomethine-containing chain, and wherein the donor-containing moiety forms a part of, or is attached to, the carbomethine-containing chain.

According to some embodiments of the invention, each of the acceptor-containing moieties is independently a =N⁺RaRb moiety, wherein Ra and Rb are each independently hydrogen, alkyl or cycloalkyl or, alternatively, Ra and Rb form together a heteroalicyclic or a heteroaryl.

According to some embodiments of the invention, the fluorogenic compound has the general Formula II:

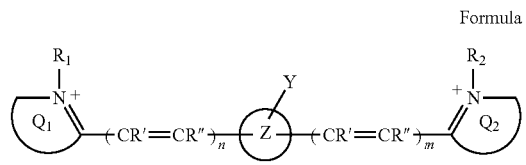

Formula II wherein:

$Q_1$ and $Q_2$ are each independently a substituted or unsubstituted heterocyclic moiety (containing the positively charged nitrogen atoms indicated in Formula II and each forming an acceptor-containing moiety;

$R_1$ and $R_2$ are each independently selected from the group consisting of hydrogen, alkyl and cycloalkyl;

n and m are each independently an integer of from 0 to 4;

R' and R" are each independently hydrogen, alkyl or cycloalkyl, or, alternatively, R' and R" form together an aryl; and Z and Y together form the donor-containing moiety as described herein.

According to some embodiments of the invention, $Q_1$ and $Q_2$ are each independently a substituted or unsubstituted heteroaryl, such as, but not limited to, pyridinium, indolinium, and picolinium (methylpyridinium).

According to some embodiments of the invention, the fluorogenic compound has the general formula IIIB:

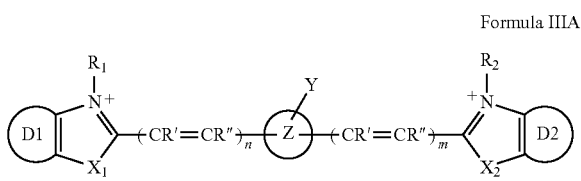

Formula IIIA wherein:

$D_1$ and $D_2$ are each independently an aromatic moiety; and $X_1$ and $X_2$ are each independently selected from the group consisting of $CR_3R_4$, $NR_3$, and S, wherein $R_3$ and $R_4$ are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide.

According to some embodiments of the invention, $D_1$ and $D_2$ are each a substituted or unsubstituted phenyl.

According to some embodiments of the invention, $X_1$ and $X_2$ are each independently $CR_3R_4$.

According to some embodiments of the invention, $R_3$ and $R_4$ are each an alkyl.

According to some embodiments of the invention, $R_1$ and $R_2$ are each hydrogen.

According to some embodiments of the invention, $R_1$ and $R_2$ are each independently a substituted or unsubstituted alkyl.

According to some embodiments of the invention, Z and Y are such that the chemical event comprises cleavage of the Y.

According to some embodiments of the invention, the fluorogenic compound has the general formula IIIA:

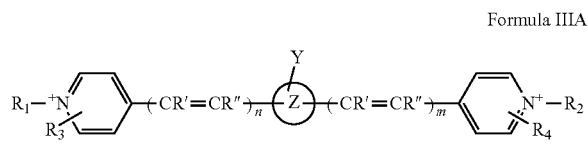

Formula IIIA wherein:

$R_1$ and $R_2$ are each independently selected from the group consisting of hydrogen, alkyl, cycloalkyl and aryl, heteroalicyclic, heteroaryl;

n and m are each independently an integer of from 0 to 4;

$R_3$ and $R_4$ are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide;

R' and R" are each independently hydrogen, alkyl or cycloalkyl, or, alternatively, R' and R" form together an aryl; and Z and Y form together a donor-containing moiety, as described herein.

According to some embodiments of the invention, the fluorogenic compound further comprises a third acceptor-containing moiety and being such that the first, second and third acceptor-containing moieties and the donor-containing moiety form the conjugated π-electrons system devoid of resonating electrons.

According to some embodiments of the invention, the fluorogenic compound is for use in determining a presence and/or a level of an analyte that generates the chemical event.

According to an aspect of some embodiments of the present invention there is provided a fluorescent compound having the general Formula IV:

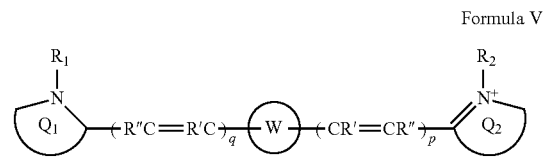

Formula V wherein:

$Q_1$ and $Q_2$ are each independently such that form a substituted or unsubstituted heterocyclic moiety;

$R_1$ and $R_2$ are each independently selected from the group consisting of hydrogen, alkyl, cycloalkyl and aryl, heteroalicyclic, heteroaryl;

p and q are each independently an integer of from 0 to 4;

R' and R" are each independently hydrogen, alkyl or cycloalkyl, or, alternatively, R' and R" form together an aryl; and W is a group that comprises an aromatic moiety, wherein the π-electrons of said aromatic moiety are conjugated to the π electrons of said —(CR'=CR")p- and said —(CR'=CR")q—, such that delocalization of π electrons is effected between the ammonium and the amine groups in the molecule.

According to some embodiments of the present invention, at least one of $Q_1$ and $Q_2$ forms a pyridine ring.

According to some embodiments of the present invention, the fluorescent compound has the general Formula IVA:

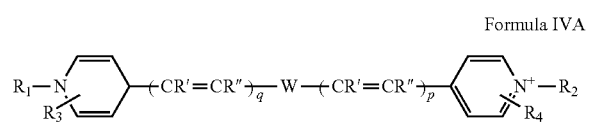

Formula IVA wherein:

$R_1$ and $R_2$ are each independently selected from the group consisting of hydrogen, alkyl, cycloalkyl and aryl, heteroalicyclic, heteroaryl;

p and q are each independently an integer of from 0 to 4;

$R_3$ and $R_4$ are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide;

R' and R" are each independently hydrogen, alkyl or cycloalkyl, or, alternatively, R' and R" form together an aryl; and W is as described herein.

In some embodiments, the fluorescent compound has the general Formula IVB:

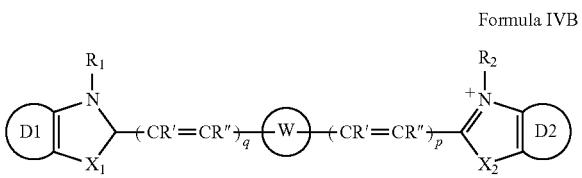

Formula IVB wherein:

$D_1$ and $D_2$ are each independently an aromatic moiety;

$X_1$ and $X_2$ are each independently selected from the group consisting of CR'R", NR', O, S and SiR'R", wherein R' and R" are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide;

$R_1$ and $R_2$ are each independently selected from the group consisting of hydrogen, alkyl, cycloalkyl and aryl, heteroalicyclic, heteroaryl;

p and q are each independently an integer of from 0 to 4; and

W is a group that comprises an aromatic moiety, wherein the π-electrons of the aromatic moiety are conjugated to the π electrons of the —(CH═CH)p- and the —(CH═CH)q—, such that delocalization of π electrons is effected between the ammonium and the amine groups in the molecule.

According to some embodiments of the invention, the fluorogenic compound as described herein or the fluorescent compound as described herein, is for use in imaging a sample.

According to an aspect of some embodiments of the invention, there is provided a use of the fluorogenic compound as described herein, in the manufacture of an imaging agent.

According to an aspect of some embodiments of the invention, there is provided a method of determining a presence and/or level of an analyte in a sample, the method comprising contacting the sample with the fluorogenic compound as described herein; and collecting a light emitted from the sample, wherein a presence and/or level of the light is indicative of the presence and/or level of the analyte.

According to some embodiments of the invention, the light has a wavelength within a near infrared range.

According to an aspect of some embodiments of the invention, there is provided a method of imaging a sample, the method comprising contacting the sample with the fluorogenic compound as described herein or with the fluorescent compound as described herein, and collecting a light emitted from the sample.

According to some embodiments of the invention, the light has a wavelength within a near infrared range.

According to an aspect of some embodiments of the invention, there is provided a pharmaceutical composition comprising the fluorogenic compound as described herein and a pharmaceutically acceptable carrier.

According to some embodiments of the invention, the chemical event is generated by an analyte and wherein the composition is identified for use in determining a presence and/or level of the analyte in a sample.

According to some embodiments of the invention, the analyte is associated with a medical condition, and wherein determining a presence and/or level of the analyte is being for determining a presence or progression of the medical condition.

According to some embodiments of the invention, the analyte is an enzyme overexpressed in organs or tissues afflicted by the medical condition.

According to some embodiments of the invention, the analyte is produced in response to the medical condition.

According to some embodiments of the invention, the medical condition is selected from the group consisting of cancer, a proliferative disease or disorder, an inflammatory disease or disorder, an ocular disease, an autoimmune disease, a gastrointestinal disease, angiogenesis-dependent diseases and disorders, cerebral ischemia, diabetes, arthritis, macular degeneration, diabetic retinopathy, atherosclerosis, heart failure, psoriasis, osteoporosis and osteoarthritis.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
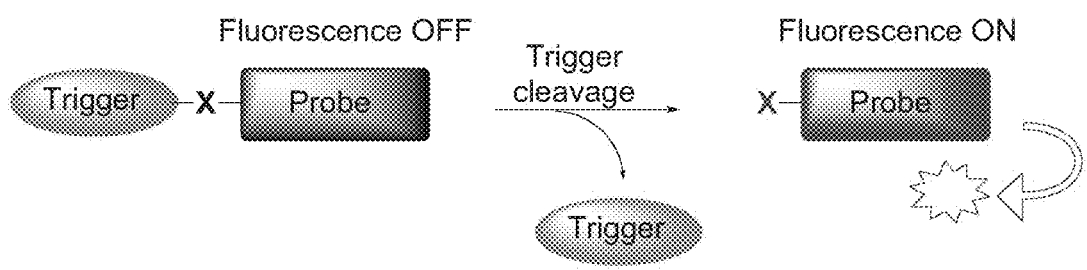
Figure 1B:
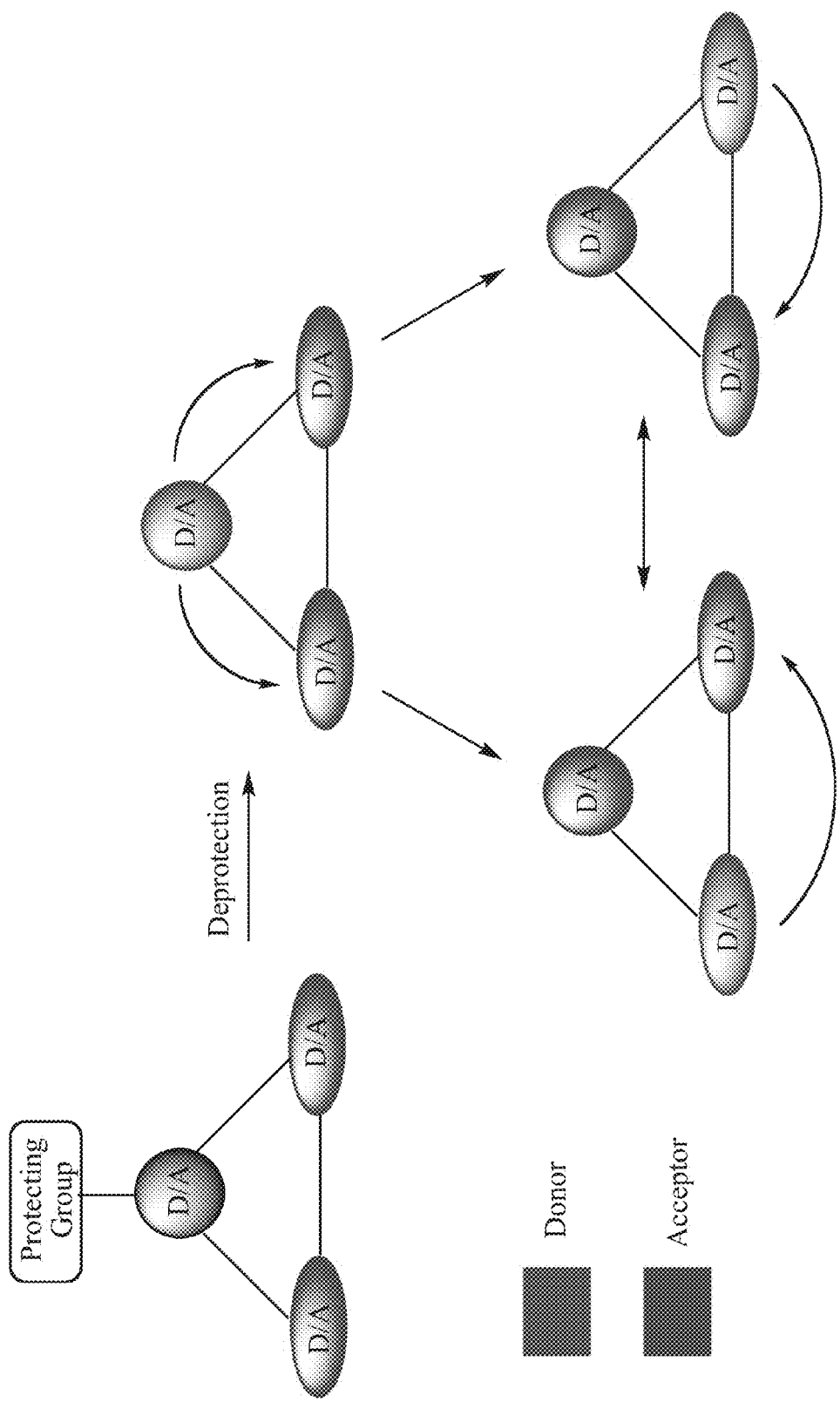
Figure 2A:
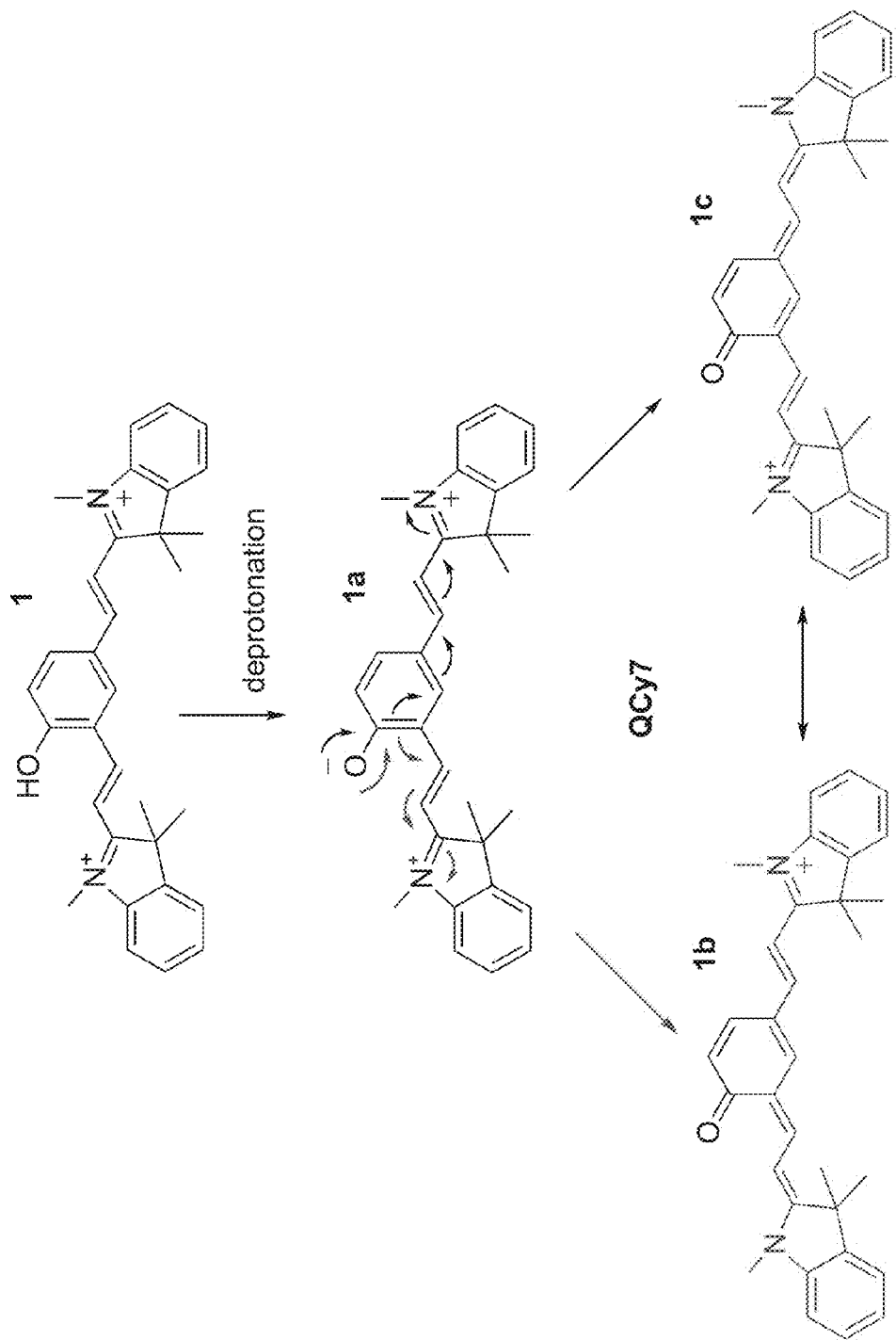
Figure 2A:
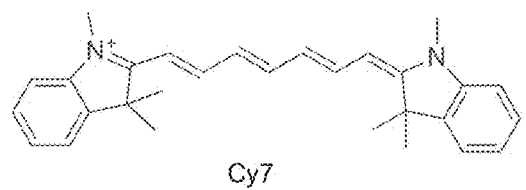
Figure 2B:
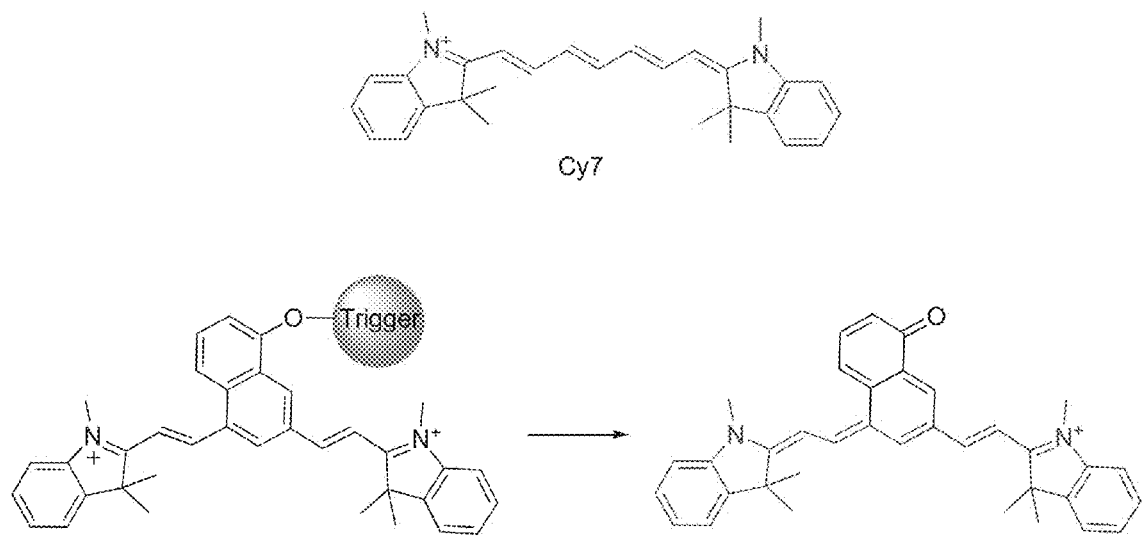
Figure 2C:
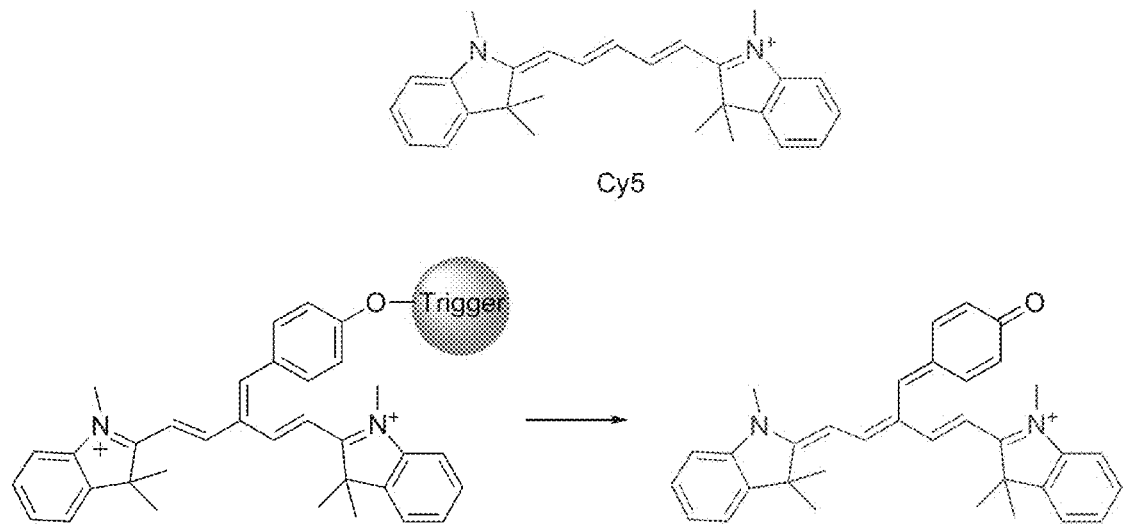
Figure 2D:
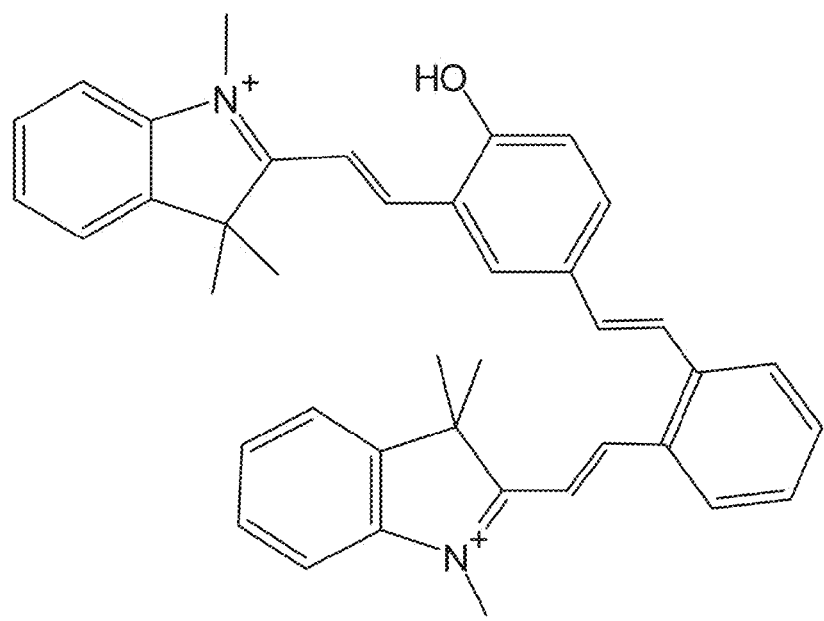
Figure 2E:
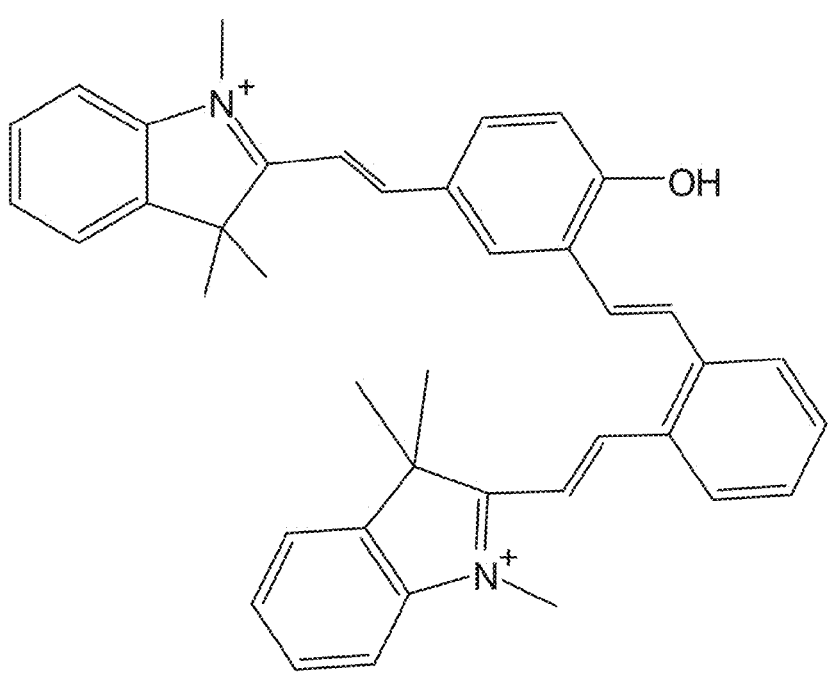
Figure 2F:
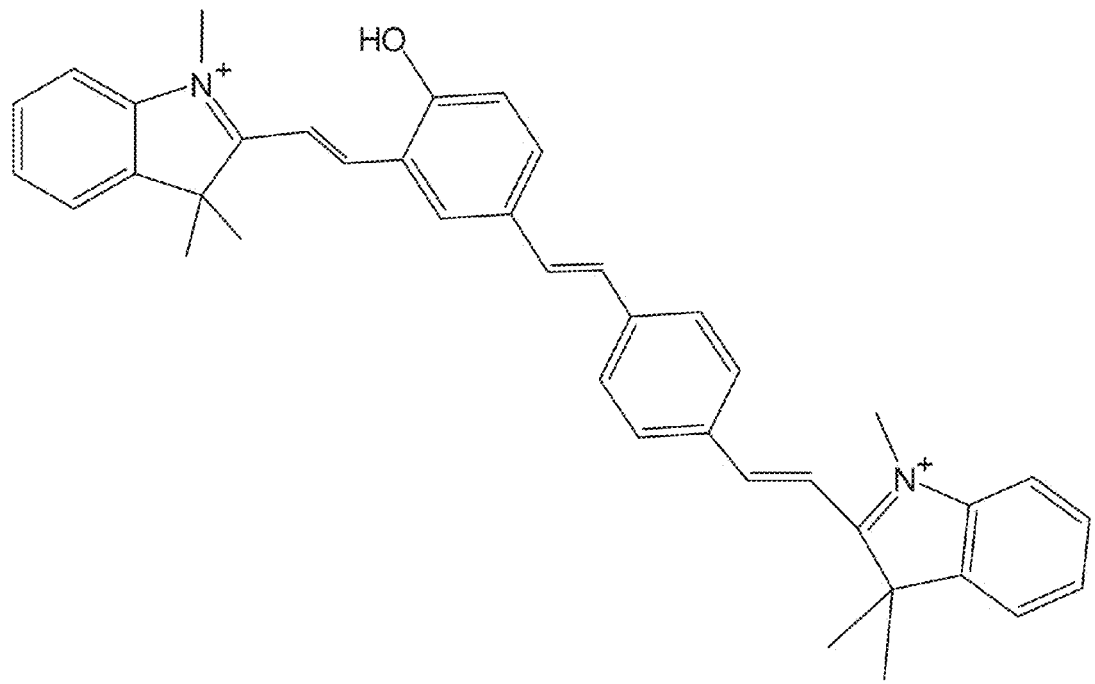
Figure 2G:
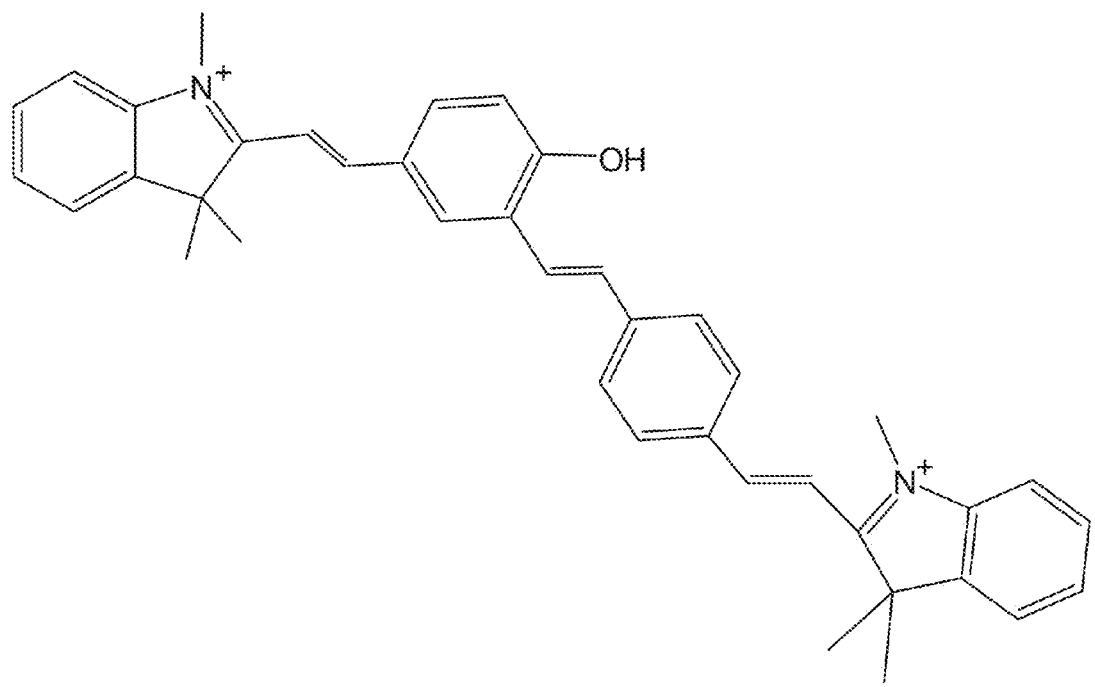
Figure 2H:
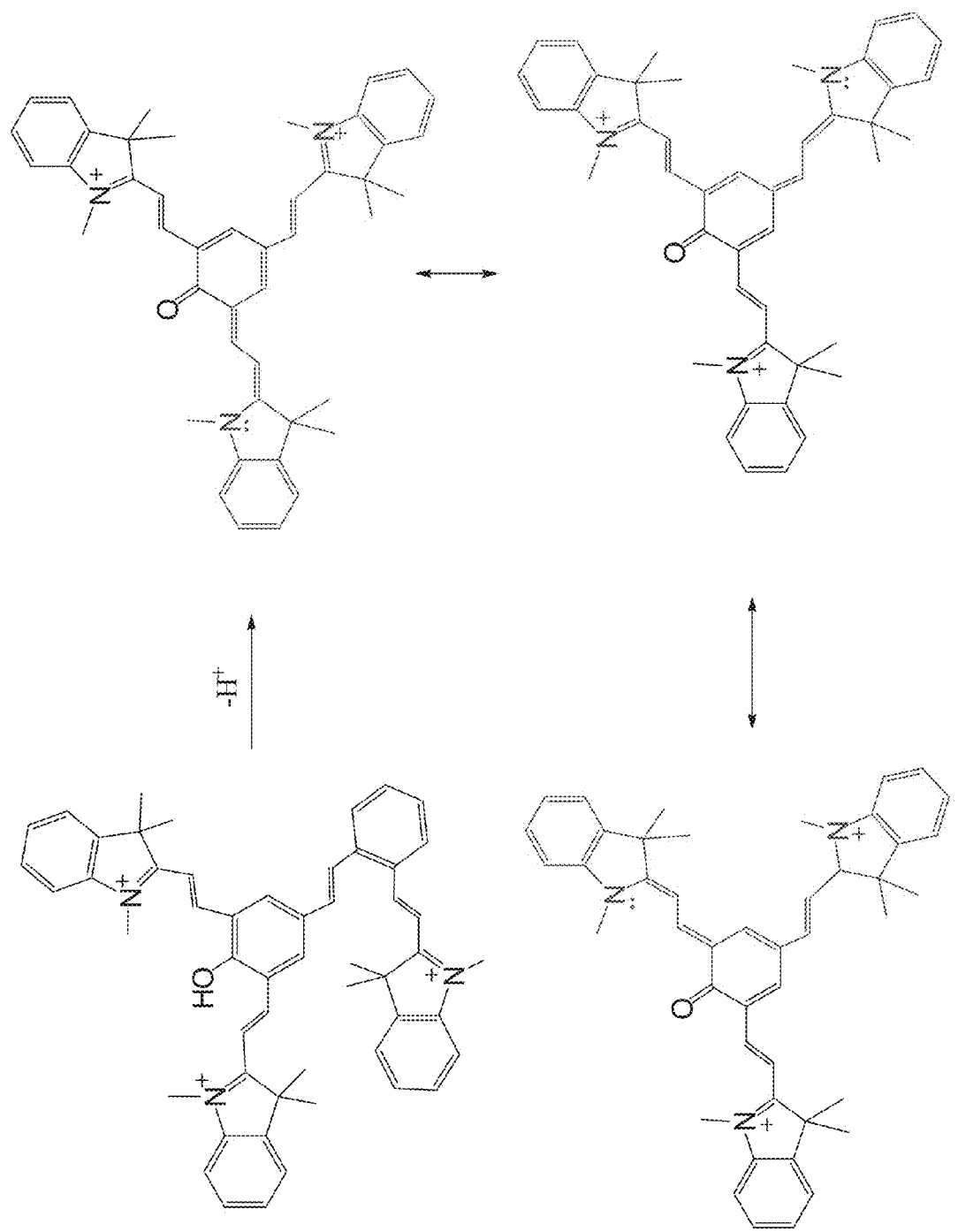
Figure 3A:
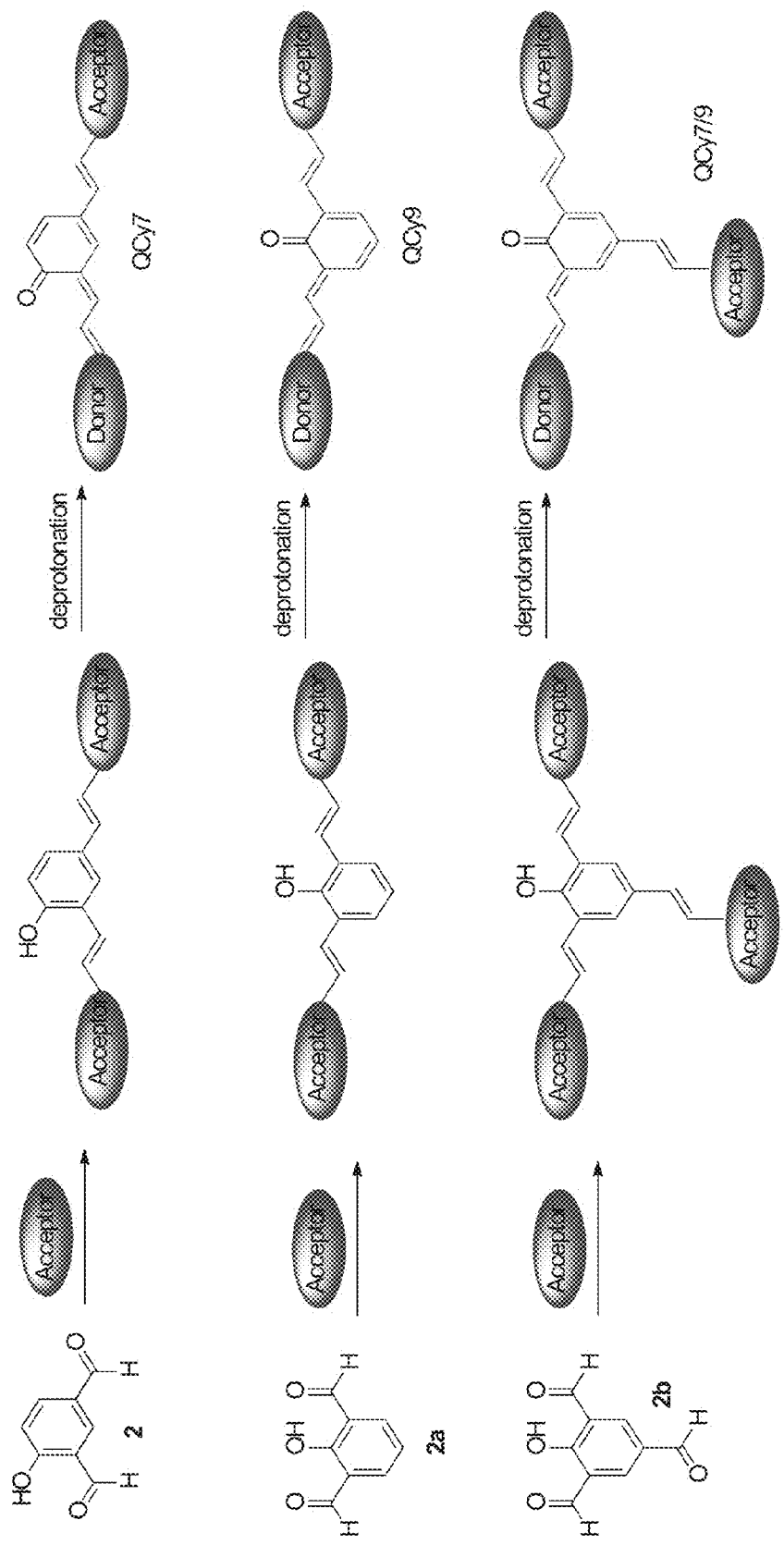
Figure 3B:
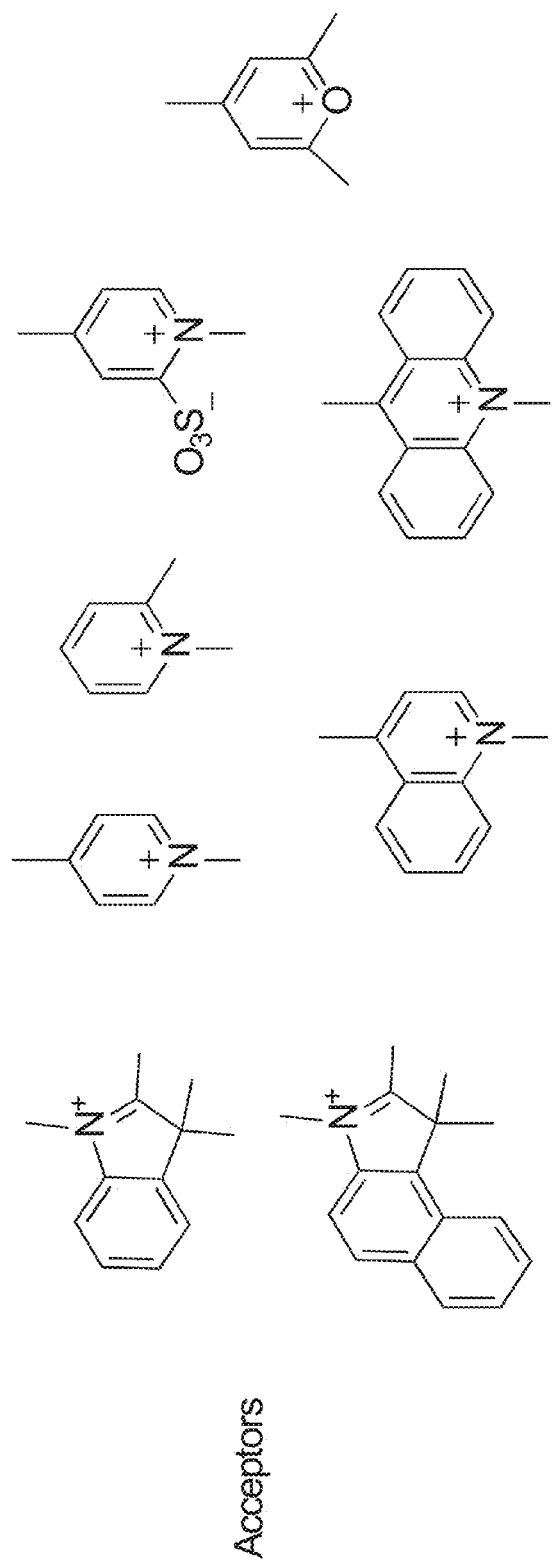
Figure 4A:
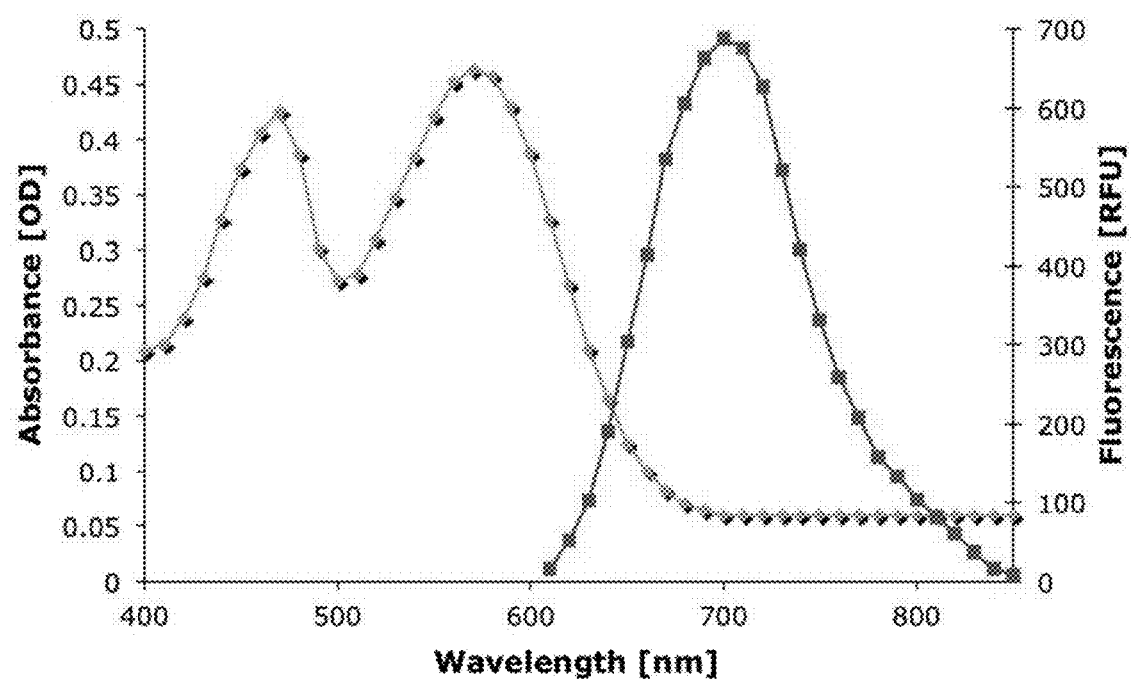
Figure 4B:
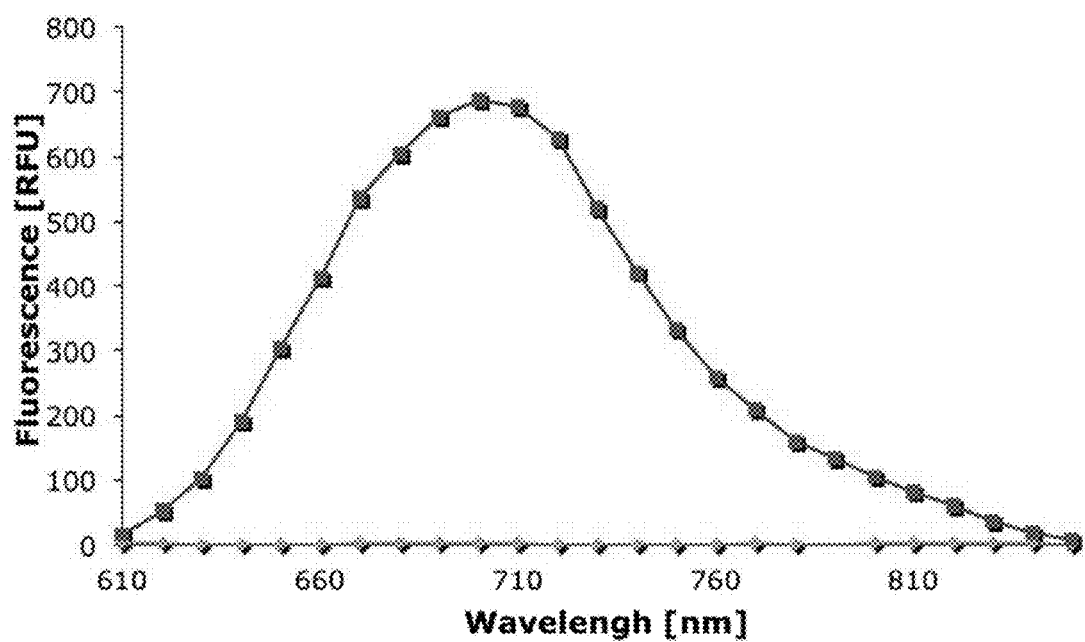
Figure 5A:
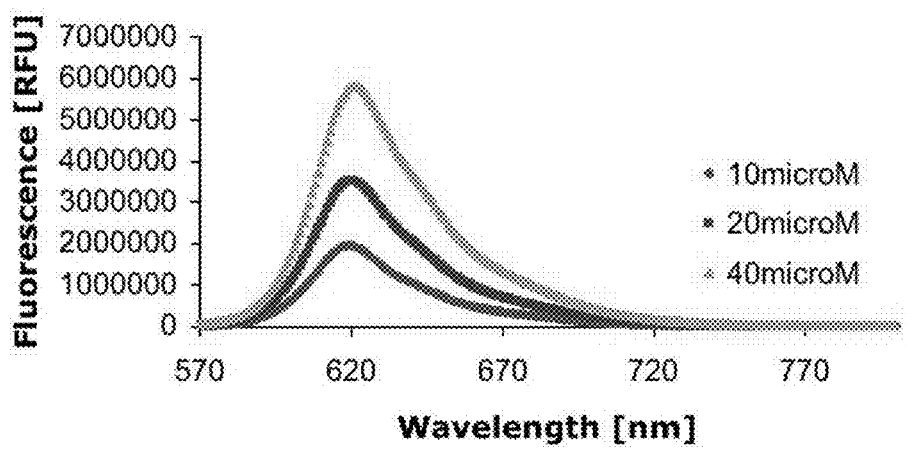
Figure 5B:
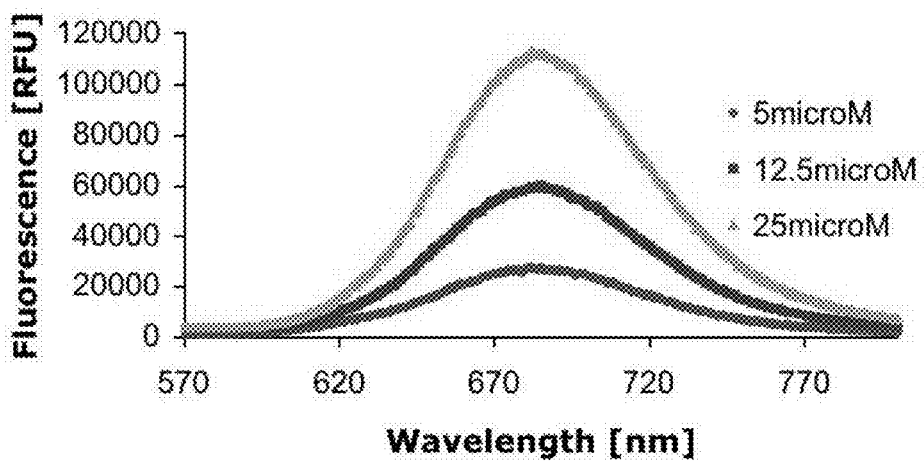

FIGS. 1A-B present a Background art schematic illustration of a classic mechanism for a modular Turn-ON fluorescence probe (FIG. 1A) and a schematic illustration of the electronic rearrangement that activates a fluorogenic compound according to some embodiments of the present invention (FIG. 1B);

FIGS. 2A-H present schematic illustrations of exemplary cyanine-based Turn-ON probes with NIR fluorescence, according to some embodiments of the present invention, with FIG. 2A presenting a donor-two-acceptors exemplary Compound 1, and its corresponding, resonating, dye compound QCy7, compared to the cyanine compound Cy7, FIG. 2B presenting another example of a donor-two-acceptors exemplary compound analogous to Cy7, having a masked donor moiety, and the dye compound obtained upon its activation, FIG. 2C presenting another example of a donor-two-acceptors exemplary compound analogous to Cy5, having a masked donor moiety, and the dye compound obtained upon its activation, FIGS. 2D-G presenting exemplary donor-two-acceptors exemplary compounds having versatile configurations of the delocalized π-electrons system and FIG. 2H presenting an exemplary donor-three-acceptors and its corresponding, resonating, dye compound;

FIGS. 3A-B present schemes depicting exemplary compounds according to some embodiments of the present inventions, and their corresponding dye compounds, as obtained using various phenols as starting materials (FIG. 3A), and the chemical structures of exemplary acceptor moieties according to some embodiments of the present invention (FIG. 3B);

FIGS. 4A-B preset the absorption and fluorescence spectra of QCy7, generated from Compound 1 in PBS 7.4 [100 µM] (FIG. 4A) and the NIR fluorescence spectra of QCy7, generated from Compound 1 (red) in comparison to that of Acetate Compound 3 (blue) in PBS 7.4 [100 µM] (λex=560 nm) (FIG. 4B);

FIGS. 5A-B present plots showing the fluorescence intensity vs. wavelength of Cresyl violet in methanol (FIG. 5A), and QCy7, generated from Compound 1, in PBS 7.4 (FIG. 5B), at the indicated concentrations, taken at excitation wavelength of 560 nm, using fluoromax-3 fluorometer.

Figure 6A:
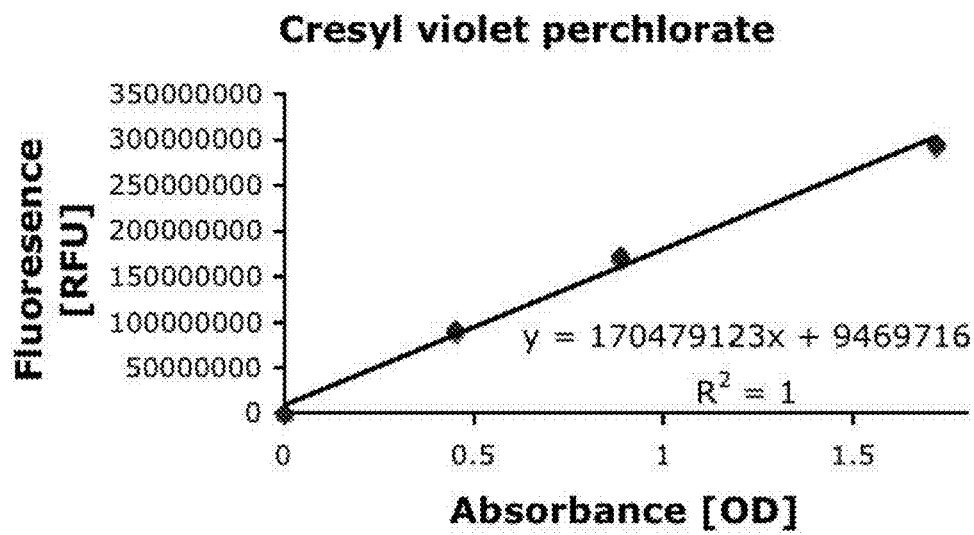
Figure 6B:
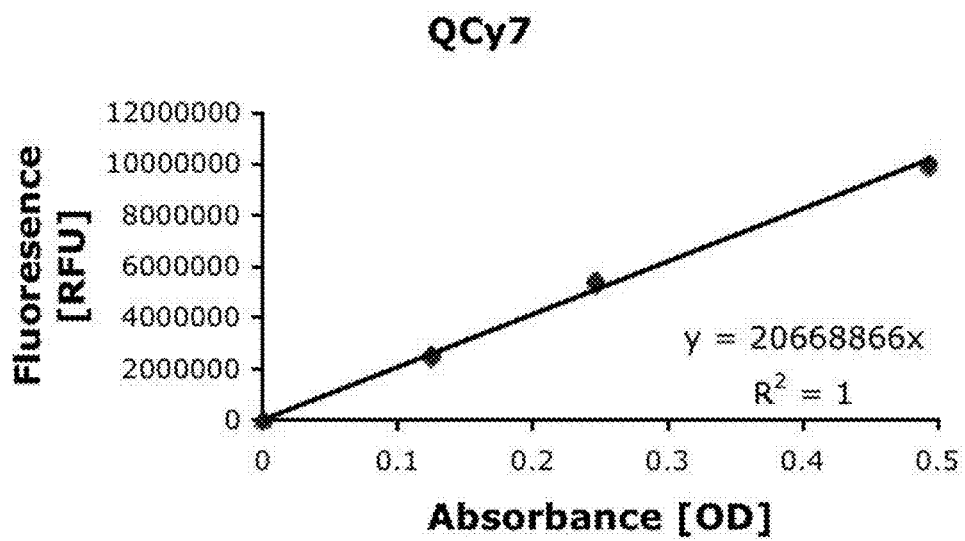

FIGS. 6A-B present linear plots of the fluorescence intensity vs. absorbance of the reference compound Cresyl violet (FIG. 6A) and of QCy7 (FIG. 6B).

Figure 7:
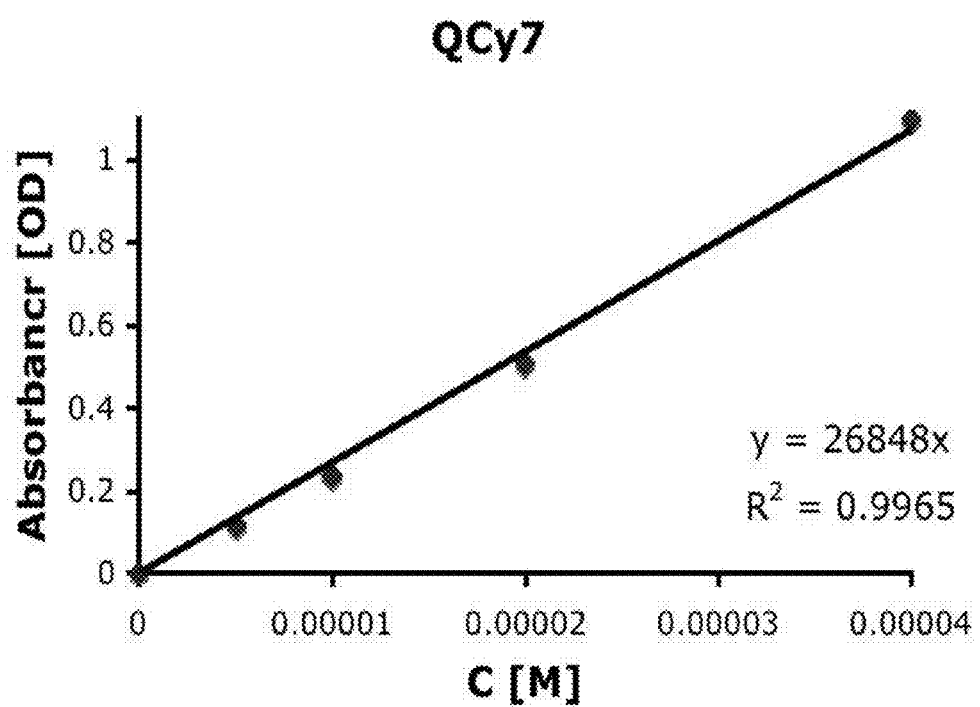
Figure 8A:
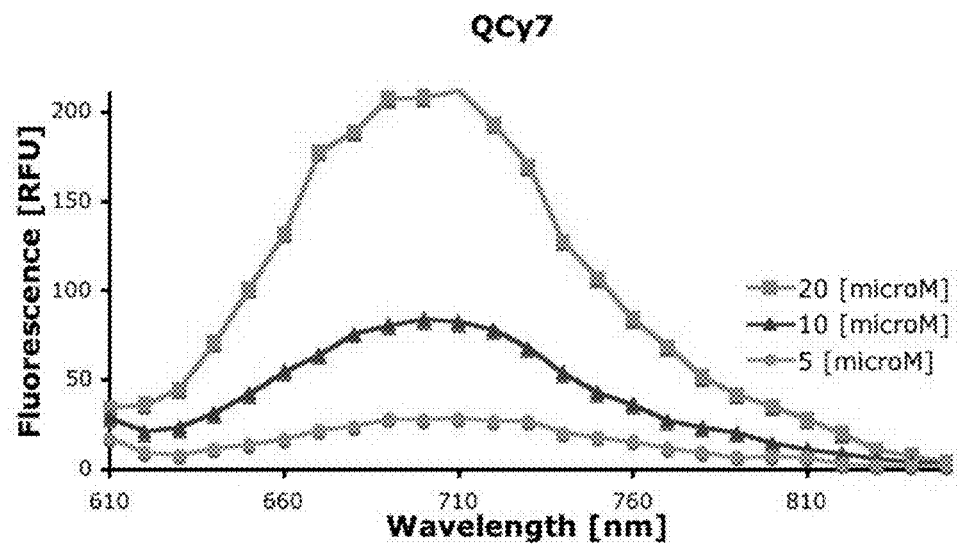
Figure 8B:
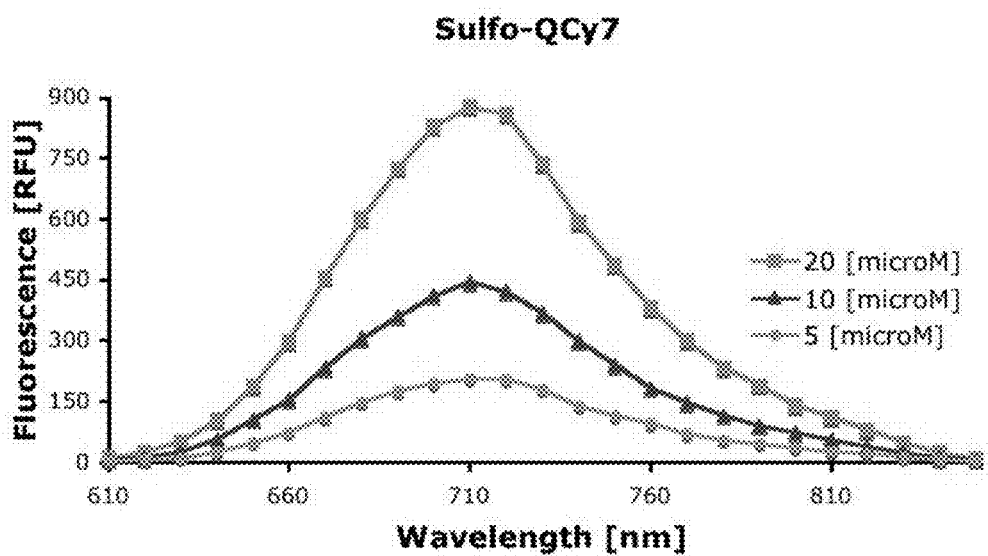

FIG. 7 presents a linear plot of the absorbance of QCy7 as a function of its concentration in PBS 7.4, measured at 560 nm;

FIGS. 8A-B present plots showing the fluorescence intensity vs. wavelength of QCy7, generated from Compound 1 (FIG. 8A), and Sulfo-QCy7, generated from Compound 9 (FIG. 8B) in PBS 7.4, at the indicated concentrations, taken at excitation wavelength of 560 nm, using fluoromax-3 fluorometer.

Figure 9A:
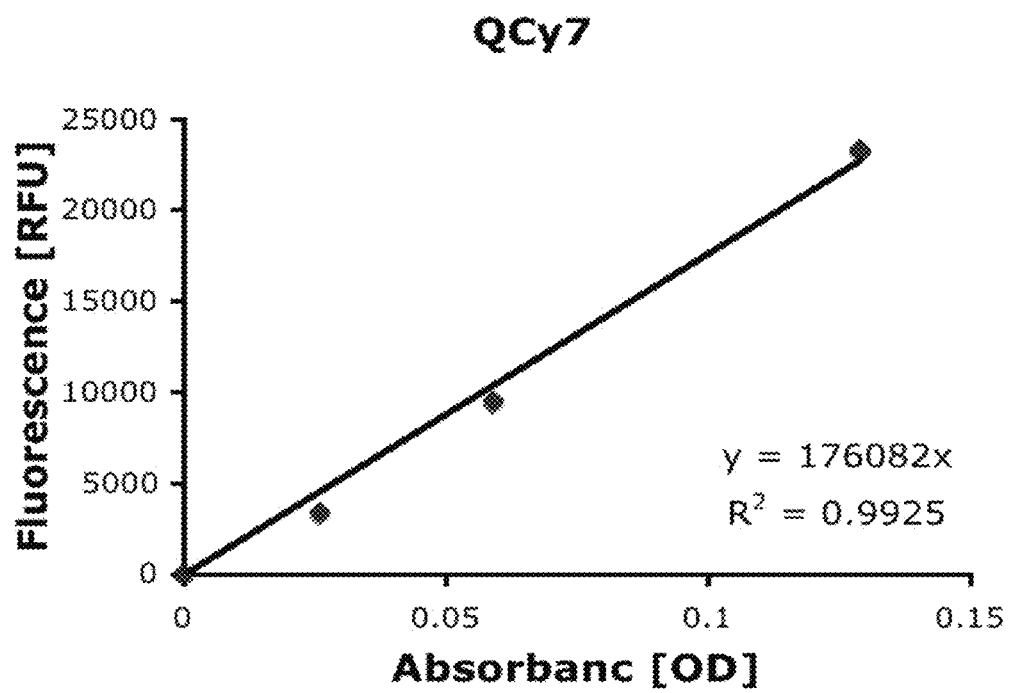
Figure 9B:
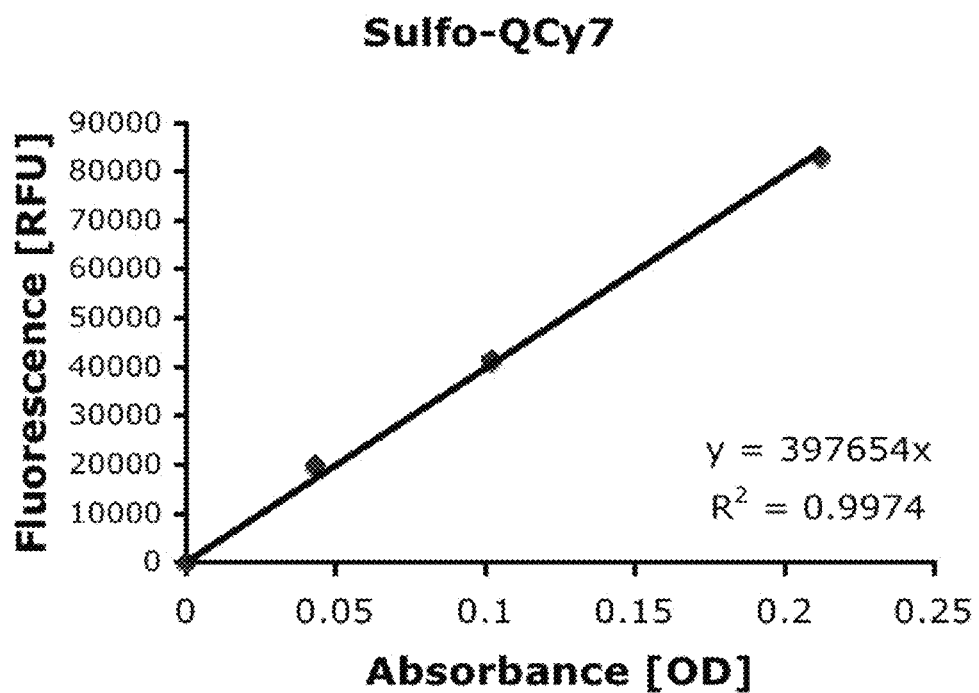
Figure 10:
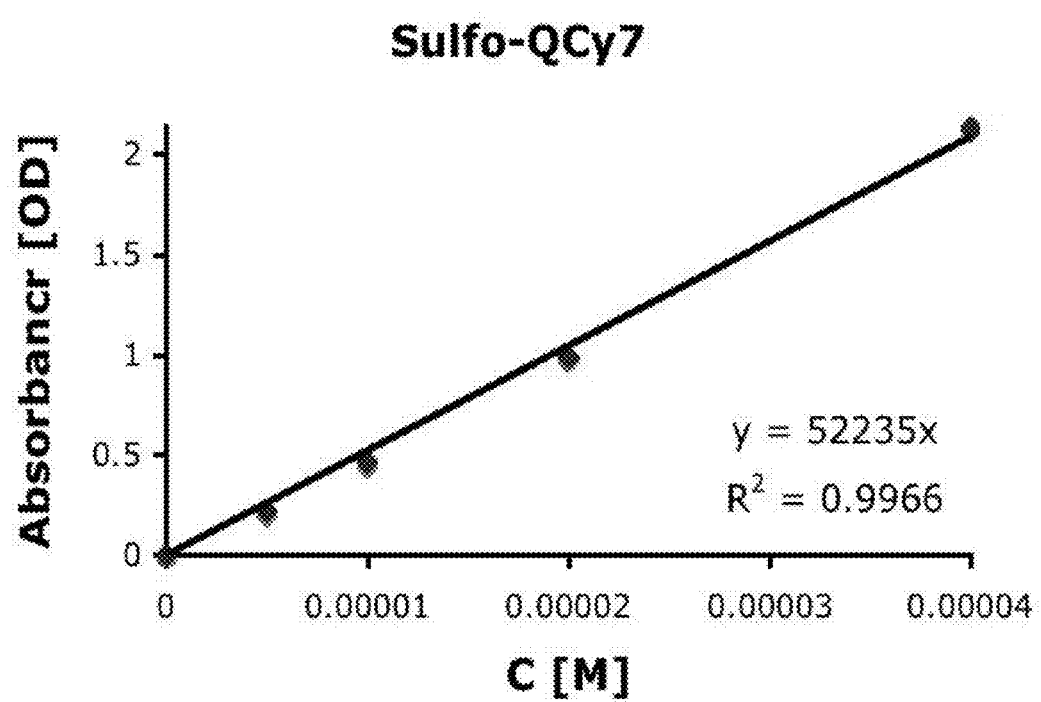
Figure 11:
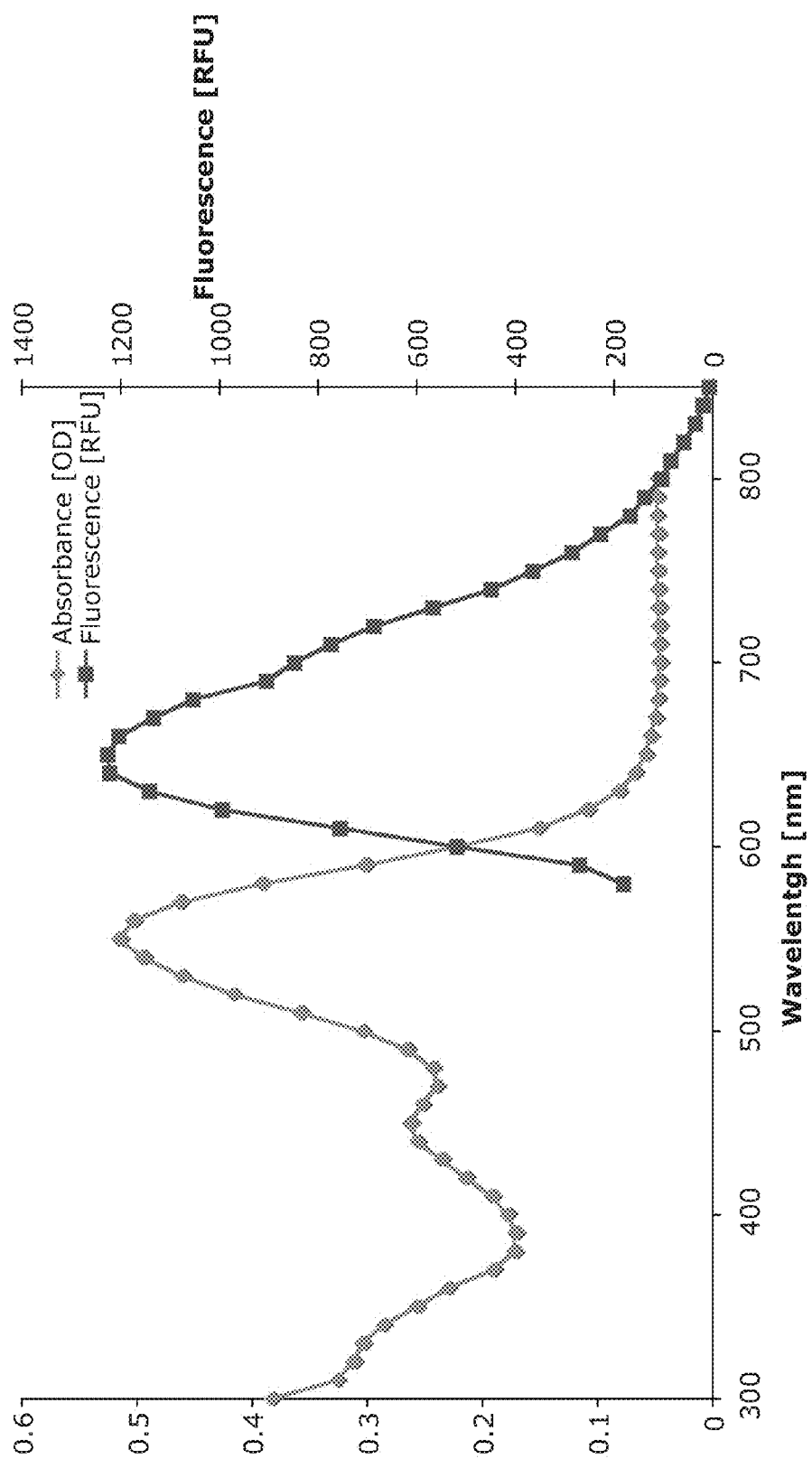
Figure 12:
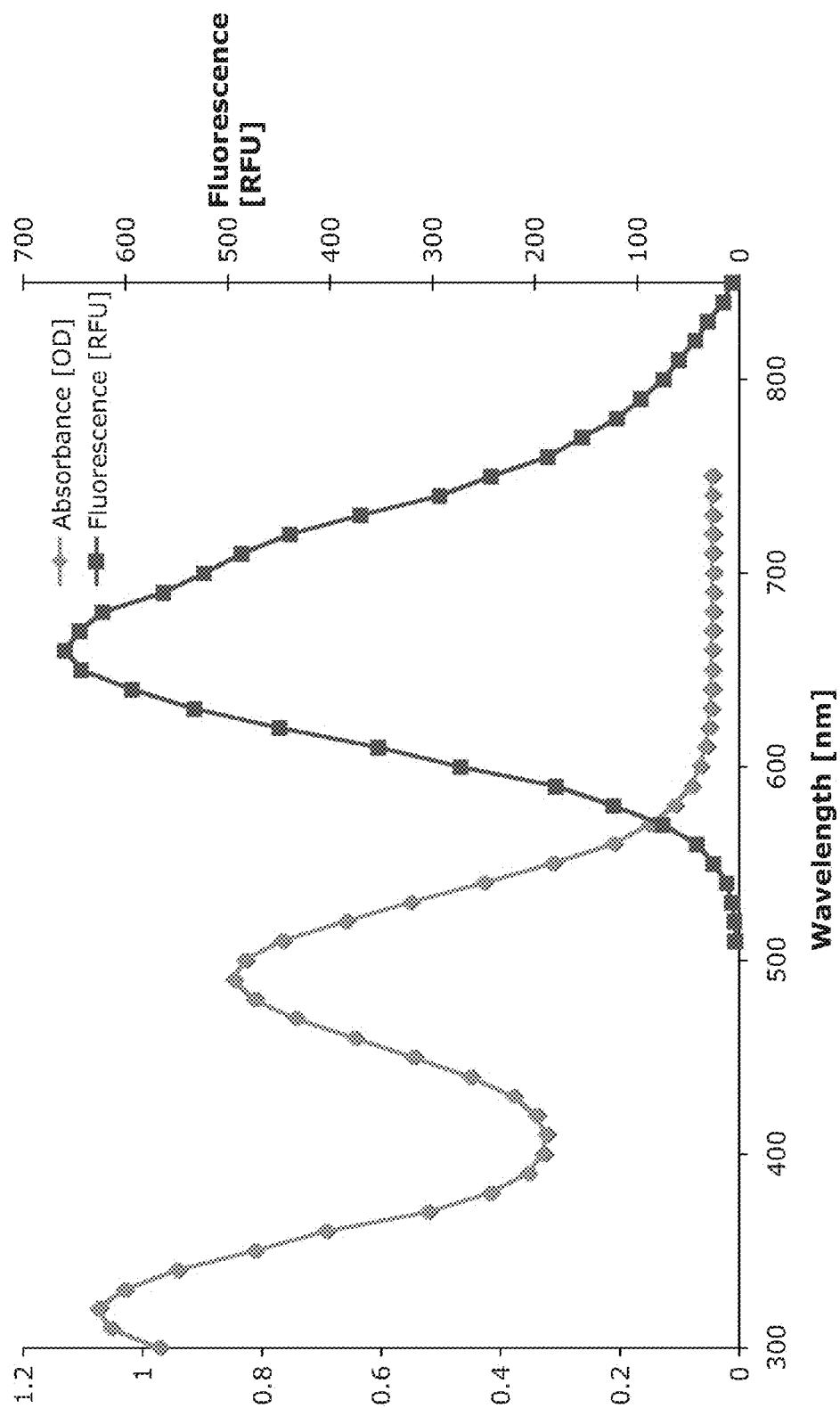
Figure 13:
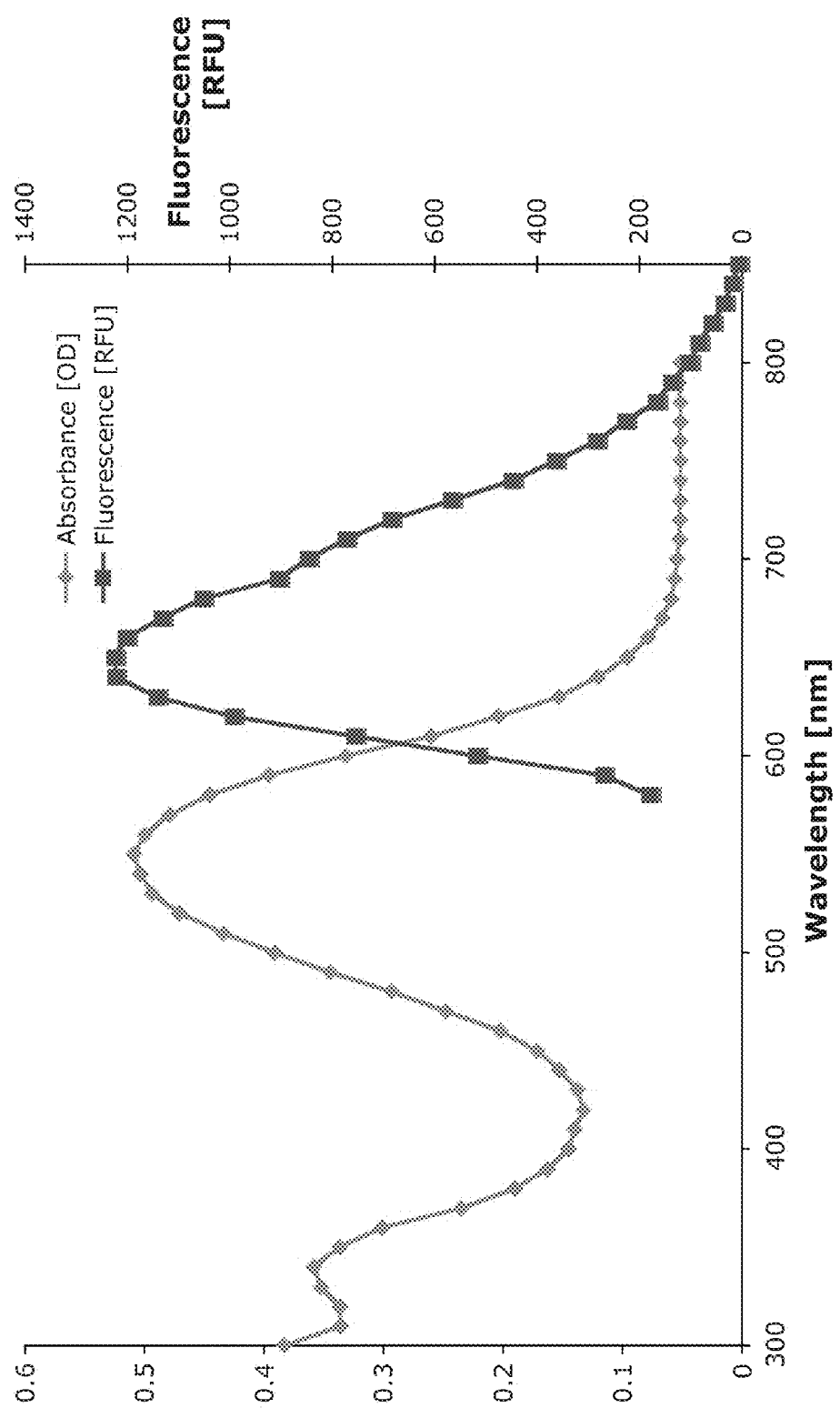
Figure 14A:
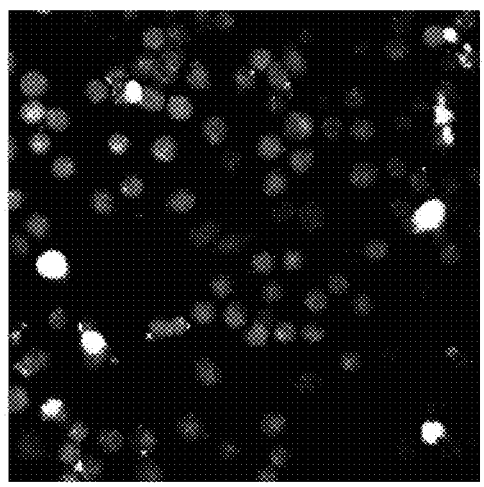
Figure 14B:
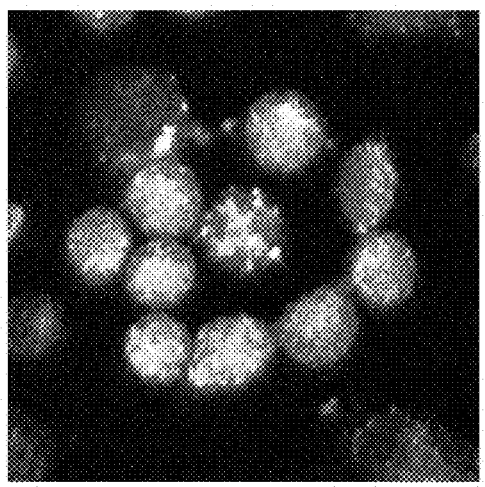
Figure 15:
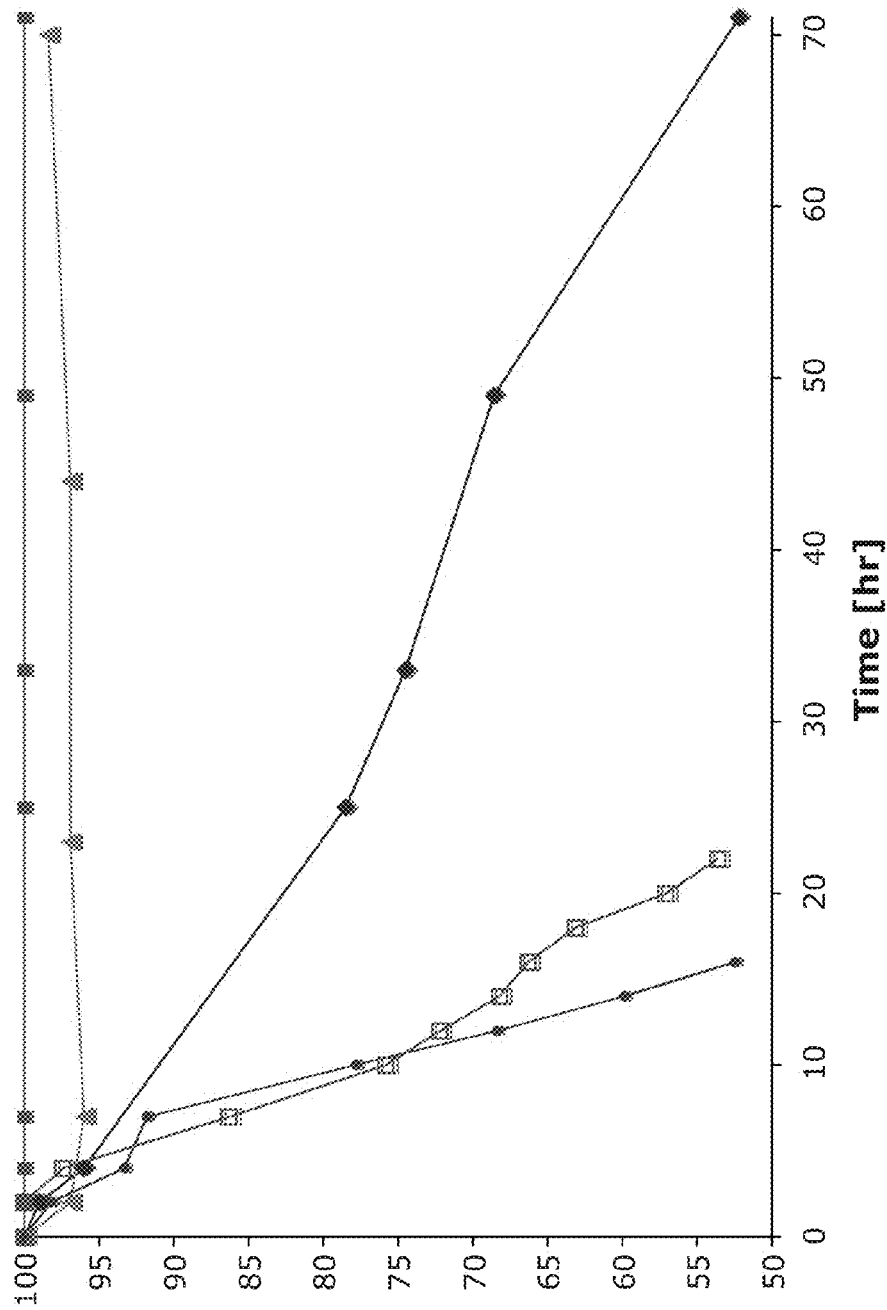
Figure 16:
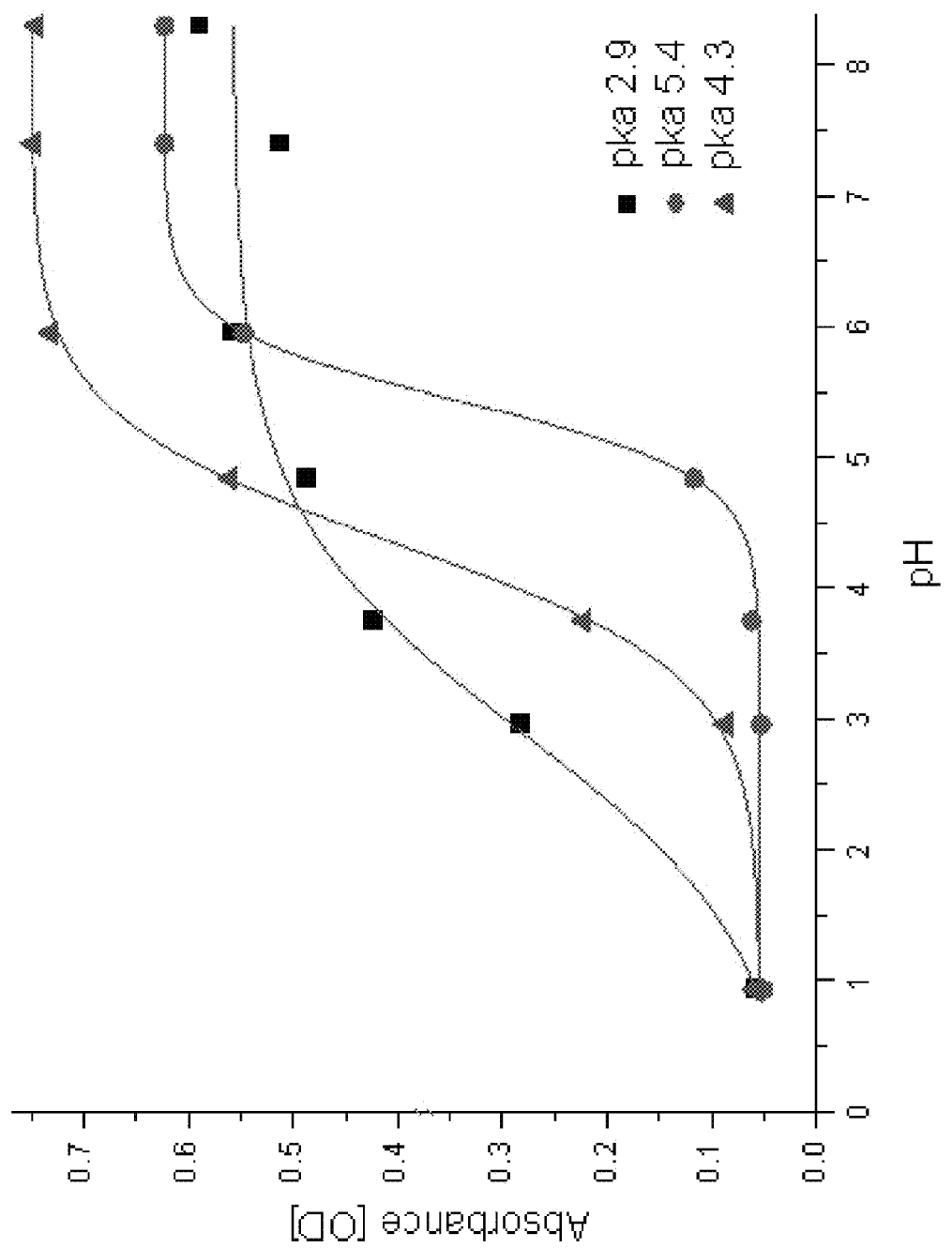
Figure 17A:
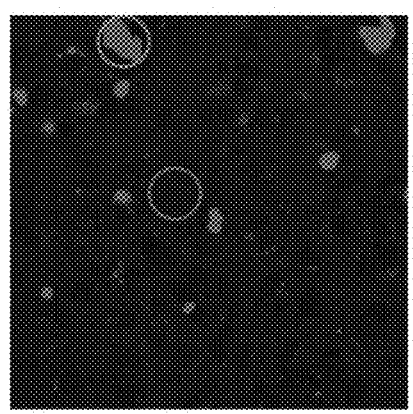
Figure 17B:
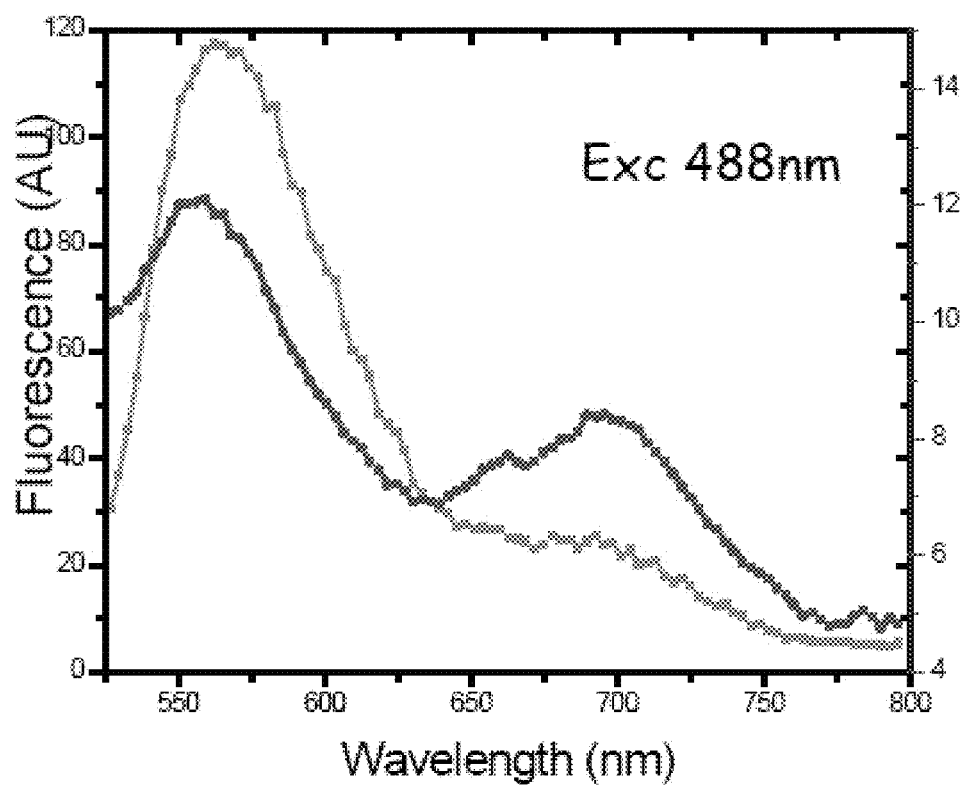
Figure 20A:
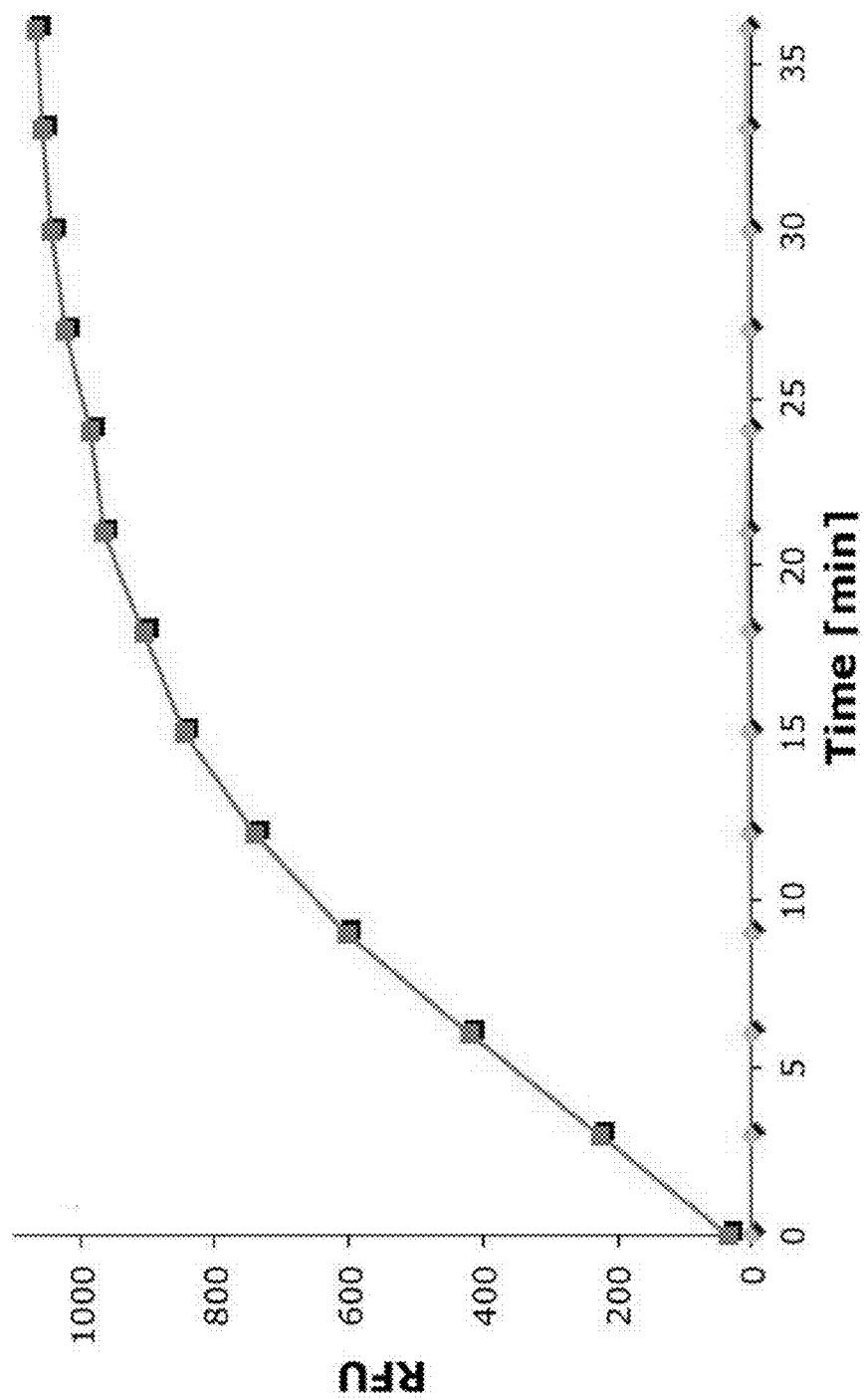
Figure 20B:
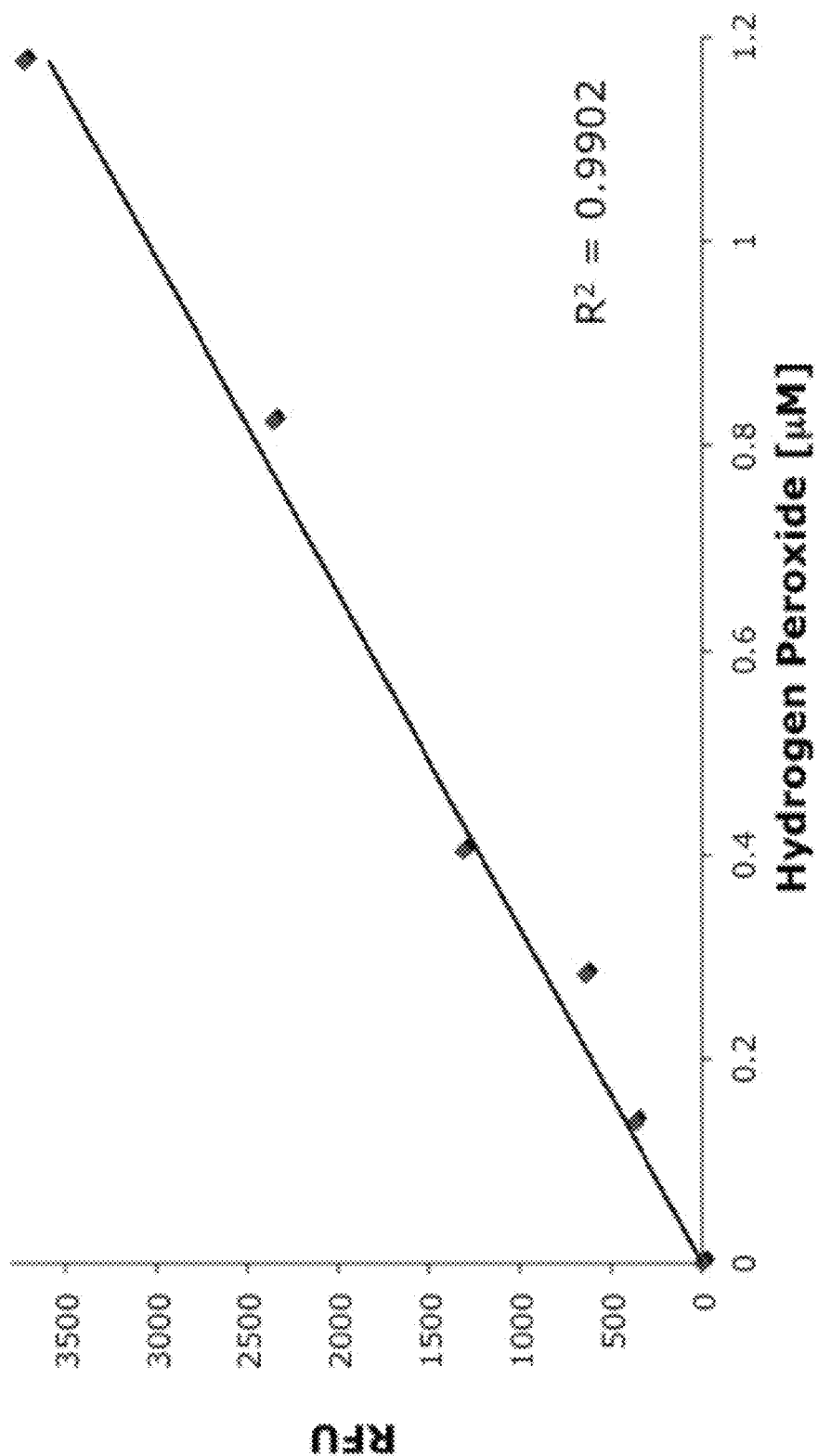
Figure 21:
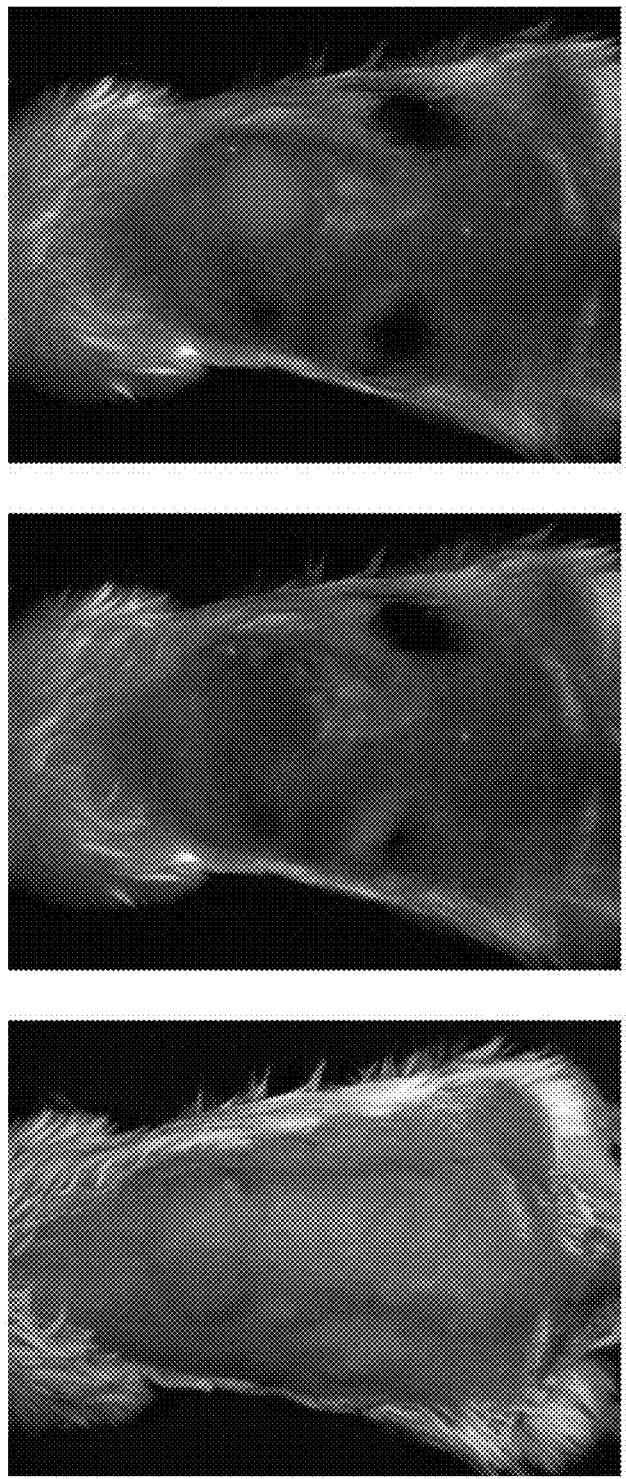
Figure 22:
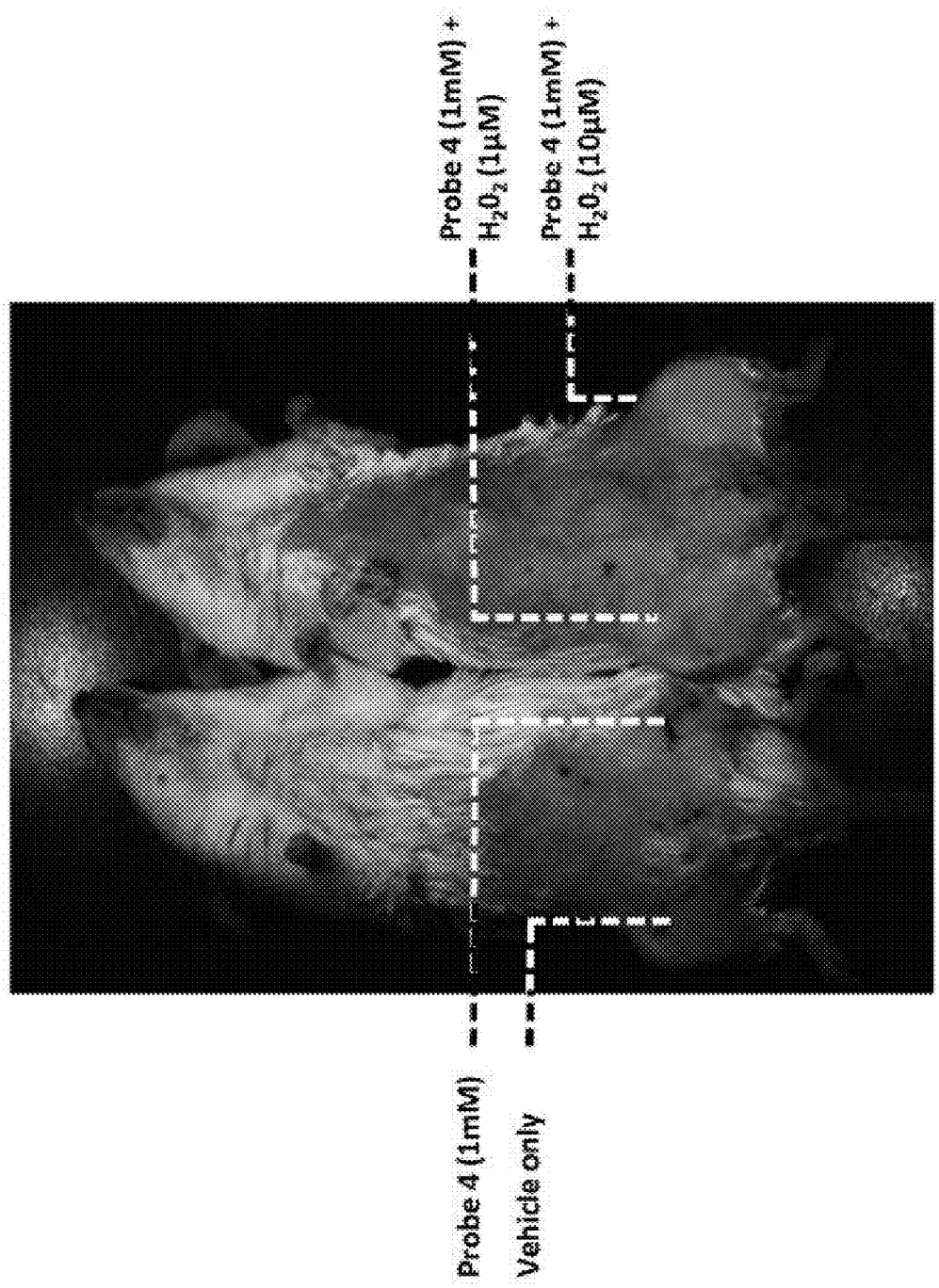
Figure 23A:
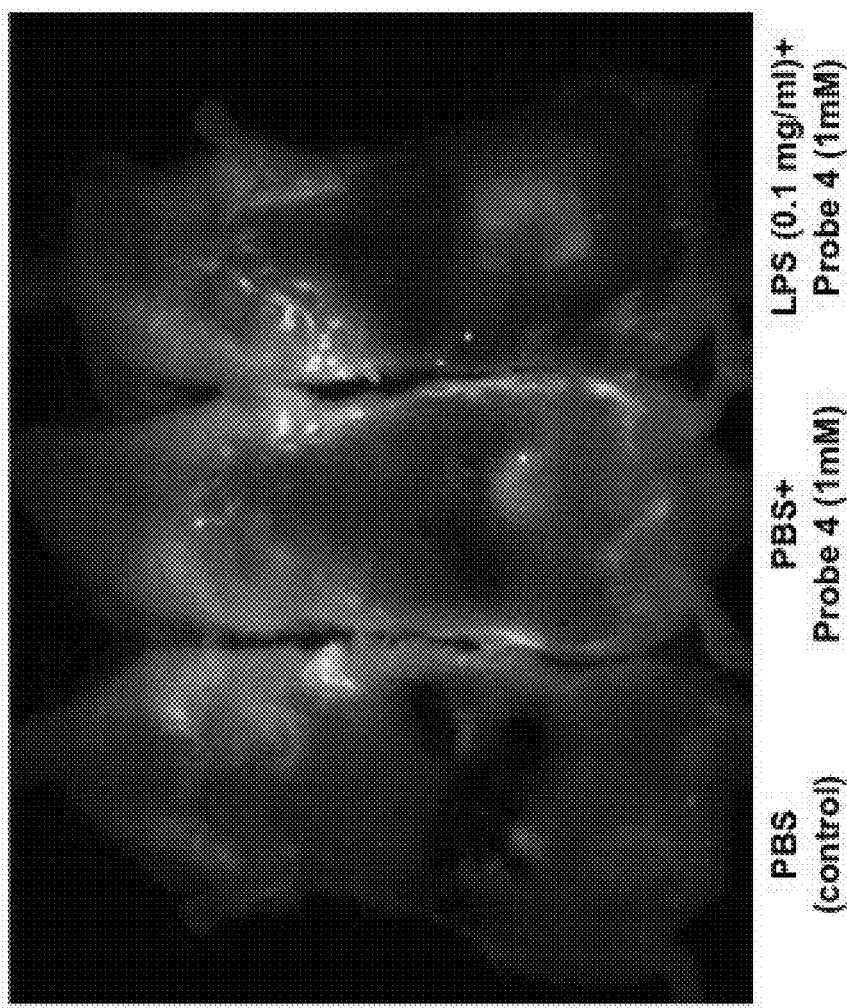
Figure 23B:
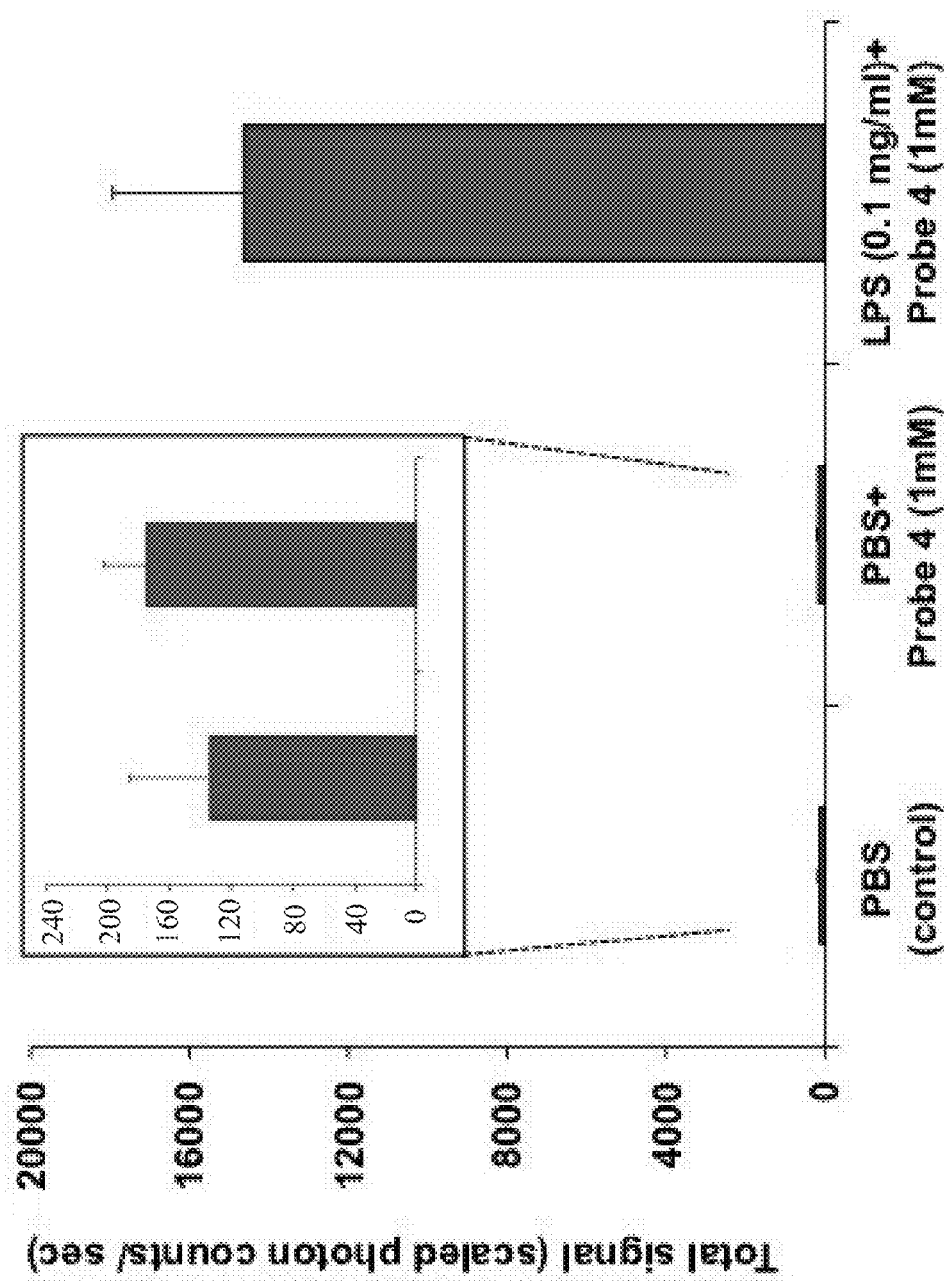
Figure 24A:
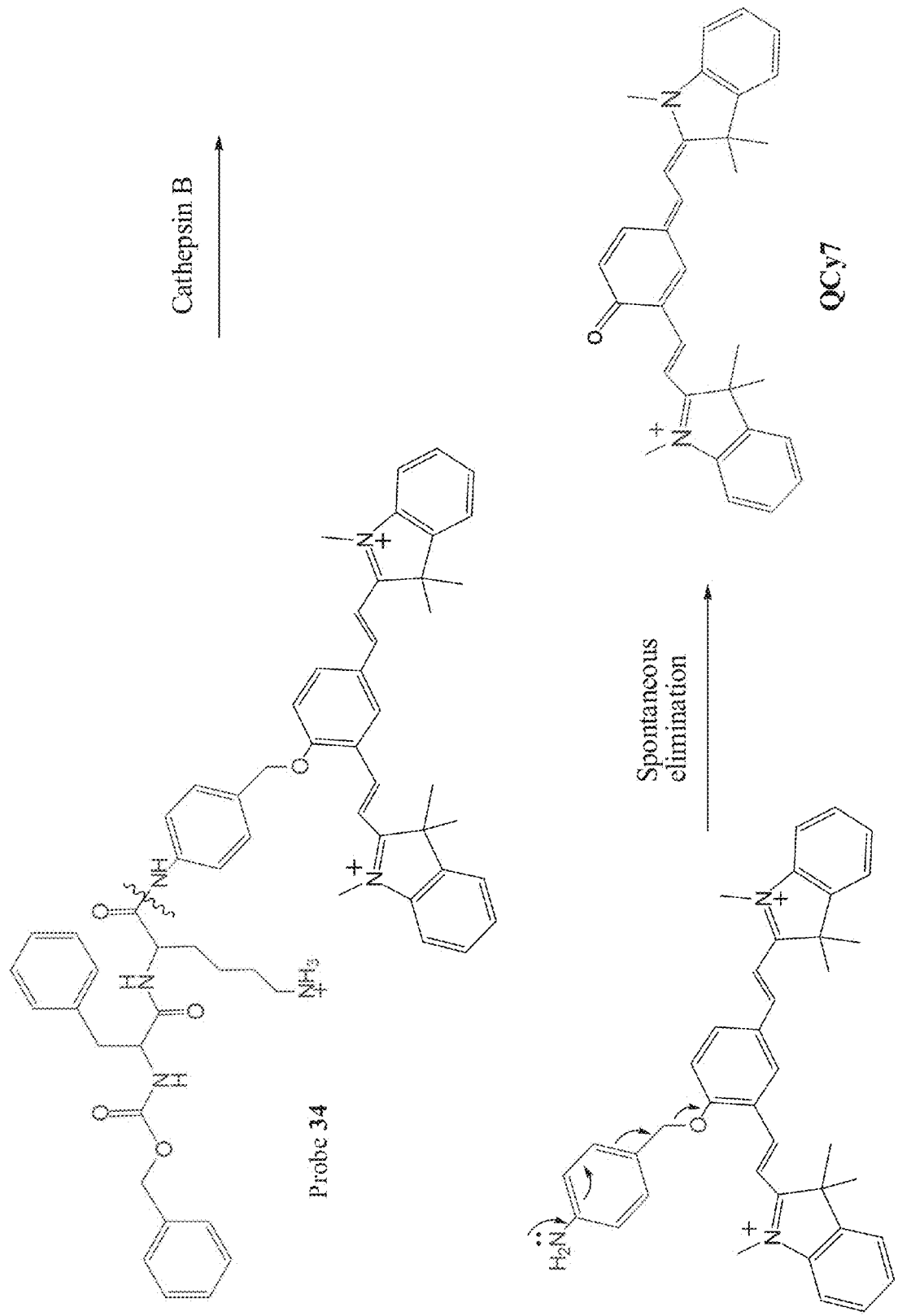
Figure 24B:
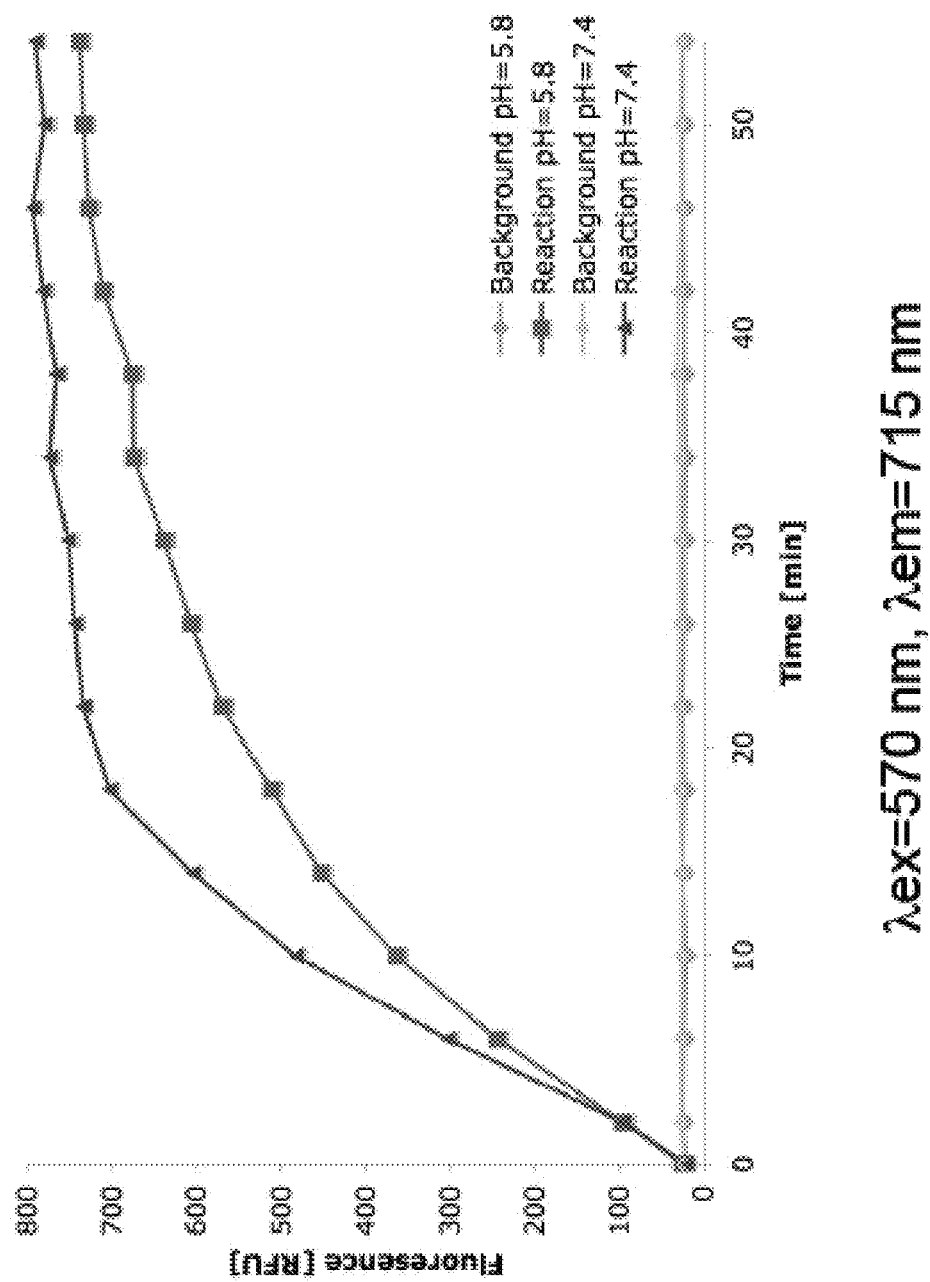
Figure 25:
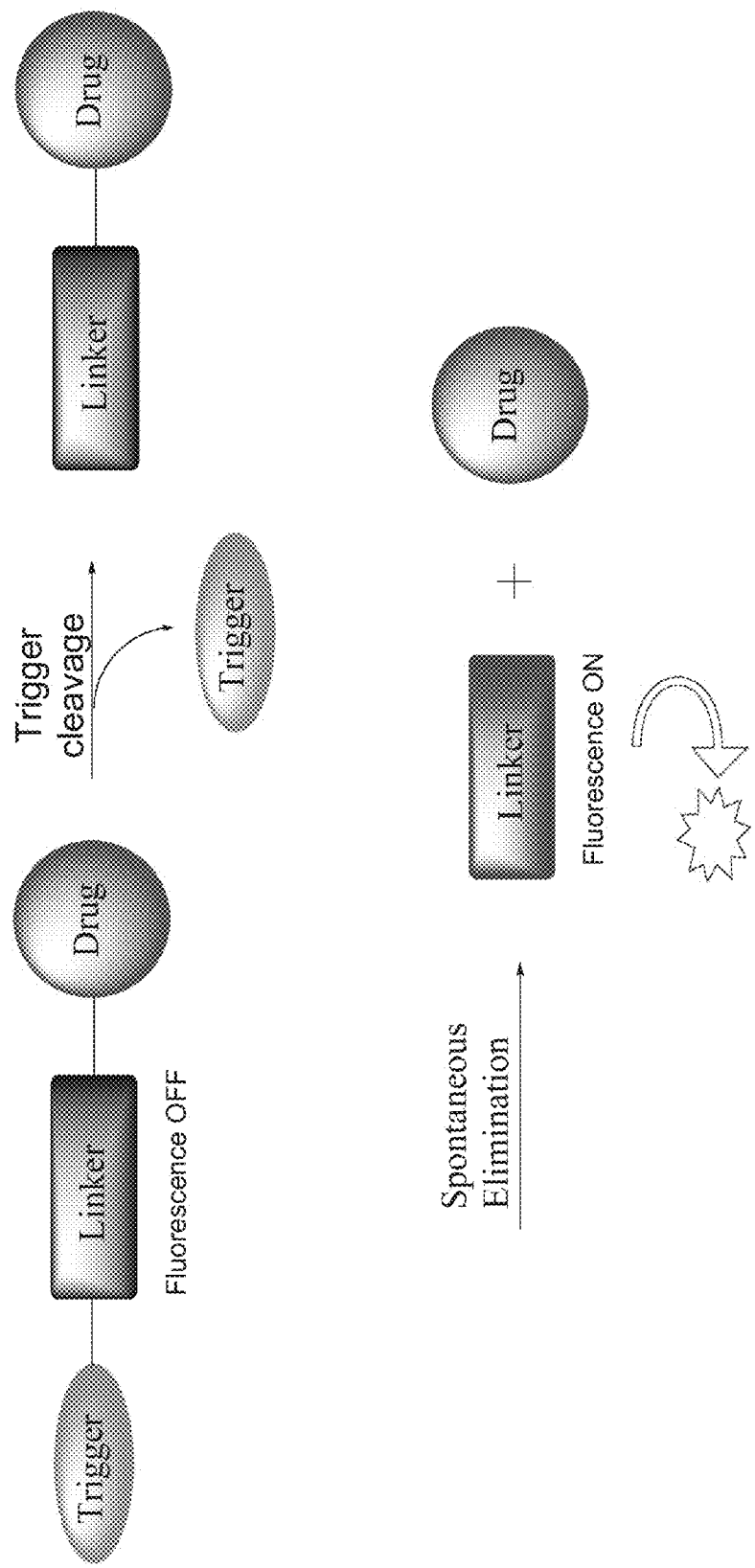
Figure 26:
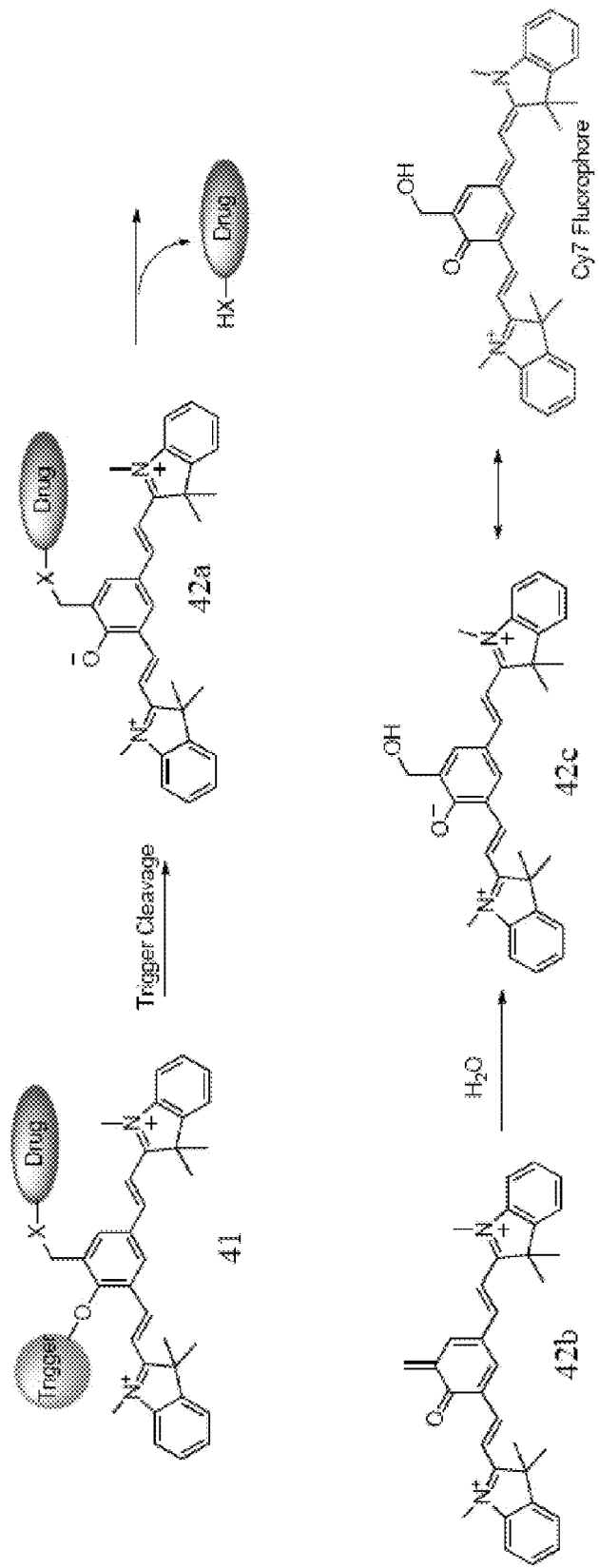
Figure 27:
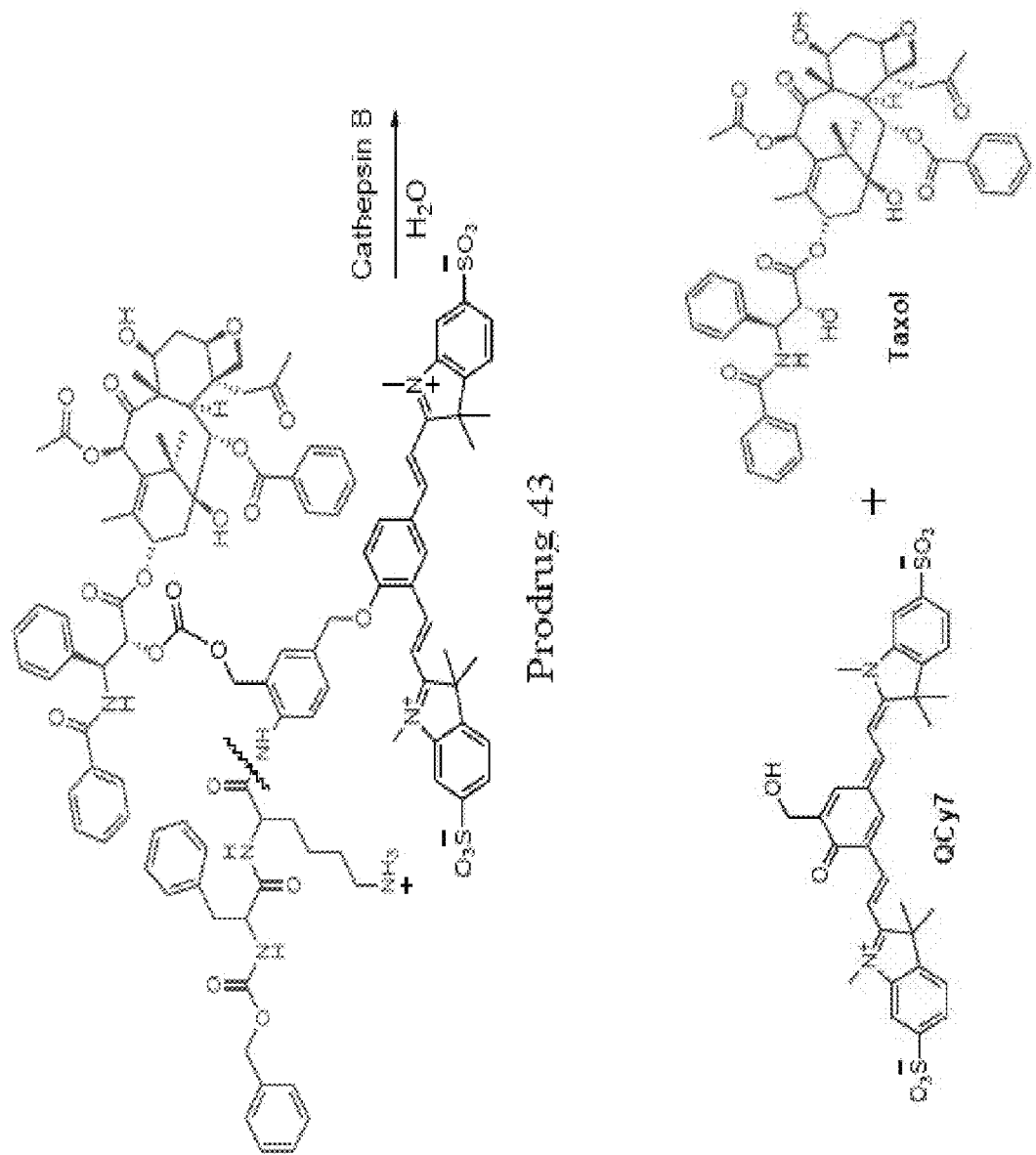
Figure 28:
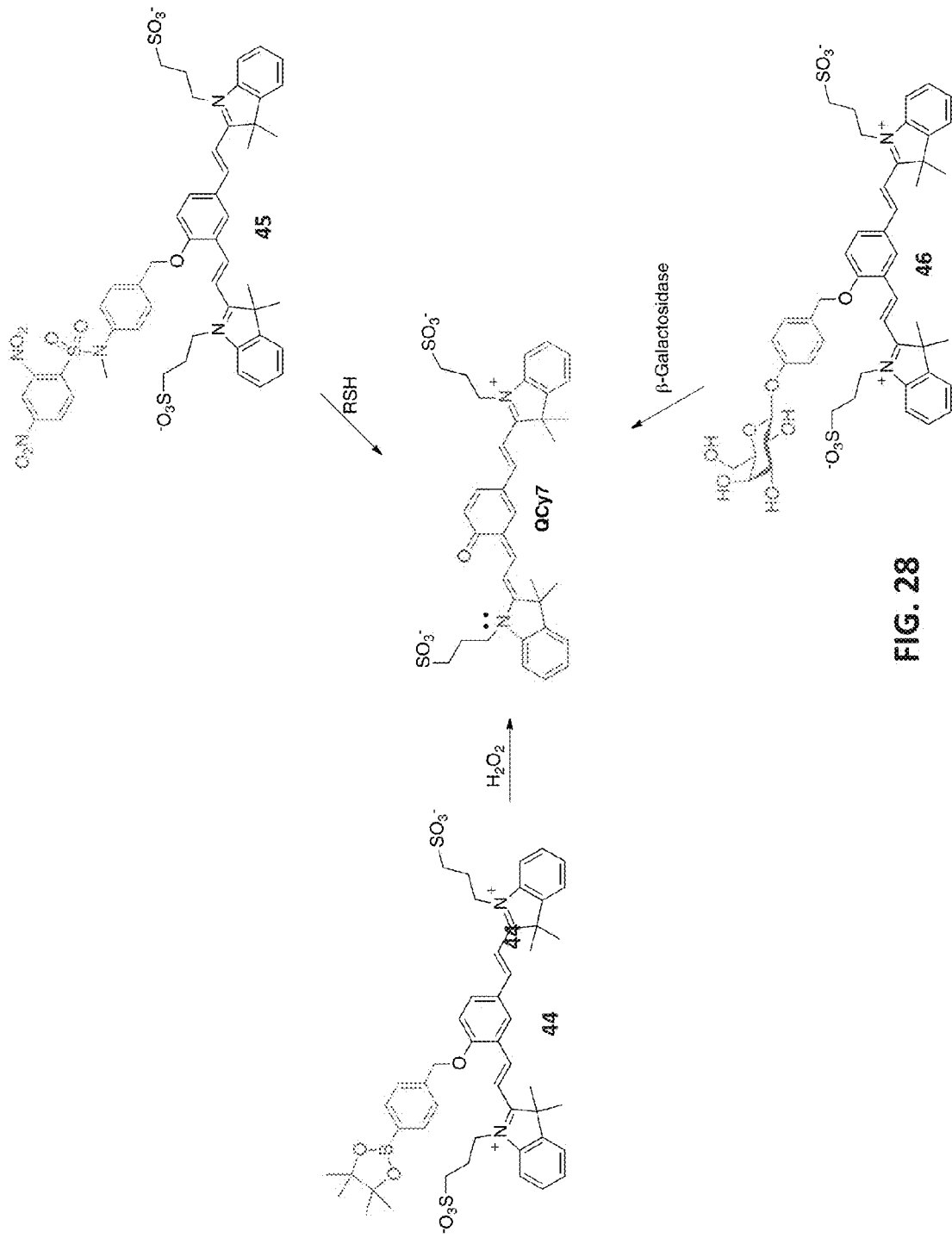

FIGS. 9A-B present linear plots of the fluorescence intensity vs. absorbance of QCy7 (FIG. 9A) and Sulfo-QCy7 (FIG. 9B);

FIG. 10 presents a linear plot of the absorbance of Sulfo-QCy7 as a function of its concentration in PBS 7.4, measured at 590 nm;

FIG. 11 presents the absorption (blue) and fluorescence (red) of Compound 14 (see, Table 1, Entry 6) in PBS 7.4 [50 µM];

FIG. 12 presents the absorption (blue) and fluorescence (red) of Compound 18 (Table 1, Entry 10) in PBS 7.4 [50 µM];

FIG. 13 presents the absorption (blue) and fluorescence (red) of Compound 25 (Table 1, Entry 21) in PBS 7.4 in PBS 7.4 [50 µM];

FIGS. 14A-B present images obtained by confocal microscopy upon 2-photon excitation at 930 nm, of HeLa cells incubated overnight with Compound 25 (Table 1, Entry 21);

FIG. 15 presents the normalized intensity of NIR fluorescent emission of dye compounds generated from Compound 9 (green circles), Compound 14 (blue diamonds), Compound 18 (red squares), Compound 25 (orange triangles) and of cyanine dye Cy7 (blank navy squares), as a function of incubation time in PBS 7.4, at 37° C. (25 µM);

FIG. 16 presents the UV-Vis absorbance as a function of the environment pH as measured for Compound 14 (black squares), Compound 18 (blue triangles) and Compound 25 (red circles) (50 µM in a buffer at the indicated pH);

FIGS. 17A-B present a confocal image (FIG. 17A) and plots (FIG. 17B) demonstrating the fluorescence of Sulfo-QCy7 (generated from Compound 9) inside (green) and outside (red) Hela cells;

FIGS. 18A-F present confocal imaging of HeLa cells showing images obtained in colocalization assay of Compound 25 with the lysosome marker lysosensor (FIGS. 18A-C) and confocal images of HeLa cells incubated overnight with Compound 25 (FIGS. 18D-F), upon excitation with a 561 nm laser line acquiring fluorescence from 570 nm to 800 nm;

FIGS. 19A-B are photographs of probe Compound 4 and of Compound 9 (generating sulfo-QCy7) in PBS 7.4 [50 µM] solutions (FIG. 19A) and of probe 4 and sulfo-QCy7 in PBS 7.4 [50 µM] solutions obtained by NIR camera (excitation at wavelength 570 nm, cutting filter of >690 nm) (FIG. 19B);

FIGS. 20A-B are graphs showing the NIR fluorescence ($\lambda_{Ex}$=590 nm, $\lambda_{Em}$=720 nm) emitted upon incubation of probe Compound 4 [50 µM] in the presence (red) and absence (blue) of hydrogen peroxide [50 µM] in PBS 7.4 at 37° C. (FIG. 20A) and the NIR fluorescence emitted of probe Compound 4 [100 µM] upon incubation with the indicated concentrations of hydrogen peroxide (FIG. 20B);

FIG. 21 presents in vivo imaging of exogenous hydrogen peroxide by probe Compound 4 (CRI Maestro™ image, Excitation at 595 nm, emission cutoff filter of 635 nm);

FIG. 22 presents probe Compound 4-fluorescence dependency on hydrogen peroxide concentration (CRI Maestro™ image. Excitation at 595 nm, emission cutoff filter of 635 nm);

FIGS. 23A-B present In vivo imaging of endogenous hydrogen peroxide in the peritoneal cavity of mice, during an LPS-induced inflammatory response, using probe Compound 4 (FIG. 234A) (Right mouse—LPS was injected into the peritoneal cavity of mice, followed 6 hours later by an intraperitoneal injection of probe 4; Middle mouse-PBS was injected into the peritoneal cavity of mice, followed 6 hours later by an intraperitoneal injection of probe 4; and Left mouse—The negative control (PBS only)), and a bar graph (FIG. 23B) showing the quantification of the NIR-fluorescence emission intensity from the two mice injected with probe Compound 4 in the presence or absence of LPS-induced inflammation (i.e. $H_2O_2$) (the total number of photons from the entire peritoneal cavity was integrated and plotted as a ratio compared with the control group (n=5), with the insert focusing on the NIR-fluorescence emission intensity obtained from injections of PBS (control) or probe 4 in absence of LPS-induced inflammation;

FIGS. 24A-B present a schematic illustration depicting the chemical structure of cathepsin B-activated Probe 34 and the generation of dye QCy7 upon enzymatic cleavage of Probe 34 in the presence of Cathepsin B (FIG. 24A) and comparative plots showing the NIR fluorescence of probe 34 emitted in the presence and absence of cathepsin B at the indicated pH;

FIG. 25 is a schematic illustration of a design for coupling latent fluorophore activation to monitor a drug-release event in a delivery system;

FIG. 26 is a schematic illustration of an exemplary disassembly mechanism of QCy7-based reporting drug delivery system;

FIG. 27 presents Cathepsin B-activated prodrug which generates NIR fluorescence by formation of sulfo-QCy7 and release of free taxi;

FIG. 28 presents a schematic illustration depicting the chemical structures and activation of exemplary QCy7-based probes for detection of hydrogen peroxide (Probe 44), ubiquitous sulfhydryl (Probe 45), and β-galactosidase (Probe 46), according to some embodiments of the present invention.

Figure 29C:
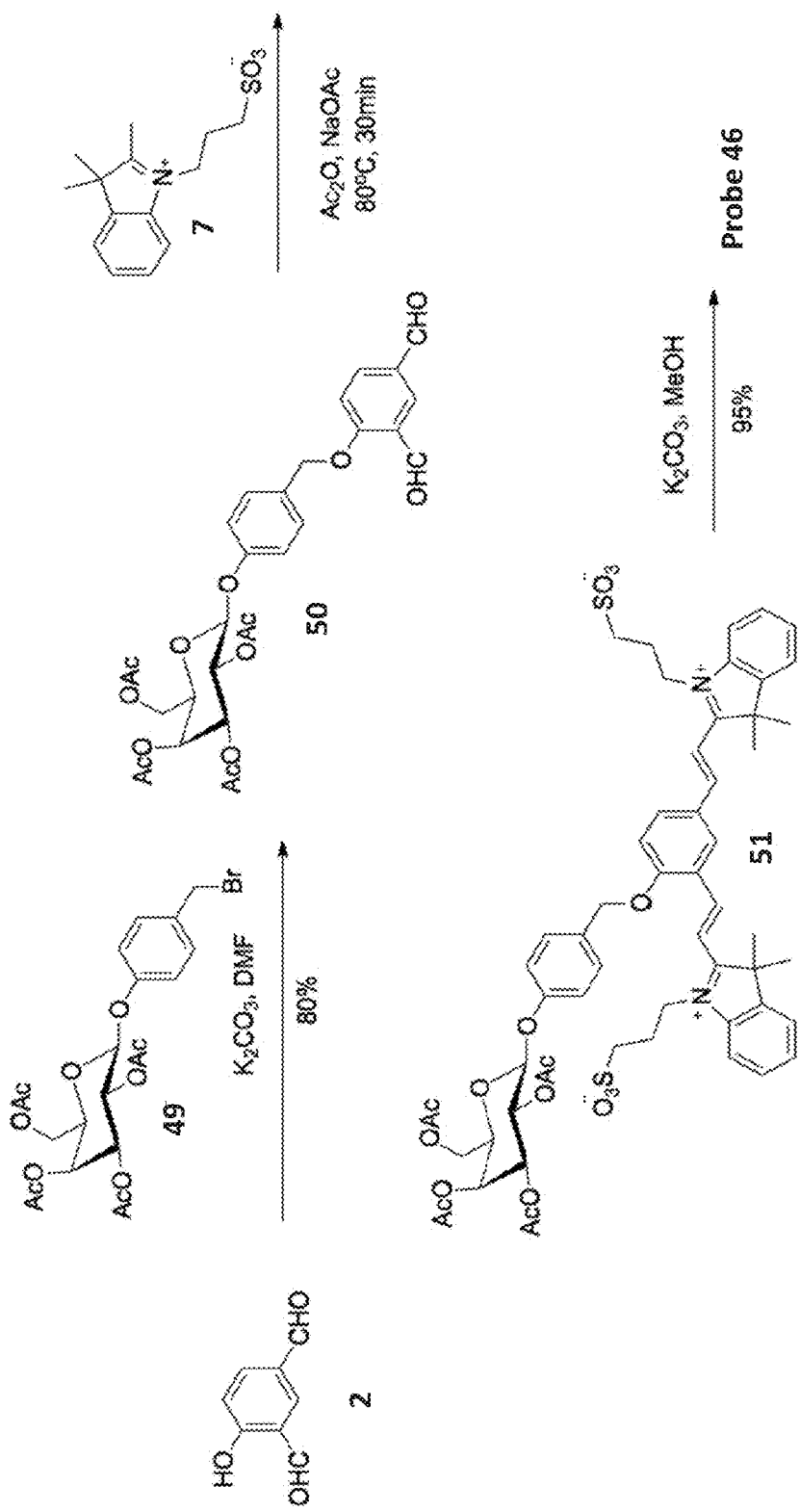
Figures 31A, 31B:
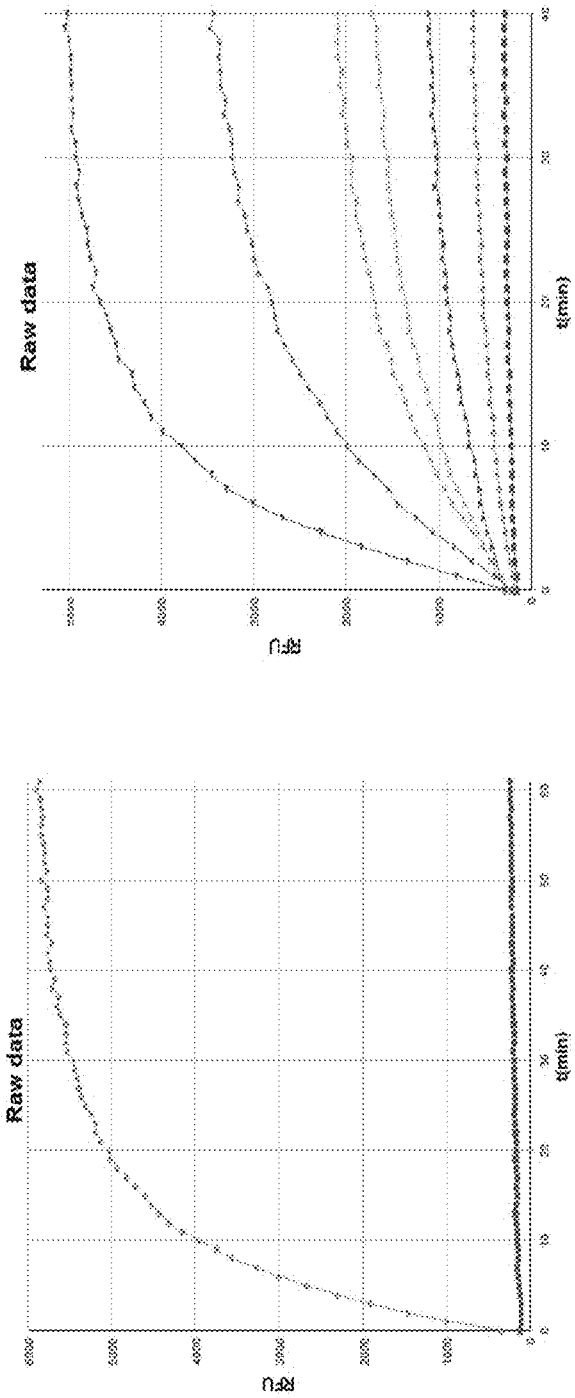
Figure 32B:
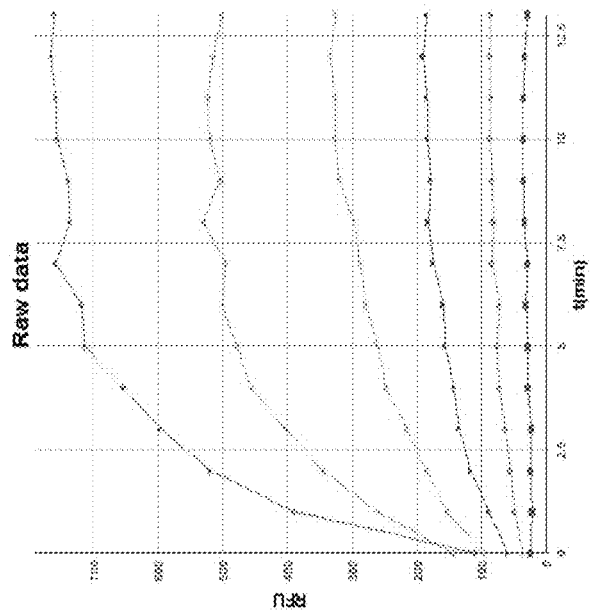
Figure 32A:
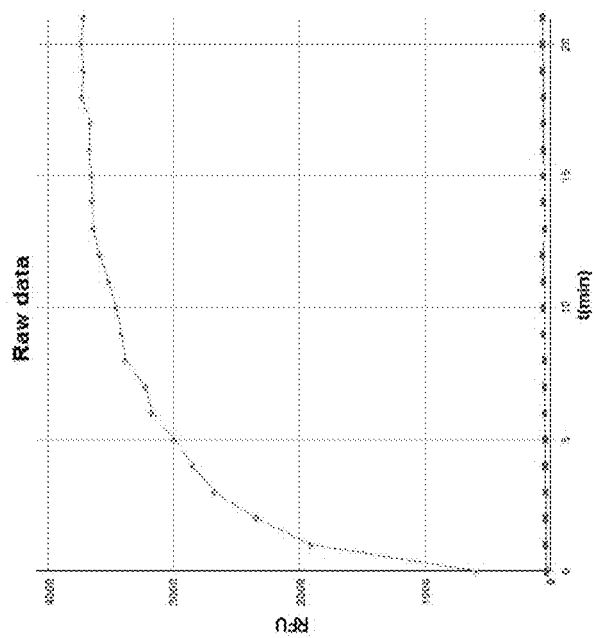
Figure 33B:
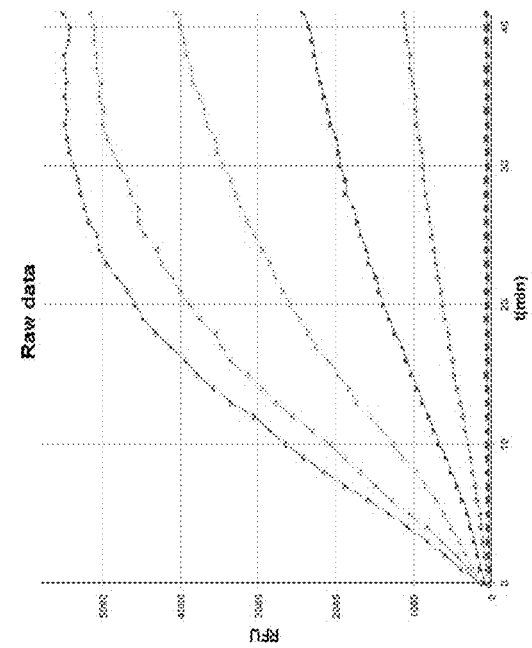
Figure 33A:
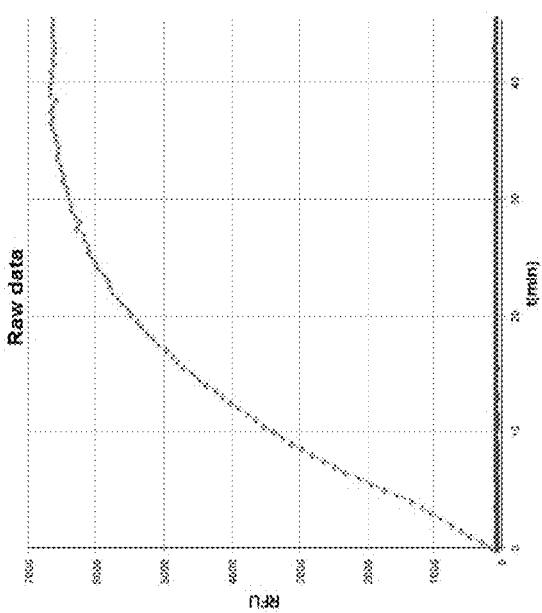

FIGS. 29A-C present schematic illustrations depicting the chemical syntheses of exemplary QCy7-based probes for detection of hydrogen peroxide (FIG. 29A; Probe 44), ubiquitous sulfhydryl (FIG. 29B, Probe 45), and β-galactosidase (FIG. 29C; Probe 46), according to some embodiments of the present invention;

FIGS. 30A-C present graphs showing the NIR fluorescence ($\lambda_{Ex}$=590 nm, $\lambda_{Em}$=720 nm) emitted upon incubation of Probe 44 [100 µM] with hydrogen peroxide (5 equivalents), 0, 3, 9, 15 and 40 minutes after addition of the hydrogen peroxide (FIG. 30A); upon incubation of Probe 45 [100 µM] with cysteine (1 equivalent) 0, 1, 3, 9 and 30 min after the addition of cysteine (FIG. 30B); and upon incubation of Probe 46 [100 µM] with 1.37 enzyme units of β-galactosidase, 0, 6, 18, 30, and 60 min after the addition of the enzyme (FIG. 30C); all in 1% DMSO, PBS, pH 7.4 medium;

FIGS. 31A-B present graphs showing the NIR Fluorescence (λex=590 nm, λem=720 nm) emitted upon incubation of probe 44 [100 µM], in the presence (green) or absence (red) of $H_2O_2$ (5 equivalents) in 1% DMSO in 0.1 M PBS, pH=7.4 (FIG. 31A), and the NIR Fluorescence (λex=590 nm, λem=720 nm) emitted upon incubation of probe 44 [100 µM] with 0, 10, 20, 30, 40, 70 and 100 µM $H_2O_2$, in 1% DMSO in 0.1 M PBS, pH=7.4 (FIG. 31B);

FIGS. 32A-B present graphs showing the NIR Fluorescence (λex=590 nm, λem=720 nm) emitted upon incubation of probe 45 [100 µM], in the presence (green) or absence (red) of cysteine (1 equivalent) in 1% DMSO in 0.1 M PBS, pH=7.4 (FIG. 32A), and the NIR Fluorescence (λex=590 nm, λem=720 nm) emitted upon incubation of probe 45 [100 µM] with 0.1, 2.5, 5, 10, 15, 20 M cysteine, in 1% DMSO in 0.1 M PBS, pH=7.4 (FIG. 31B);

FIGS. 33A-B present graphs showing the NIR Fluorescence (λex=590 nm, λem=720 nm) emitted upon incubation of probe 46 [100 µM], in the presence (green) or absence (red) of beta-galactosidase (1.37 units) in 1% DMSO in 0.1 M PBS, pH=7.4 (FIG. 33A), and the NIR Fluorescence (λex=590 nm, λem=720 nm) emitted upon incubation of probe 46 [100 µM] with 1.37, 0.91, 0.45, 0.22, 0.11 or 0 enzyme units, in 1% DMSO in 0.1 M PBS, pH=7.4 (FIG. 33B); and FIGS. 34A-C present photographs showing fluorescence of Probe 44 (FIG. 34A), Probe 45 (FIG. 34B) and Probe 46 (FIG. 34C), upon incubation of the probe [100 µM] in saline (pH 7) containing 0.1% DMSO, in the presence or absence of their corresponding analyte, as taken by regular camera (left) and NIR camera (middle), and showing intravital fluorescence of the probe [10 µM] as taken by CRI Maestro™ Imaging system with Filter set at excitation at 595 nm, and emission cut-off filter of 715 nm, upon subcutaneous injection into mice.

DESCRIPTION OF SPECIFIC EMBODIMENTS OF THE INVENTION

The present invention, in some embodiments thereof, relates to fluorogenic compounds and, more particularly, but not exclusively, to chemically-activatable fluorogenic compounds which upon a chemical event rearrange so as produce a near infrared probe, and to uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The development of highly sensitive fluorogenic probes in combination with innovative optical techniques is a promising strategy for intravital non-invasive qualitative and/or quantitative imaging.

As indicated hereinabove, for practicing methods that allow direct and reliable assessment of analytes in vivo, a water-soluble and NIR fluorescence-based probe having emission maxima between 650 and 900 nm is desirable. Because of their superior spectroscopic characteristics, cyanine dyes are considered as the main class of NIR fluorescent probes for biological applications, yet, their use is limited by failure to provide efficient cyanine-based probes with a Turn-ON mechanism.

The most efficient methodology for applying a Turn-ON mechanism to fluorogenic molecules is based on coupling a trigger moiety to the fluorogenic molecule via a functional group thereof. Such a masking of the functional group reduces the conjugated π-electron system of the dye and thus turns OFF the fluorescence of the probe. Removal of the trigger renews the conjugation of the functional group with the π-electrons of the dye and thereby turns ON the fluorescent signal of the probe, as depicted in Background Art FIG. 1.

However, while such a concept was mostly demonstrated for dyes with UV-V is fluorescence, such as coumarin, applying this turn-ON mechanism in cyanine dyes is difficult to perform. Cyanine dyes have a π-electron system composed of a polymethine bridge typically being 3 or more atoms in length, conjugated to unsaturated bonds of two indolenine-type rings, and therefore typically do not have any functional group which is conjugated to this π-electron system. Furthermore, since the π-electron system of the cyanine molecule is relatively long, the inclusion of an additional functional group in its π-system is not expected to influence the fluorescence spectrum as is the case in other common dyes. Similar limitations for practicing such a turn-ON mechanism are expected also with other near IR probes.

Indeed, only limited specific examples for cyanine probes that involve changes in the π-electrons conjugation have been reported.

The present inventors have now designed and successfully prepared and practiced a novel methodology for generation of a novel class of Turn-ON NIR cyanine-based probes, by introducing a Turn-ON mechanism in molecules with cyanine spectroscopic characteristics. The disclosed cyanine-based probes are designed to allow formation of a fluorescent cyanine molecule through π-electrons relocation, upon removal of a trigger unit by an appropriate analyte. The probe is based on novel cyanine-like fluorochromes, which are obtained upon removal of a trigger unit by the analyte of interest. A distinctive change of π-electrons system leads to generation of a cyanine dye with strong NIR fluorescence. The disclosed modular cyanine-based probe can release an active cyanine fluorochrome upon reaction with specific analyte and thus can be modularly derivatized and suitably adjusted for imaging of various analytes, by introducing an appropriate trigger unit. The synthesis of the disclosed probes is very simple can be modified as desired to prepare various probes for detection and imaging of various analytes.

The controllable spectral characteristics of the cyanine dyes, as recognized in the art, can also be utilized according to some embodiments of the present invention. These spectral characteristics have been observed to follow specific empirical rules. For example, each additional conjugated double bond between the amino donor and the ammonium acceptor will raise the absorption and emission maximum by about 100 nm. Thus, when a compound with n=1 has a maximum absorption of approximately 550 nm, equivalent compounds with n=2 and n=3 will have maximum absorptions of 650 nm and 750 nm respectively. Addition of aromatic groups to the sides of the molecules can shift the absorption by 15 nm to a longer wavelength. The groups comprising the nitrogen-containing donor and acceptor moieties and the substituents thereof can also contribute to the absorption and emission characteristics. Using the values obtained with gem-dimethyl group as a reference point, oxygen substituted in the ring for the gem-dimethyl group decreases the absorption and emission maxima by approximately 50 nm. In contrast, substitution of sulfur increases the absorption and emission maxima by about 25 nm. R groups on the aromatic rings such as alkyl, alkyl-sulfonate and alkyl-carboxylate have little effect on the absorption and emission maxima of the cyanine dyes (see, for example, U.S. Pat. No. 6,110,630).

As demonstrated in the Examples section that follows, exemplary Turn-ON NIR cyanine-based probes have been successfully synthesized through a simple two-step procedure and exhibited relatively high quantum yield and large extinction coefficient. Exemplary Turn-ON probes were applied to demonstrate non-invasive in vivo imaging of endogenously produced hydrogen peroxide in an acute inflammation model in mice.

The novel class of Turn-ON NIR cyanine-based probes disclosed herein can straightforwardly be utilized as research tools for in vitro applications such as, but not limited to, cellular uptake, trafficking and proof of concept related to presence and/or levels of a substance that activates the fluorescent system (e.g., enzymes), and importantly, for in vivo imaging and monitoring of biological processes such as the presence and/or progression of diseases and disorders such as cancer and inflammation. For example, the novel class of Turn-ON NIR cyanine-based probes disclosed herein can be utilized for early detection of cancer in patients and for non-invasively monitoring cancer progression and efficacy of treatment.

FIG. 1B describes a schematic illustration of the general concept underlying some embodiments of the present invention, in which rearrangement of the structure of a fluorogenic compound results in electron transfer between the moieties composing exemplary fluorogenic probes, as detailed hereinbelow, such that the relocation of π-electrons generates fluorescent compounds.

FIGS. 2A-H and 28 present exemplary designs of Turn-ON NIR cyanine-based probes according to some embodiments of the present invention. A functional group that generates a phenolate anion upon chemical activation is incorporated within or attached to a polymethine chain or a carbomethine-containing moiety of a cyanine-like molecule. The incorporation of the functional group results in a molecule with two positive charges, and thus prevents delocalization of the positive charge between the two nitrogen-containing moieties (e.g., the indolenine rings), as in the case of typical cyanine molecules (e.g., Cy7 presented in FIG. 2A), such that NIR fluorescence is OFF. Upon generation of a phenolate anion, due to e.g., deprotonation or cleavage of a trigger unit, delocalization of the positive charge is enabled, via a resonance hybrid that has a similar conjugation pattern to that of cyanine. As a result, the NIR fluorescence of the probe is switched to ON position.

FIGS. 3A-B and 29A-B present exemplary general synthetic pathways for generating exemplary fluorogenic compounds according to some embodiments of the present invention, and exemplary acceptor moieties suitable for use in these pathways, demonstrating the modularity of the methodology described herein, and further showing the generation of fluorescent compounds therefrom.

FIGS. 4-13 and 30-33 present the spectral characteristics of exemplary fluorogenic compounds according to some embodiments of the present invention.

FIGS. 14-18 present data of the stability, acidity, cell permeability and fluorescence of exemplary compounds according to some embodiments of the present invention.

FIGS. 19-23 present in vitro and in vivo data obtained with an exemplary hydrogen peroxide-sensitive probe according to some embodiments of the present invention, in an acute inflammation model in mice.

FIGS. 24A-B present design and practice of cathepsin B-activated probe according to some embodiments of the present invention.

FIGS. 25-27 demonstrate exemplary designs in which turn-ON NIR probe is implemented in a prodrug system, which can be useful, for example, to obtain a real-time reporting mode of action of a drug. A drug molecule is linked to the cyanine-based probe through a releasable bond so as to generate a prodrug system with OFF NIR fluorescence. Removal of probe's trigger results in release of the free drug and formation of an active cyanine molecule with ON NIR fluorescence. Consequently, the prodrug activation is reported through generation of NIR fluorescence.

The design of cyanine-based probe structures with a Turn-ON mechanism demonstrated in the Examples section that follows, can be adopted for forming versatile systems in which π-electrons relocation is effected upon a chemical event and in which the π-electrons relocation results in capability of emitting NIR light.

FIGS. 34A-C present in vitro and in vivo data obtained with exemplary probes according to some embodiments of the present invention.

The Fluorogenic Compounds:

Accordingly, according to an aspect of some embodiments of the present invention, there are provided fluorogenic compounds, each comprising two or more acceptor-containing moieties, e.g., a first and a second acceptor-containing moieties, and a donor-containing moiety, arranged such that said acceptor-containing moieties and said donor-containing moiety form a conjugated π-electron system devoid of resonating (delocalized) electrons between the acceptor-containing moieties. The donor-containing moiety and the two or more acceptor-containing moieties, however, are arranged such that upon a chemical event, the donor-containing moiety rearranges so as to transfer π-electrons to one of the acceptor-containing moieties (e.g., to a first acceptor moiety) and, as a result of the relocalization of the π-electrons, one of the acceptor-containing moieties becomes a donor-containing moiety and a π-electron system in which π-electrons resonate between the newly-formed donor-containing moiety and the remaining acceptor-containing moiety or moieties, is generated.

Due to the electronic structure of the fluorogenic compounds, in which delocalization of π-electrons between the acceptor-containing moieties is restricted, the compound is spectroscopically inactive (or has weak spectroscopic properties), at least in the NIR range, and thus is incapable of emitting light, particularly, near infrared light. Nonetheless, the arrangement of the donor-containing moiety and the acceptor-containing moieties allows to induce relocalization of the π-electrons by a chemical event, a relocalization that results in spectroscopic activity in the NIR range, namely, a capability to emit near infrared light.

The relocalization of the π-electrons by the chemical event involves electronic rearrangement of the donor-containing moiety in the compound, in which electrons are transferred to one of the acceptor-containing moieties, and render this acceptor-containing moiety a donor moiety with respect to the other acceptor-containing moiety or moieties. As a result, a π-electron system with delocalized, resonating electrons between the remaining acceptor-containing moiety or moieties and the newly-formed donor-containing moiety (previously another acceptor-containing moiety) is formed and near infrared spectroscopic properties are imparted.

As generally stated in the art, the term "fluorogenic" encompasses a state or condition of having the capability to be fluorescent (i.e. to absorb and emit light, as defined hereinbelow) following a chemical, biochemical or physical occurrence or event. Thus, a "fluorogenic compound" describes a non-fluorescent compound or a weakly fluorescent compound that becomes more fluorescent (e.g., by at least 10%, at least 20%, at least 30%, at least 40%, at least 50%, at least 60%, at least 70%, at least 80%, at least 90 5, at least 100% (at least 2-fold), optionally at least 3-fold, optionally at least 4-fold more fluorescent, and optionally at 10-fold or higher more fluorescent) upon the occurrence of a chemical, biochemical or physical event. Accordingly, the phrase "chemically-activatable fluorogenic compound" as used herein describes a compound which is non-fluorescent (i.e., does not absorb and emit light) or which has weak fluorescence (e.g., have a quantum yield lower by at least 2-fold than a quantum yield of a corresponding fluorescent molecule with the strong fluorescence), and which becomes more fluorescent, as defined herein, upon a chemical event.

As used herein, a "chemical event" describes an event that involves a change in the chemical structure of a compound, including, but not limited to, bond cleavage, bond formation, protonation, deprotonation, oxidation, reduction, and more.

The chemical event can be a result of the presence or absence of a reagent which leads to the above-indicated changes in the chemical structure of the compound, a result of an environmental change (e.g., a change in pH or temperature or application of potential or irradiation), or a result of a presence or absence of a biological substance (e.g., an enzyme, a metalloprotein, a metal ion, etc.) which catalyzes a chemical reaction that leads to the change in the chemical structure.

In some embodiments, the chemical event is a result of the presence or absence of an analyte, as described in detail hereinbelow.

The phrase "fluorogenic compound" as used herein therefore describes a compound which changes its fluorescence upon a chemical event, and is therefore regarded, and in also referred to herein interchangeably, as a chemically-activatable fluorogneic compound, as a probe, as a chemically-activatable probe or as a Turn-ON probe. The fluorogenic compounds described herein throughout are also referred to in the context of the fluorescent compounds generated upon activation, as compounds generating the respective fluorescent (or dye) compounds disclosed herein.

The phrase "Turn-ON probe", which is also referred to herein interchangeably as a "probe with a Turn-ON mechanism" describes a fluorogenic compound, which upon a chemical event, becomes fluorescent, as defined herein. In the fluorogenic compound, fluorescence is OFF, yet, the compound is designed such that upon being subjected to a chemical event, fluorescence turns ON.

Currently known NIR probes do not have efficient Turn-On mechanism, from reasons referred to hereinabove.

The phrase "fluorescent" refers to a compound that emits light upon return to the base state from a singlet excitation. The fluorescent compounds disclosed herein are also referred to herein throughout as dye compounds or dye molecules or as fluorophores or as fluorchromes.

In some embodiments, the fluorogenic compounds described herein are such that upon a chemical event, a molecule that is capable of emitting light (e.g., a fluorescent molecule) is formed.

In some embodiments, the emitted light is a near infrared light (near IR or NIR), being in the range of from about 700 nm to about 1400 nm. In some embodiments, the emitted light has emission maxima at a wavelength that is suitable for biological applications (e.g., in vivo applications), which ranges from 650 nm to 900 nm, and in some embodiments, from 700 nm to 800 nm.

Thus, a fluorogenic compound as disclosed herein does not exhibit fluorescence and hence does not emit light at a near infrared range, for example, a light having a wavelength in the range of from about 650 nm to about 900 nm, and is designed such that it is capable of exhibiting fluorescence and thus of emitting light at such a near infrared range upon a chemical event.

As used herein, reference to conjugation of a $\pi$-electrons system describes a system in which there is an overlap between at least two p-orbitals across an intervening sigma bond. The overlapping p-orbitals allow delocalization of $\pi$ electrons thereacross such that the $\pi$ electrons do not "belong" to a single atom or bond but are "distributed" over a group of atoms. A conjugated system with delocalized $\pi$-electrons generally lowers the energy of a molecule containing the same. The larger is the number of atoms that participate in the conjugation, the higher is the delocalization of the $\pi$-electrons, and the lower is the energy.

As used herein, reference to "resonance" describes a situation where delocalization of $\pi$-electrons occurs between two or more atoms in a molecule with conjugated $\pi$-electrons system, such that the molecule is represented by several contributing structures. "Resonating electrons" describe a situation where delocalization of $\pi$-electrons occurs such that in each contributing structure, a positive and/or negative charge is present on a different atom. When the phrase "resonating electrons" relates to certain atoms or group of atoms in a conjugated molecule, it is meant that overlapping p-orbitals exist throughout between these atoms or group of atoms and that in at least some contributing structures, each of these atoms or group of atoms has a different charge.

In the context of the present embodiments, a conjugated $\pi$-electrons system with no resonating electrons between the acceptor-containing moieties is thus used to describe delocalization of $\pi$-electrons through a reduced number of overlapping p-orbitals than a conjugated $\pi$-electrons system with resonating electrons between an acceptor-containing moiety and a donor-containing moiety, is accordance with the described-above features of the fluorogenic compounds.

As used herein, the phrase "acceptor-containing moiety" describes a moiety that comprises an acceptor group, whereby an "acceptor group" describes a group that has an electronic structure that allows transferring thereto electrons.

Typically, an acceptor group is an electron-withdrawing group.

The phrase "electron-withdrawing group", as used herein, generally refers to a chemical group in a molecule, which can draw electrons away from another part of the molecule. The distance over which the electron-withdrawing group can exert its effect, namely the number of bonds over which the electron-withdrawing effect spans, can be extended by conjugated $\pi$-electron systems. Non-limiting examples of suitable electron-withdrawing groups include, but are not limited to, nitro, ammonium ions (positively charged amino cations, including pyridinium ions, indolium ions, indolinium ions, picolinium ions), carboxy-containing groups, sulfonate, sulfate, nitrile, and trihaoalkyls, as these terms are defined herein.

Carboxy-containing groups include groups having a —C(=O) moiety, including acyl halides (a —C(=O)X group wherein X is halide), carbonyls, carboxylates, amides and aldehydes.

The acceptor group can be included in the acceptor-containing moiety as a substituent of, for example, an alkyl, an alkenyl, a cycloalkyl, an aryl or a heteroaryl, with aryls and heteroaryls being preferred due to their capability to participate in the π electrons conjugation. Optionally and preferably, the acceptor group is included within the backbone (skeleton) of an aromatic acceptor-containing moiety, forming an aryl or a heteroaryl.

For example, a nitro acceptor group can form a part of an oxy-pyridine. An ammonium acceptor group can form a part of an indolenine, or of any other nitrogen-containing heteroaromatic or heteroalicyclic. In one example, an ammonium acceptor forms a part of indolenine. In one example, an ammonium acceptor forms a part of pyridine such as N-alkyl pyridine (e.g., N-methyl-pyridine). A carbonyl can form a part of an unsaturated lactone or lactame. Exemplary acceptor groups that are suitable for being incorporated in the fluorogenic compounds described herein are presented in FIG. 3B.

As used herein, the phrase "donor-containing moiety" describes a moiety that comprises an electron donating group, whereby "an electron donating group" is a chemical entity that transfers electrons to another part of the molecule. The distance over which the electron-donating group can exert its effect, namely the number of bonds over which the electron-donating effect spans, can be extended by conjugated pi-electron systems. Non-limiting examples of electron-donating groups include, but are not limited to, groups that contain oxygen, nitrogen or sulfur atoms, such as hydroxyl, alkoxy, thiol, thioalkoxy, and amine, as these terms are defined herein.

In some embodiments, the donor-containing moiety is such that upon the chemical event, it rearranges by undergoing 1,4-quinonemethidine-like rearrangement. An exemplary such rearrangement is depicted in FIG. 2.

A "1,4-quinonemethidine" rearrangement involves electronic rearrangement of a phenolic moiety to form a quinone having a methide (=CH—) substituent at position 4 thereof.

A "1,4-quinonemethidine-like" rearrangement similarly involves rearrangement of aromatic moieties that contain donating groups other than hydroxyl, as defined herein, in which electron are transferred from the donating group to form a methide group at position 4 thereof.

Thus, in some embodiments the donor-containing moiety comprises an aromatic moiety. In some embodiments, the donor-containing moiety comprises an aromatic moiety with an electron donating substituent at a position, with respect to the other components of the molecule, that allows a 1,4-quinonemethidine-like rearrangement to take place as desired, namely, to result in an electron transfer to one of the acceptor-containing moieties and in an overall structure of the compound that allows electron resonance.

In some embodiments, the donor-containing moiety comprises an aromatic moiety substituted by hydroxyl, alkoxy, thiol and/or thioalkoxy. In some embodiments, the donor-containing moiety comprises an aromatic moiety substituted by hydroxyl.

In some embodiments, a fluorogenic compounds as described herein comprises two or more acceptor-containing moieties, at least one, and preferably all, comprising the same or different ammonium groups as described herein (e.g., indolinium group, indolium group, or pyridinium group as in picolinium), and donor-containing moiety that comprises an aryl (e.g., phenyl) substituted by hydroxyl (e.g., phenol), and which is linked to the acceptor-containing moieties such that a 1,4-elimination can be effected upon a chemical event, as described herein.

In some embodiments, the compound further comprises one or more linking moieties, linking the acceptor-containing moieties and the donor-containing moiety to one another. The linking moieties are such that participate in the conjugated π-electron system as defined.

In some embodiments, the linking moiety connects at least one, and preferably each, of the acceptor-containing moieties to the donor-containing moiety.

The length and chemical nature of the one or more linking moieties may affect the spectroscopic properties of the probe and are thus selected so as to impart the compound with spectroscopic characteristics as defined herein (namely, to be capable of emitting NIR light upon a chemical event).

In some embodiments, the one or more linking moieties comprise one or more carbomethine moieties, which can be collectively represented as —CR'=CR"— moieties, and which form the required conjugated π-electron system.

Any of the linking moieties as described herein can be used in combination with any of the acceptor-containing moieties and the donor-containing moieties as described herein.

In some embodiments, the fluorogenic compound comprises two acceptor-containing moieties, such that the compound is a donor-two-acceptors compound.

In some embodiments, the fluorogenic compound comprises three acceptor-containing moieties such that the compound is a donor-three-acceptors compound.

The chemically-activatable fluorogenic compounds disclosed herein can be collectively represented by the following general Formula I:

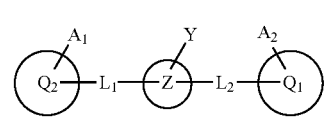

Formula I wherein:

$Q_1$ and $Q_2$ are each independently an acceptor-containing moiety, as defined herein;

$A_1$ and $A_2$ are each an acceptor group, as defined herein, in the acceptor-containing moieties;

Z and Y form the donor-containing moiety, as defined herein; and $L_2$ and $L_2$ are each independently a linking moiety or absent, and are each such that the $Q_1$ and $Q_2$ acceptor-containing moieties and the Z—Y donor containing moiety form the conjugated π-electron system, as defined herein.

In some embodiments, one or more of the acceptor-containing moieties includes an ammonium as an acceptor and hence comprises a =N⁺RaRb moiety, wherein Ra and Rb are each independently hydrogen, alkyl, aryl or cycloalkyl or, alternatively, Ra and Rb form together a heteroalicyclic or a heteroaryl.

Exemplary acceptor-containing moieties include, but are not limited to, ammonium ions derived from phenylamine, diphenylamine, methylamine group, dimethylamine, ethylamine group, diethylamine group, and the like. The phenyl or alkyl can be substituted or non-substituted, as long as the substituents do not interfere with the performance of the compounds as described herein.

In some embodiments, one or more of the acceptor-containing moieties is a heterocylic moiety and can be presented as follows:

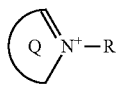

wherein Q is a positively charged nitrogen-containing heterocyclic moiety (heteroalicyclic or heteroaromatic); and R is hydrogen, alkyl or cycloalkyl.

Exemplary compounds can be represented by general Formula II:

Formula II

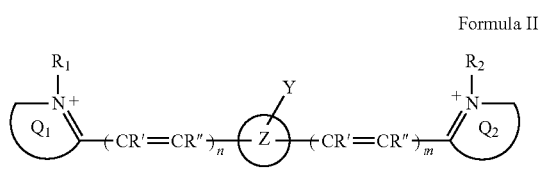

wherein:

$Q_1$ and $Q_2$ are each independently a substituted or unsubstituted heterocylic moiety, and are being an acceptor-containing moiety;

$R_1$ and $R_2$ are each independently selected from the group consisting of hydrogen, alkyl and cycloalkyl;

n and m are each independently an integer of from 0 to 4;

R' and R" are each independently hydrogen, alkyl or cycloalkyl, or, alternatively, R' and R" form together an aryl; and Z and Y together form the donor-containing moiety, as described herein.

In some embodiments, Z and Y together form a donor-containing moiety comprising an aromatic moiety substituted by an electron-donating group, said donor-containing moiety forming a conjugated π-electron system devoid of resonating electrons, and being such that upon a chemical event, it rearranges so as to transfer π-electrons to one of $Q_1$ and $Q_2$ and, as a result, this one of $Q_1$ and $Q_2$ becomes a donor moiety with respect to the other one of $Q_1$ and $Q_2$. Such a rearrangement is also referred to herein as intramolecular charge transfer (ICT).

In such compounds, an ammonium group represents the acceptor groups $A_1$ and $A_2$ in Formula I hereinabove, which form a part of the heterocyclic acceptor-containing moieties $Q_1$ and $Q_2$, respectively.

Exemplary heterocyclic moieties suitable for inclusion in the fluorogenic compounds disclosed herein as acceptor-containing moieties include, but are not limited to, ammonium forms of imidazoline ring, imidazole ring, benzimidazole ring, α-naphthoimidazole ring, β-naphthoimidazole ring, indole ring, isoindole ring, indolenine ring, isoindolenine ring, benzindolenine ring, pyridinoindolenine ring, oxazoline ring, oxazole ring, isoxazole ring, benzoxazole ring, pyridinooxazole ring, α-naphthoxazole ring, β-naphthoxazole ring, selenazoline ring, selenazole ring, benzoselenazole ring, α-naphthselenazole ring, β-naphthselenazole ring, thiazoline ring, thiazole ring, isothiazole ring, benzothiazole ring, α-naphthothiazole ring, β-naphthothiazole ring, tellulazoline ring, tellulazole ring, benzotellulazole ring, α-naphthotellulazole ring, β-naphthotellulazole ring, isoquinoline ring, isopyrrole ring, imidaquinoxaline ring, indandione ring, indazole ring, indoline ring, oxadiazole ring, carbazole ring, xanthene ring, quinazoline ring, quinoxaline ring, thiodiazole ring, thiooxazolidone ring, tetrazole ring, triazine ring, naphthyridine ring, piperazine ring, pyrazine ring, pyrazole ring, pyrazoline ring, pyrazolidine ring, pyrozolone ring, pyridine ring, pyridazine ring, pyrimidine ring, pyrylium ring, pyrrolidine ring, pyrroline ring, pyrrole ring, phenazine ring, phenanthridine ring, phthalazine ring, furazan ring, benzoxazine ring, morpholine ring, and rhodanine ring.

In some embodiments, one or more of the acceptor-containing moieties comprises a pyridine ring, such as a picoline ring (a methylpyridine ring, including all isomers thereof), and in some embodiments, one or more of the acceptor-containing moieties comprises a pyridinium ring (e.g., a picolinium ring).

In some embodiments, one or more of the acceptor-containing moieties is an indolenine-like ring.

The phrase "indolenine-like ring" describes a ring having an aromatic portion having fused thereto a positively-charged nitrogen-containing 5-membered aromatic portion such that positive charge resonates through the ring, as illustrated in the following formula:

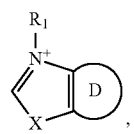

wherein D is an aryl, as defined herein, X can be, for example, a substituted or non-substituted carbon, a substituted or non-substituted nitrogen, sulfur, a substituted or non-substituted silicon; and R can be, for example, hydrogen, or, preferably, alkyl, cycloalkyl or any combination thereof.

Whenever the carbon, nitrogen or sulfur representing X in the above formula, are substituted, the substituents can be independently an alkyl, cycloalkyl, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide.

In some embodiments, one of the acceptor-containing moieties comprises a pyridine ring and one of the acceptor-containing moieties is an indolenine ring, as defined herein.

As discussed hereinabove, the fluorogenic compounds disclosed herein are designed capable of emitting near infrared light upon a chemical event, and as such, the acceptor-containing moieties, the donor-containing moieties and the linking moieties therein are such that, apart from possessing structural features that enable the required relocalization of the π-electrons, possess structural features that allow emission of NIR light upon undergoing a chemical event.

Exemplary such compounds are those in which the acceptor-containing moieties and the donor-containing moiety, and the optional linking moieties, form together a cyanine-like structure, or a squaraine-like structure.

As used herein, the phrase "cyanine-like structure" describes a molecule that has two nitrogen-containing moieties which are joined by a carbomethine-containing chain (e.g., a polymethine chain). One or both nitrogens can be a part of a nitrogen-containing heteroaromatic moiety, or, alternatively, be a secondary or tertiary ammonium.

In cyanine-like dye molecules, one nitrogen is positively charged (e.g., in a form of an ammonium ion) and one nitrogen atom is neutral (e.g., in a form of an amine) and thus has a lone pair of electrons. The positive charge in cyanine-like dyes therefore resonates between the two nitrogen atoms via the polymethine chain.

The fluorogenic compounds disclosed herein can be regarded as modified cyanine structures, which comprise two or more nitrogen-containing moieties within the acceptor-containing moieties and a donor-containing moiety. The nitrogen-containing moieties are positively-charged moieties such as ammonium-containing moieties.

Unlike cyanine dyes, in the modified cyanine structures disclosed herein, the presence of a donor-containing moiety interferes with the resonance (the delocalization of π electrons) between the two nitrogen atoms, and both nitrogen atoms are positively charged (e.g., in a form of an ammonium ion). As such, there is no delocalization of π-electrons (no resonating electrons) between the nitrogen-containing moieties.

Thus, in some embodiments, the fluorogenic compounds disclosed herein have cyanine-like structure, modified so as to include two positively charged nitrogen (e.g., ammonium)-containing moieties (instead of two nitrogen-containing moieties with one positive charge resonating therebetween) and donor-containing moiety that forms a conjugated π-electron system with the two ammonium-containing moieties, whereby the donor-containing moiety interferes with the delocalization of the π-electrons system of a non-modified cyanine-like molecule, by restricting delocalization of π-electrons to portions of the molecule that do not involve the nitrogen-containing moieties, and thus reduces or abolishes the delocalization of the positive charge that is present in non-modified cyanine-like molecules.

Such a fluorogenic compound is designed such that upon a chemical event, delocalization of the positive charge is restored (as illustrated, for example, in FIGS. 2A-C).

Due to the electronic structure of the fluorogenic compounds, in which no delocalization of π-electrons between the nitrogen-containing moieties is enabled, the compound is spectroscopically inactive (or has week spectroscopic properties) in the NIR range and thus is incapable of emitting light, particularly, near infrared light. Nonetheless, the arrangement of the functional moiety and the nitrogen-containing moieties allows to induce relocalization of the π-electrons by a chemical event, a relocalization that results in capability to emit near infrared light.

The relocalization of the π-electrons by the chemical event involves electronic rearrangement of the donor-containing moiety in the compound, in which electrons are transferred to one of the positively charged nitrogen-containing moieties (one of the acceptor-containing moieties), and as a result, a π-electron system with resonating electrons between the two nitrogen-containing moieties is formed and near infrared spectroscopic properties are imparted.

Thus, the fluorogenic compounds described herein follow a design in which the inclusion of the donor-containing moiety results in delocalization of π electrons through a smaller portion of the molecule (smaller number of overlapping p-orbitals), as compared to non-modified cyanine structures, and hence the compound is incapable of interacting with light so as to emit NIR light.

The fluorogenic compounds disclosed herein, however, further follow a design in which upon a chemical event, rearrangement of the donor-containing moiety occurs and results in a structure in which π electrons are relocalized such that one of the ammonium-containing moieties becomes an amine-containing moiety, and thus a resonating positive charge between two nitrogen-containing moieties, as in cyanine dyes, is restored. The π electrons relocalization thus results in a compound that has spectroscopic behavior similar to cyanine dyes, and is thus capable of emitting NIR light.

Accordingly, the cyanine-based fluorogenic compounds described herein are designed after known cyanine dyes, by having two nitrogen-containing moieties and a carbomethine-containing chain linking therebetween, yet differ from cyanine dyes by the presence of two positively charged (e.g., ammonium) nitrogen-containing moieties (instead of one positively charged nitrogen-containing moiety), and further by the presence of a donor-containing moiety as described herein.

Thus, in some embodiments, the fluorogenic compounds as described herein are modified cyanine dyes, including any of the known cyanine dyes, which are modified by the inclusion of a donor-containing moiety such as phenol within the cyanine structure, as described herein.

The fluorogenic compounds described herein can be regarded as comprising the same basic chemical arrangement as cyanine dyes, by having two nitrogen-containing moieties and a carbomethine-containing chain linking therebetween, yet, because of the donor-containing moiety included therewithin, the fluorogenic compounds exhibit an electronic arrangement that is different than that of cyanine dyes and therefore are spectroscopically inactive in the NIR range before activation by a chemical event.

Fluorogenic compounds which have a modified cyanine structure are also referred to herein as cyanine-based fluorogenic compounds.

In some embodiments, the cyanine-like structure comprises two ammonium-containing moieties as acceptor-containing moieties, as defined herein, which are linked therebetween via a carbomethine-containing chain.

The phrase "carbomethine-containing moiety" describes a moiety that comprises one or more —CR'=CR"= groups, as defined herein.

In some embodiments, the carbomethine-containing moiety is a polymethine chain.

The phrase "polymethine chain" describes a chain of methine groups (e.g., —CH=CH— groups) each can independently be substituted, as long as the substituent does not interfere with the optical properties of the disclosed compounds, as defined herein.

The donor-containing moiety forms a part of, or is attached to, the carbomethine-containing chain, such that a conjugated system is formed with the acceptor-containing moieties, as is further detailed hereinbelow.

The carbomethine-containing moiety and the donor-containing moiety that forms a part thereof or is attached thereto, together form a chain that can comprise from 2 to 13 carbon atoms, preferably from 2 to 7 carbon atoms.

In some embodiments, the carbomethine-containing chain comprises 2 carbon atoms and the cyanine-like structure is of a Cy2 type cyanine structure, as this term is widely recognized in the art.

In some embodiments, the carbomethine-containing chain comprises 3 carbon atoms and the cyanine-like structure is of a Cy3 type cyanine structure.

In some embodiments, the carbomethine-containing chain comprises 5 carbon atoms and the cyanine-like structure is of a Cy5 type cyanine structure.

In some embodiments, the carbomethine-containing chain comprises 7 carbon atoms and the cyanine-like structure is of a Cy7 type cyanine structure.

In some embodiments, the carbomethine-containing chain comprises 5 or 7 carbon atoms.

Exemplary cyanine-based fluorogenic compounds include as each of the acceptor-containing moiety, an indolenine ring (positively charged), as defined herein.

A carbomethine-containing chain (e.g., a polymethine chain) is linked to position 3 of each indolenine-like ring, so as to form a conjugated π-electrons system throughout the molecule.

Exemplary cyanine-based fluorogenic compounds can be collectively represented by the general Formula IIIB:

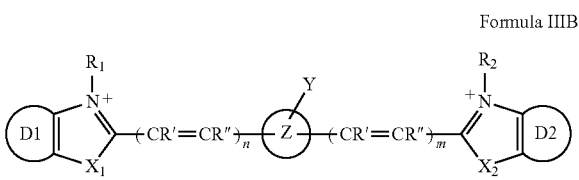

Formula IIIB wherein:

$D_1$ and $D_2$ are each independently an aryl, as defined herein, or is absent;

$X_1$ and $X_2$ are each independently selected from the group consisting of $CR_3R_4$, $NR_3$, and S, wherein $R_3$ and $R_4$ are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide;

$R_1$ and $R_2$ are each independently selected from the group consisting of hydrogen, alkyl and cycloalkyl;

n and m are each independently an integer of from 0 to 4;

R' and R'' are each independently hydrogen, alkyl or cycloalkyl, or, alternatively, R' and R'' form together an aryl; and Z and Y together form said functional moiety.

In some embodiments, $D_1$ and $D_2$ are each a substituted or unsubstituted phenyl.

In some embodiments, $X_1$ and $X_2$ are each independently $CR_3R_4$.

In some embodiments, $R_3$ and $R_4$ are each an alkyl.

In some embodiments, $R_1$ and $R_2$ are each hydrogen.

In some embodiments, $R_1$ and $R_2$ are each independently a substituted or unsubstituted alkyl.

It is to be noted that fluorogenic compounds in which one or more of the indolenine-like rings is replaced by any of the acceptor-containing moieties described herein, for example, any of the ammonium acceptor-containing moieties described herein (e.g., a pyridinium moiety), are also contemplated.

In some embodiments, the fluorogenic compound has general Formula IIIA:

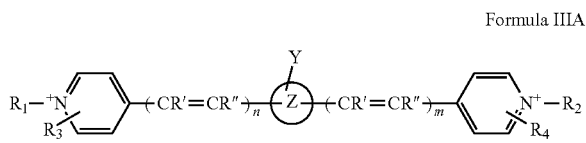

Formula IIIA wherein:

$R_1$ and $R_2$ are each independently selected from the group consisting of hydrogen, alkyl, cycloalkyl and aryl, heteroalicyclic, heteroaryl;

n and m are each independently an integer of from 0 to 4;

$R_3$ and $R_4$ are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide;

R' and R'' are each independently hydrogen, alkyl or cycloalkyl, or, alternatively, R' and R'' form together an aryl; and Z and Y form together the donor-containing moiety as described herein.

R' and R'' in each of a carbomethine moiety can be the same or different, whereby one carbomethine group can include R' and/or R'' different from the R' and/or R'' of another carbomethine chain.

In some embodiments, R' and R'' in each carbomethine moiety are both hydrogen.

Optionally, in one or more of the carbomethine moieties, R' and R'' form together an aryl, as exemplified, for example, in FIG. 2.

In some embodiments, the donor-containing moiety forms a part of the carbomethine-containing chain, and thus can be represented as a —CRc=CRd— moiety, in which one of Rc and Rd comprises an electron-donating group, as defined herein.

In some embodiments, Rc and Rd together form an aromatic ring, which is substituted by an electron-donating group, as defined herein.

In some embodiments, the donor-containing moiety is attached to the carbomethine-containing chain, while maintaining a conjugated π electrons system, as described herein.

Exemplary such donor-containing moiety is —C(=CR-cRd)—[CReRf=CRcRd]t—, with Rc and Rd each independently being hydrogen, alkyl, aryl or cycloalkyl or, alternatively, Rc and Rd form together a heteroalicyclic or a heteroaryl; Re and Rf being as defined for Rc and Rd; and t being an integer from 0 to 10 or from 0 to 6, or from 0 to 4, or from 0 to 2. Rc, Rd, Re and Rf can be the same or different. When t is greater than 0, the donor-containing moiety comprises a polymethine chain.

In some embodiments, the aromatic group of a donor-containing moiety is substituted by the electron-donating group at a position that allows the donor-containing group to undergo a 1,4-quinonemethidine-like rearrangement, as described herein, as exemplified in FIG. 2.

In some embodiments, the fluorogenic compound comprises more than two (e.g., 3) acceptor-containing moieties, as exemplified, for example, in FIG. 2.

In exemplary such embodiments, the fluorogenic compound follows a design in which the donor-containing moiety is conjugated to three acceptor-containing moieties such that upon a chemical event, it rearranges so as to transfer electrons to one of the acceptor-containing moieties, rendering it a donor-containing moiety with respect to the other two acceptor-containing moieties.

Exemplary fluorogenic compounds are depicted in the Examples section that follows (see, for example, Table 1).

The Turn-ON Mechanism:

In some embodiments, the donor-containing moiety is a cleavable moiety, which is cleaved upon the chemical event so as to generate a reactive electron-donating group.

For example, in cases where the electron-donating group in the donor-containing moiety comprises oxygen as a reactive electron-donating group, the donor-containing moiety can comprise a hydroxyl group, which upon deprotonation, generates a reactive $O^-$ donor.

Thus, in some embodiments, the electron-donating moiety comprises a hydroxyl group, and can be, for example, phenol, hydroxyl-naphthalene, any other hydroxyl-substituted aryl, or, alternatively, can be a hydroxyl group per se, or a carbomethine group, as defined herein, substituted by a hydroxyl.

Similarly, in cases where the electron-donating group in the donor-containing moiety comprises sulfur as a reactive electron-donating group, the donor-containing moiety can comprise a thiol group, which upon deprotonation, generates a reactive $S^-$ donor.

Thus, in some embodiments, the donor-containing moiety comprises a thiol group, and can be, for example, thiophenol, thio-naphthalene, any other thiol-substituted aryls, or, alternatively, can be a thiol group per se, or a carbomethine group, as defined herein, substituted by a thiol.

Similarly, in cases where the electron-donating group in the donor-containing moiety comprises nitrogen (amine) as a reactive electron-donating group, the donor-containing moiety can comprise an amine group.

Thus, in some embodiments, the donor-containing moiety comprises an amine group, and can be, for example, aniline, amino-naphthalene, any other amino-substituted aryls, or, alternatively, can be an amine group per se, or a carbomethine group, as defined herein, substituted by an amine.

In some embodiments, the donor-containing moiety comprises hydroxyl, thiol and/or amine groups as described herein, which are cleaved to generate a reactive species by deprotonation. In some embodiments, deprotonation occurs once the fluorogenic compound is in an aqueous solution or any other solution having a pH higher than a pKa value of the compound.

In some embodiments, these electron-donating moieties are present as latent groups in the donor-containing moiety, which are generated upon a cleavage event.

In such embodiments, the donor-containing moiety comprises a cleavable trigger unit, which, upon a chemical event, is cleaved to generate the (reactive) electron-donating group, as defined herein.

In the general Formulae I-III depicted hereinabove, Y represents an electron-donating group or a cleavable trigger unit that upon the chemical event, generates the electron-donating group. Z can be absent or can be an aryl, carbomethine or polymethine chain, as described hereinabove.

The cleavable trigger unit can be a chemically removable trigger that is cleaved upon a chemical reaction with an analyte, as is described in further detail hereinunder and is exemplified in the Examples section that follows.

Alternatively or in addition, the cleavable trigger unit can be a biodegradable trigger that is cleaved upon a biological reaction with the appropriate biological trigger.

Exemplary biological triggers according to the present embodiments are enzymes, whereas the trigger units are the corresponding enzymatic substrates or are any other unit that is cleavable by a selected enzyme. Additional exemplary biological triggers are reagents that are endogenously or exogenously produced in response to a biological process.

Fluorogenic compounds which comprise a trigger unit that is cleavable by a specific analyte, be it a chemical reagent or a biomolecule such as an enzyme, can be used for detecting the analyte by NIR imaging, as described in further detail hereinunder.

The Fluorescent Compounds:

Each of the fluorogenic compounds described herein generates a fluorescent compound, which is capable of emitting NIR light, upon a chemical event.

The generated fluorescent compounds are characterized by beneficial spectroscopic properties, such as high quantum yields, and high extension coefficient.

Thus, according to some embodiments of the invention, the fluorescent compounds are derived from the herein described fluorogenic compounds, and comprise an acceptor-containing moiety, as defined herein, a donor-containing moiety that corresponds to an acceptor-containing moiety (e.g., an amine-containing moiety corresponding to an ammonium acceptor-containing moiety), and a moiety that is derived from the donor-containing moiety described for the fluorogenic compounds and is in a rearranged form of the donor-containing moiety described hereinabove.

In some embodiments, a fluorescent compound comprises an ammonium acceptor-containing moiety, and amine donor-containing moiety, and one or more carbomethine-containing moieties (e.g., a polymethine chain) linking between these moieties, all having a conjugated π-electrons system in which the positive charge of the ammonium is delocalized, and hence, in which resonating electrons are present. The fluorescent compound further comprises a rearranged form of the donor-containing moiety described hereinabove, obtained upon the electron transfer that occurred upon the chemical event. This rearranged form can be, for example, the species formed upon 1,4-quinonemethidine rearrangement of an aromatic moiety that was substituted by an electron-donating moiety (e.g., phenol), being part of the polymethine chain or being attached thereto (as depicted, for example, in FIG. 2).

Exemplary fluorescent compounds can be represented by the following general Formula IV:

Formula IV

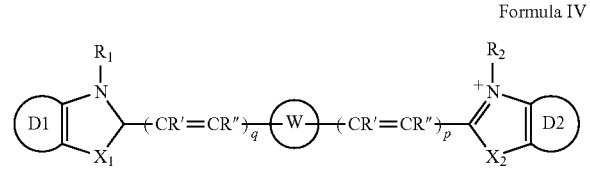

wherein:

$D_1$ and $D_2$ are each independently an aromatic moiety, as defined herein for the fluorogenic compounds;

$X_1$ and $X_2$ are each independently selected from the group consisting of CR'R", NR', O, S and SiR'R", wherein R' and R" are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide;

$R_1$ and $R_2$ are each independently selected from the group consisting of hydrogen, alkyl, cycloalkyl and aryl, heteroalicyclic, heteroaryl;

p and q are each independently an integer of from 0 to 4; and

W is a group that comprises an aromatic moiety, wherein the π-electrons of the aromatic moiety are conjugated to the π electrons of the —(CH=CH)p- and the —(CH=CH)q— groups, such that delocalization of π electrons is effected between the ammonium and the amine groups in the molecule.

W represents a group that is derived from the donor-containing moiety described herein in the context of the fluorogenic compounds, as explained hereinabove.

$D_1$, $D_2$, $X_1$, $X_2$, $R_1$, $R_2$, R and R" are as described hereinabove in the context of the fluorogenic compounds.

Exemplary compounds are depicted in FIG. 2 and additional compounds described in the Examples section that follows.

It is to be noted that fluorescent compounds in which the ammonium-containing indolenine group included in the fluorescent compounds described herein are replaced by any of the acceptor-containing moieties described hereinabove are also contemplated. Exemplary such fluorescent compounds include, for example, compounds in which one or both indolenine groups are replaced by a pyridine or pyridinium (e.g., picoline or picolinium).

In addition, or alternatively, fluorescent compounds in which the amine-containing indolenine group included in the fluorescent compounds described herein is replaced by any of the heterocylic moieties described hereinabove are also contemplated, as presented in the claims.

Exemplary such fluorescent compounds include, for example, compounds in which one or both indolenine groups are replaced by a pyridine or pyridinium (e.g., picoline or picolinium), as depicted by Formulae IVA and IVB, as follows.

In some embodiments, the fluorescent compound has general Formula IVA:

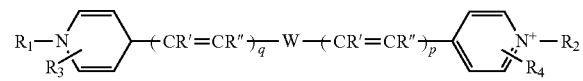

Formula IVA wherein:

$R_1$ and $R_2$ are each independently selected from the group consisting of hydrogen, alkyl, cycloalkyl and aryl, heteroalicyclic, heteroaryl;

p and q are each independently an integer of from 0 to 4;

$R_3$ and $R_4$ are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide;

R' and R" are each independently hydrogen, alkyl or cycloalkyl, or, alternatively, R' and R" form together an aryl; and W is as defined herein.

In some embodiments, the fluorescent compound has general Formula IVB:

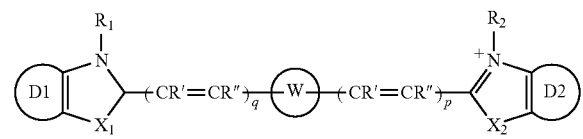

Formula IVB wherein:

$D_1$ and $D_2$ are each independently an aromatic moiety;

$X_1$ and $X_2$ are each independently selected from the group consisting of CR'R", NR', O, S and SiR'R", wherein R' and R" are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide;

$R_1$ and $R_2$ are each independently selected from the group consisting of hydrogen, alkyl, cycloalkyl and aryl, heteroalicyclic, heteroaryl;

p and q are each independently an integer of from 0 to 4;

R' and R" are each independently hydrogen, alkyl or cycloalkyl, or, alternatively, R' and R" form together an aryl; and W is as defined herein.

Exemplary fluorescent compounds are described in the Examples section that follows, for example in Table 1, which presents the phenol compounds which generate fluorescent compounds having advantageous spectral properties.

Prodrugs Incorporating a Turn-ON NIR Probe:

In some embodiments, the fluorogenic compounds described herein further comprise a therapeutically active agent (e.g., a drug) attached to the donor-containing moiety, such that upon the chemical event, the therapeutically active agent is released.

In some embodiments, the donor-containing moiety comprises a cleavable trigger unit, and the donor-containing moiety, the cleavable trigger unit and the therapeutically active agent are such that upon cleavage of the trigger unit (the chemical event), the therapeutically active agent is released.

This can be achieved, for example, by utilizing a self-immolative spacer to which the trigger unit and the therapeutically active agent are linked, such that the self-immolative spacer self-immolates upon the chemical event (the cleavage of the trigger unit) to thereby release the therapeutically active agent, and to generate a donor-containing species that can rearrange as described herein for the donor-containing moiety, so as to produce a compound that emits NIR light.

Self-immolative spacers are known in the art, and all are contemplated in these embodiments.

Exemplary self-immolative spacers are such that are capable of undergoing a sequence of self-immolative reactions upon cleavage of the trigger unit.

Self-immolative reactions typically involve electronic cascade self-elimination and therefore self-immolative systems typically include electronic cascade units which self-eliminate through, for example, linear or cyclic 1,4-elimination, 1,6-elimination, etc.

In some embodiments, the self-immolative adaptors are five- or six-membered aromatic rings, such as described, for example, in WO 2004/019993, which is incorporated by reference as if fully set forth herein.

Examples include spacers that can undergo a 1,4-quinonemethide rearrangement such that upon the cleavage event, the therapeutically active agent is released and a species that can further undergo a 1,4-quinonemethide rearrangement is formed.

Exemplary such fluorogenic compounds are depicted in FIG. 15.

When such fluorogenic compounds undergo specific activation, the drug is released and fluorescence is generated through formation of a fluorescent compound. Consequently, activation by a selected chemical event provides data on time and location of drug release.

Such fluorogenic compounds are highly useful drug delivery systems since (i) by selecting an appropriate trigger unit, selective, targeted delivery is achieved; and (ii) real-time information about the release process is obtained using non-invasive fluorescence detection techniques.

Representative examples of therapeutically active agents that can be efficiently incorporated in the fluorogenic compounds described herein include, without limitation, anti-proliferative agents, anti-inflammatory agents, antibiotics, anti-viral agents, anti-hypertensive agents and/or chemosensitizing agents.

Non-limiting examples of anti-inflammatory agents useful in the context of some embodiments of the present invention include methyl salicylate, aspirin, ibuprofen, and naproxen, and derivatives thereof.

Non-limiting examples of antiviral agents useful in the context of some embodiments of the present invention include famciclovir, valacyclovir and acyclovir, and derivatives thereof.

Non-limiting examples of antibiotics include penicillin-V, azlocillin, and tetracyclines, and derivatives thereof.

In some embodiments, the therapeutically active agent is an anti-proliferative agent such as a chemotherapeutic agent.

Non-limiting examples of chemotherapeutic agents that can be efficiently incorporated in the herein described fluorogenic compounds include amino containing chemotherapeutic agents such as daunorubicin, doxorubicin, N-(5,5-diacetoxypentyl)doxorubicin, anthracycline, mitomycin C, mitomycin A, 9-amino camptothecin, aminopertin, antinomycin, $N^8$-acetyl spermidine, 1-(2-chloroethyl)-1,2-dimethanesulfonyl hydrazine, bleomycin, tallysomucin, and derivatives thereof; hydroxy containing chemotherapeutic agents such as etoposide, camptothecin, irinotecaan, topotecan, 9-amino camptothecin, paclitaxel, docetaxel, esperamycin, 1,8-dihydroxy-bicyclo [7.3.1]-trideca-4-ene-2,6-diyne-13-one, anguidine, morpholino-doxorubicin, vincristine and vinblastine, and derivatives thereof, sulfhydril containing chemotherapeutic agents and carboxyl containing chemotherapeutic agents.

Other therapeutically active agents that can be beneficially incorporated in the herein described fluorogenic compounds include, for example, antihistamines, anesthetics, analgesics, anti-fungal agents, vitamins and anti-infectious agents.

The fluorogenic compound, according to these embodiments, is designed such that the chemical event is induced by a biological compound that is associated with a medical condition that is treatable by the therapeutically active agent.

Applications:

Any of the fluorogenic compounds and the fluorescent compounds described herein can be used in methods that involve NIR imaging, for imaging a sample.

Such methods involve contacting the compound with the sample and collecting the light emitted from the sample.

The sample can be simply an aqueous solution. The sample can be a biological sample, such as a cell culture, a microorganism, a sample of a bodily fluid (e.g., blood or urine), or a sample of a bodily tissue or organ. The sample can also be a bodily site.

As used herein, the phrase "bodily site" includes any organ, tissue, membrane, cavity, blood vessel, tract, biological surface or muscle.

Exemplary bodily sites, and tissues or organs derived therefrom, include, but are not limited to, the skin, a dermal layer, the scalp, an eye, an ear, a mouth, a throat, a stomach, a small intestines tissue, a large intestines tissue, a kidney, a pancreas, a liver, the digestive system, the respiratory tract, a bone marrow tissue, a mucosal membrane, a nasal membrane, the blood system, a blood vessel, a muscle, a pulmonary cavity, an artery, a vein, a capillary, a heart, a heart cavity, a male or female reproductive organ and any visceral organ or cavity.

In some embodiments, the collected light is processed to generate a signal or an image.

Any NIR imaging technique and instrumentation (e.g., optical filters, detectors, digital processors, and the like) can be utilized for collecting the emitted light. Typically, a sample is first irradiated, preferably at about a wavelength in which the compound has an absorbance maxima. Such a wavelength can be readily determined by conventional spectroscopic assays. In some embodiments, collecting the light is effected with a NIR camera, which processes the collected light into an image.

Fluorogenic compounds are typically preferred over the fluorescent compounds disclosed herein, because of the Turn-ON mechanism associated therewith.

The fluorogenic compounds can be utilized in methods for determining a presence and/or a level of an analyte that generates the chemical event.

When the compounds contact the analyte at quest, a chemical event (e.g., cleavage), as described herein, leads to generation of a fluorescent compound that is capable of emitting NIR light.

The presence and/or level of the emitted NIR light is thus indicative of the presence and/or level of the analyte the generates the chemical event.

Determination of the presence and/or level of the emitted NIR light can be effected by collecting the emitted NIR light, as described hereinabove.

In some embodiments, the analyte is a chemical reagent that reacts with the fluorogenic compound so as to generate a fluorescent compound, as described herein.

In some embodiment the analyte is known as indicative for biological processes. In these embodiments, the trigger unit is a biodegradable trigger unit that is cleaved by the biological analyte.

In some embodiments, the analyte is associated with a medical condition, and determining a presence and/or level of the analyte is utilized for determining a presence or progression of this medical condition.

In some embodiments, the analyte is an enzyme overexpressed in organs or tissues afflicted by the medical condition.

In some embodiments, the analyte is a substance that is produced in organs or tissues in response to the medical condition.

In some embodiments, a biodegradable trigger unit is cleaved upon a reaction with a reagent that is indicative for the presence of a medical condition, such that a presence and/or level of emitted NIR light is indicative for the presence and/or level of the medical condition.

An exemplary such reagent is hydrogen peroxide, with is indicative for inflammatory processes, as is discussed in further detail in the Examples section that follows. In such exemplary embodiments, a fluorogenic compound with a hydroxide-peroxide sensitive trigger unit can be efficiently utilized (as exemplified in the Examples section that follows). An exemplary cleavable trigger unit that is cleaved by hydrogen peroxide is a boronic acid or ester.

An additional exemplary reagent is NO, which is indicative for hypoxia [Kiang, J., Tsen, K T, *Biology of hypoxia*. The Chinese Journal of Physiology 2006. 49(5): p. 223-233]. Fluorogenic compounds that comprise a cleavable trigger unit that is cleaved by NO can therefore be utilized for monitoring hypoxia and thus any angiogenesis-dependent diseases and disorders.

An additional exemplary reagent is Fe(II), which is indicative for Malaria [Mahajan et al. ChemMedChem, 2011. 6: p. 415-419]. An exemplary cleavable trigger unit that is cleaved by Fe(II) is a trioxalane ring. Fluorogenic compounds that comprise a cleavable trigger unit that is cleaved by Fe(II) can therefore be utilized for monitoring hypoxia and thus any angiogenesis-dependent diseases and disorders.

An additional exemplary reagent is a thiol, which is indicative for cancer tumors. Fluorogenic compounds that comprise a cleavable trigger unit that is cleaved by thiols can therefore be utilized for, for example, monitoring cancer tumors, and may further be utilized, for example, for monitoring thiol levels in the blood and/or the glutathione reductase assisted glutathione redox process.

The thiol can form a part of a cysteine or a peptide containing N-terminal cysteine. An exemplary triggering unit that cleavable by cysteine is presented in FIGS. 28 and 29, and in Example 9 in the Examples section that follows.

An additional exemplary reagent is fluoride. Fluorogenic compounds that comprise a cleavable trigger unit that is cleaved by fluoride can be utilized, for example, for detecting fluoride in samples such as drinking water.

In some embodiments, a biodegradable trigger unit is cleaved upon a pH change, namely, in presence of an acid or a base, or in an acidic environment or a basic environment, which is indicative for the presence of a medical condition in a certain organ or issue, such that a presence and/or level of emitted NIR light is indicative for the presence and/or level of the medical condition in this organ or tissue. Exemplary such medical conditions include, but are not limited to, cancer, inflammation, and angiogenesis-dependent diseases or disorders, where pH is known to be lower than normal physiological pH. Fluorogenic compound having a trigger unit that is cleavable in an acidic environment can also be used for imaging the stomach.

Exemplary cleavable trigger units that are cleaved at acidic environment (acid-labile trigger units) include, but are not limited to, trigger units which include N-cis-aconityl, hydrazone, and carboxylic-hydrazone bonds, acetal, imine and trityl bonds, acetal bonds.

In some embodiments, the analyte is an enzyme that is known to be overexpressed as a result of a biological process (e.g., a disease or disorder). In such exemplary embodiments, a fluorogenic compound with a trigger unit that is cleavable by the enzyme (e.g., is the enzyme's substrate) can be efficiently utilized.

Exemplary diseases and disorders which involve overexpression of one or more enzymes include, but are not limited to, various cancer tumors (e.g., breast, lung, colorectal, gastric, cervical), cancer invasion and metastases, hepatoma metastasis, hematological cancers (leukemia, lymphoma, etc.), angiogenesis-dependent disease and disorders (including, for example, macular degeneration, malaria and leishmeniasis), metastatic bone disease, osteoporosis, osteoarthritis, autoimmune diseases such as multiple sclerosis, rheumatoid arthritis, psoriasis, ocular diseases such as macular degeneration, diabetes, diabetic retinopathy, atherosclerosis, heart failure following myocardial infraction, chronic obstructive pulmonary disease, cerebral ischemia, gastrointestinal diseases associated with ulceration, other inflammatory diseases and disorders and hypoxia.

In some embodiments, the enzyme is overexpressed in tumors (e.g., cancer tumors). Exemplary such enzymes include, but are not limited to, Cathepsins (cysteine proteases) such as Cathepsin B, Cathepsin K, Cathepsin D, Cathepsin H, Cathepsin L, and Cathepsin S, legumain, matrix metalloproteinases such as MMP-2 and MMP-9, as well as MMP1, MMP3, MMP7, MMP13 and MMP14, KLK6 (kallikrein-related peptidase-6 which encodes a trypsin-like serine peptidase), PIM serine/threonine kinases such as PIM 1, PIM 2 and PIM 3, histone deacetylases (HDAC) such as HDAC1, HDAC2, HDAC3, HDAC6 AND kdac8.

In some embodiments, the enzyme is overexpressed as a result of inflammation. In some embodiments, the enzyme is overexpressed as a result of an autoimmune disease.

Suitable trigger units having a Cathepsin cleavable site include amino acid sequences such as, but not limited to, -[Asn-Glu-Val-Ala]- and -[Lys-Lys]-.

Suitable trigger units having cathepsin-B cleavable sites include amino acid sequences such as, but are not limited to, -[Gly-Phe-Lys]-, -[Cit-Val]-, -[Arg]-, -[Arg-Arg]-, -[Val-Arg]-, -[Phe-Lys]-, -[Phe-Arg]-, [Gly-Phe-Leu-Gly], -[Gly-Phe-Ala-Leu]- and -[Ala-Leu-Ala-Leu]-, -[Gly-Leu-Gly]-, -[Gly-Phe-Gly]-, -[Gly-Phe-Leu-Gly-Phe-Lys]-, -[(Glu)$_6$-(Asp)$_8$]- and combinations thereof.

In some embodiments the trigger unit comprises the amino acid sequences -[Gly-Phe-Lys]-, -[Gly-Leu-Gly]-, -[Gly-Phe-Gly]-, -[Gly-Leu-Phe-Gly]-, -[Gly-Phe-Leu-Gly]-, -[Phe-Lys]- and -[Gly-Phe-Leu-Gly-Phe-Lys]-. In some embodiments, the trigger unit consists of these amino acid sequences or a combination thereof.

Cathepsin B is overexpressed in cancer tumors and hence fluorogenic compounds with trigger units that have cathepsin-B cleavable sites can be used for monitoring presence and/or progression of cancer tumors.

Suitable trigger units having cathepsin-D cleavable sites include an amino acid sequence such as, but are not limited to, -[Gly-Pro-Ile-Cys(Et)-Phe-Phe-Arg-Leu]-.

Cathepsin D is overexpressed in cancer metastasis and hence fluorogenic compounds with trigger units that have cathepsin-D cleavable sites can be used for monitoring presence and/or progression of cancer metastases.

Suitable trigger units having cathepsin-K cleavable sites include an amino acid sequence such as, but are not limited to, -[Gly-Gly-Pro-Nle]-.

Cathepsin K is overexpressed in breast cancer; metastatic bone disease; osteoporosis, psoriasis, multiple sclerosis, rheumatoid arthritis and osteoarthritis, and hence fluorogenic compounds with trigger units that have cathepsin-K cleavable sites can be used for monitoring presence and/or progression of these diseases and disorders.

Suitable trigger units having cathepsin-L cleavable sites include an amino acid sequence such as, but are not limited to, -[Phe-Arg]-.

Cathepsin L is overexpressed in cancer tumors, and hence fluorogenic compounds with trigger units that have cathepsin-L cleavable sites can be used for monitoring presence and/or progression of cancer tumors.

Cathepsin H is overexpressed in hepatoma metastasis, and hence fluorogenic compounds with trigger units that have cathepsin-H cleavable sites can be used for monitoring presence and/or progression of hepatoma metastases.

Cathepsin S is overexpressed in osteoporosis, psoriasis, multiple sclerosis, rheumatoid arthritis and osteoarthritis, and hence fluorogenic compounds with trigger units that have cathepsin-S cleavable sites can be used for monitoring presence and/or progression of these diseases and disorders.

Suitable trigger units having Legumain cleavable sites include an amino acid sequence such as, but are not limited to, -[Ala-Ala-Asn]-, -[Asn-Glu-Val-Ala]- and -[(Glu)$_6$-(Asp)$_8$]-, and any combination thereof. Matrix metalloproteinases (MMP), in particular MMP-2 and MMP-9, have been identified as important proteases for the progression of malignant tumors (e.g., colorectal cancer, lung cancer), as well as in inflammation, heart failure following MI, COPD, ocular diseases and gastrointestinal diseases associated with ulceration, and hence fluorogenic compounds with trigger units that have MMPs cleavable sites can be used for monitoring presence and/or progression of these diseases and disorders.

Suitable trigger units having MMP cleavable sites include an amino acid sequence such as, but are not limited to, -[Cys-Gly-Leu-Asp-Asp]-, -[Gly-Pro-Leu-Gly-Val]-, -[Gly-Pro-Leu-Gly-Ala-Gly]-, -[Cys-Asp-Gly-Arg]-, -[Gly-Pro-Leu-Gly-Val-Arg-Gly-Cys]- and -[Pro-Leu-Gly-Met-Thr-Ser]-, and any combination thereof. In some embodiments, the trigger units have only a part of the above-described amino acid sequences. In some embodiments, the trigger unit consists of 3 amino acids of the above-described sequences.

Suitable trigger units having MMP-2 and MMP-9 cleavable sites include an amino acid sequence such as, but are not limited to, -[Gly-Pro-Gln-Gly-Ile-Ala-Gly-Gln]-, -[Gly-Pro-Leu-Gly-Ile-Ala-Gly-Gln]-, -[Gly-Pro-Gln-Gly-Ile-Trp-Gly-Gln]-, -[Pro-Leu-Gly-Val-Arg]-, [Pro-Leu-Gly-Leu-Tyr-Leu]-, -[Pro-Leu-Gly-Leu-Tyr-Ala-Leu]-, -[Gly-Pro-Leu-Gly-Ile-Ala-Gly-Gln]-, -[Gly-Pro-Leu-Gly-Leu-Trp-Ala-Gln]-, -[Gly-Pro-Leu-Gly-Val-Arg-Gly-Lys]-, -[His-Pro-Val-Gly-Leu-Leu-Ala-Arg]-, -[Gly-Gly-Pro-Leu-Gly-Leu-Trp-Ala-Gly-Gly]-, -[Ala-Ala-Ala-Pro-Leu-Gly-Leu-Trp-Ala]- and combinations thereof. In some embodiments, the trigger units have only a part of the above-described amino acid sequences. In some embodiments, the trigger unit consists of 3 amino acids of the above-described sequences.

MMP2 and MMP9 are overexpressed in arthritis, tumor invasion and metastases, angiogenesis and cerebral ischemia, and hence fluorogenic compounds with trigger units that have MMP2 or MMP9 cleavable sites can be used for monitoring presence and/or progression of these diseases and disorders.

Suitable trigger units having MMP-7 cleavable sites include an amino acid sequence such as, but are not limited to, -[Gly-Val-Pro-Leu-Ser-Leu-Thr-Met-Gly-Cys]- and -[Arg-Pro-Leu-Ala-Leu-Trp-Arg-Ser]- and combinations thereof. In some embodiments, the trigger units have only a part of the above-described amino acid sequences. In some embodiments, the trigger unit consists of 3 amino acids of the above-described sequences.

Suitable trigger units having MMP-13 cleavable sites include an amino acid sequence such as, but are not limited to, -[Gly-Pro-Leu-Gly-Met-Arg-Gly-Leu-Gly-Lys]-. In some embodiments, the trigger units have only a part of the above-described amino acid sequence. In some embodiments, the trigger unit consists of 3 amino acids of the above-described sequence.

Suitable trigger units having KLK6 cleavable sites include amino acid sequences such as, but are not limited to, -[Gly-Ala-Arg-Arg-Arg-Gly]-, -[Trp-Ala-Arg-Arg-Ser]-, -[Trp-Ala-Arg-Lys-Arg]-, -[Les-Arg-Lys-Arg-Trp]-, -[Ala-Lys-Arg-Arg-Gly]-, abd -[Trp-Lys-Lys-Lys-Arg]. In some embodiments, the trigger units have only a part of the above-described amino acid sequences. In some embodiments, the trigger unit consists of 3 amino acids of the above-described sequences.

KLK6L is overexpressed in colon and gastric cancers, and hence fluorogenic compounds with trigger units that have KLK6L cleavable sites can be used for monitoring presence and/or progression of such cancers.

PIMs (PIM1, PIM2 and PIM3) are serine/threonine kinases overexpressed in hematologic malignancies and solid cancers, and hence fluorogenic compounds with trigger units that have PIM cleavable sites can be used for monitoring presence and/or progression of such malignancies.

Suitable trigger units having PIM cleavable sites include an amino acid sequence such as, but are not limited to, -[(Arg/Lys)$_3$-AA$_1$-[Ser/Thr-AA$_2$]-, with AA$_1$ and AA$_2$ being independently any amino acid residue except basic or large hydrophobic residues. An exemplary amino acid sequence include: -[Ala-Arg-Lys-Arg-Arg-Arg-His-Pro-Ser-Gly-Pro-Pro-Thr-Ala]-. Suitable trigger units having HDAC cleavable sites include acetylated Lysine.

HDACs are overexpressed in cancer tumors. HDAC1 is known to be associated with prostate, gastric, colon and breast tumors; HDAC2 is known to be associated with colorectal, cervical and gastric tumors; HDAC3 is known to be associated with colon tumors; and HDAC6 is known to be associated with breast tumors. Fluorogenic compounds with trigger units that have cleavable sites of on or more HDAC can be used for monitoring presence and/or progression of the above-indicated cancer tumors.

Caspases (e.g., Caspase3, Caspase 7 and Caspase 9) are proteases that can be used to monitor biological processes associated with apoptosis and hypoxia, and hence fluorogenic compounds with trigger units that have caspase cleavable sites can be used for monitoring presence and/or progression of such processes.

Suitable trigger units having caspase cleavable sites include an amino acid sequence such as, but not limited to, -[Asn-Glu-Val-Ala]-, -[(Glu)$_6$-(Asp)$_8$]-, -[Asp-Glu-Val-Asp]-, and [Asp-Glu-Val-Asp-Ala-Pro-Lys]-.

In some embodiments, the enzyme is a galatosidase, e.g., alpha-galactosidase or beta-galactosidase, which is highly expressed and accumulated in lysosomes in senescent cells. Fluorogenic compounds with trigger units that have galactosidase cleavable sites can be used for monitoring presence and/or progression of metabolic diseases and disorders, and for detecting or monitoring senescence in vivo and in vitro. Trigger units cleavable by galactosidases comprise a glucose moiety and are exemplified in FIGS. 28 and 29 and in Example 9 in the Examples section that follows.

In some embodiments, the enzyme is nitroreductase (NTR).

Whenever the fluorogenic compound further comprises a therapeutically active agent that can be released upon the chemical event, the active agent can be selected as being suitable for treating a medical condition for which the analyte is indicative.

Thus, for example, if a biodegradable trigger unit is cleavable by an enzyme that is overexpressed in cancer tumors, the therapeutically active agent can be a chemotherapeutic agent, and the fluorogenic compound can also be utilized for monitoring the therapeutic effect of the chemotherapeutic agent, as detailed hereinabove.

If a biodegradable trigger unit is cleavable by an enzyme that is indicative for apoptosis, the therapeutically active agent can be a chemotherapeutic agent, and the fluorogenic compound can also be utilized for monitoring the therapeutic effect of the chemotherapeutic agent, as detailed hereinabove.

If a biodegradable trigger unit is cleavable by a reagent that is associated with inflammation, the therapeutically active agent can be an anti-inflammatory agent, and the fluorogenic compound can also be utilized for monitoring the therapeutic effect of the anti-inflammatory agent, as detailed hereinabove.

Additional combinations of cleavable trigger units and therapeutically active agent, and related applications, will be readily recognized by those skilled in the art, in view of the foregoing description.

In some embodiments, the fluorogenic compounds described herein form a part of a polymeric structure.

In any of the methods and uses described herein, the fluorogenic (or fluorescent) compounds as described herein can be utilized either per se or as a part of a pharmaceutical composition that further comprises a carrier.

As used herein a "pharmaceutical composition" refers to a preparation of one or more of the fluorogenic (or fluorescent) compounds described herein, or physiologically acceptable salts or prodrugs thereof, with other chemical components including but not limited to physiologically suitable carriers, excipients, lubricants, buffering agents and the like. The purpose of a pharmaceutical composition is to facilitate administration of a compound to a subject. The term "active ingredient" refers to a compound, which is accountable for a biological effect, herein for diagnostics.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a fluorogenic (or fluorescent) compound as described herein. Examples, without limitation, of excipients include calcium carbonate, calcium phosphate, various sugars and types of starch, cellulose derivatives, gelatin, vegetable oils and polyethylene glycols.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice. Administration may be done orally, by inhalation, or parenterally, for example by intravenous drip or intraperitoneal, subcutaneous, intramuscular or intravenous injection, or topically (including ophtalmically, vaginally, rectally, intranasally).

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

According to some embodiments of the present invention, the pharmaceutical composition described hereinabove is packaged in a packaging material and identified in print, in or on the packaging material, for use in monitoring a medical condition. The medical condition is such that is associated with an analyte that induces the herein described chemical event (e.g., an enzyme).

According to some embodiments, the pharmaceutical composition is packaged in a packaging material and identified in print, in or on the packaging material, for use in treating a medical condition. Such pharmaceutical compositions comprise a fluorogenic compound that further comprises a therapeutically active agent, as described herein, and can further be identified for monitoring the drug release and therapeutic effect of the drug.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be unsubstituted or substituted, as long as the substituent does not interfere with the performance and/or intended use of the compound. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be unsubstituted or substituted, as long as the substituent does not interfere with the performance and/or intended use of the compound. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be unsubstituted or substituted, as long as the substituent does not interfere with the performance and/or intended use of the compound. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, indole, indolenine, quinoline, isoquinoline and purine. The heteroaryl group may be unsubstituted or substituted, as long as the substituent does not interfere with the performance and/or intended use of the compound. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be unsubstituted or substituted, as long as the substituent does not interfere with the performance and/or intended use of the compound. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like.

A "hydroxy" group refers to an —OH group.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is defined as hereinabove.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

An "oxo" group refers to a =O group.

A "carboxylate" or "carboxyl" encompasses both C-carboxy and O-carboxy groups, as defined herein.

A "carboxylic acid" group refers to a C-carboxy group in which R' is hydrogen.

A "thiocarboxy" or "thiocarboxylate" group refers to both —C(=S)—O—R' and —O—C(=S)R' groups.

An "ester" refers to a C-carboxy group wherein R' is not hydrogen.

An ester bond refers to a —O—C(=O)— bond.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

A carbamate bond describes a —O—C(=O)—NR'— bond, where R' is as described herein.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(=S)—NR'— bond, where R' is as described herein.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

An amide bond describes a —NR'—C(=O)— bond, where R' is as defined herein.

A "urea" group refers to an —N(R')—C(=O)—NR"R'" group, where each of R' and R" is as defined herein, and R'" is defined as R' and R" are defined herein.

A "nitro" group refers to an —NO$_2$ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

A "phosphoric acid" is a phosphate group is which each of R is hydrogen.

The term "phosphinyl" describes a —PR'R" group, with each of R' and R" as defined hereinabove.

The term "thiourea" describes a —N(R')—C(=S)—NR"— group, with each of R' and R" as defined hereinabove.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

Chemical Syntheses:

All reactions requiring anhydrous conditions were performed under an Argon atmosphere. All reactions were carried out at room temperature unless stated otherwise.

Chemicals and solvents were either A.R. grade or purified by standard techniques.

Thin layer chromatography (TLC): silica gel plates Merck 60 $F_{254}$: compounds were visualized by irradiation with UV light.

Flash chromatography (FC): silica gel Merck 60 (particle size 0.040-0.063 mm), eluent given in parentheses.

$^1$H-NMR spectra were measured using Bruker Avance operated at 400 MHz as mentioned. $^{13}$C-NMR spectra were measured using Bruker Avance operated at 400 MHz as mentioned.

All general reagents, including salts and solvents, were purchased from Sigma-Aldrich.

Abbreviations:

AcOH—Acetic acid, DMF—Dimethylformamide, ACN—Acetonitrile, DCM—Dichloromethane, $Et_2O$—Diethyl ether, EtOAc—Ethylacetate, Hex-n-Hexanes, MeOH—Methanol, EtOH—Ethanol, $Ac_2O$—Acetic anhydride, $CHCl_3$—Chloroform, DMSO—Dimethylsulfoxide, TFA—Trifluoroacetic acid, HMTA—Hexamethylenetetramine.

In Vivo Experimental Methods:

Intravital Non-Invasive Imaging of Probe 4 Activation in Mice:

To induce acute inflammation in Balb/c mice, 1 ml (0.1 mg/ml) of LPS (Lipopolysaccharides from *Escherichia coli* 055:B5, Sigma) was injected into the peritoneal cavity of Balb/c mice as previously described [Lee, D. et al. *Nat. Mater.* 6, 765-769 (2007)]. Six hours later, additional i.p. injections of 400 μl of 1 mM of the tested probe compound or PBS (as control) were performed. Second control group of mice was injected i.p. with 1 ml of PBS followed by additional i.p. injection of 400 μl PBS. Fifteen minutes later, mice were anesthetized using ketamine (100 mg/kg) and xylazine (12 mg/kg), treated with a depilatory cream (Veet®), and placed inside CRI Maestro™ non-invasive fluorescence imaging system. Multispectral image-cubes were acquired through 600-800 nm spectral range in 10 nm steps using excitation (595 nm) and emission (635 nm longpass) filter set. Mice autofluorescence and undesired background signals were eliminated by spectral analysis and linear unmixing algorithm. Activated probe-fluorescence unmixed specific signal was quantified as total signal of photons/exposure time (sec). Data is expressed as mean±s.d.

Example 1

Cyanine-Like Probes with Turn-ON Mechanism

General Methodology

As indicated hereinabove, applying a Turn-ON mechanism based on changes in the pull-push conjugated π-electron system in cyanine dyes is more difficult than for other common fluorescent dyes, such as coumarin and fluorescein, since cyanine molecules have a polymethine π-electron system in between two nitrogen atoms that cannot be masked by a trigger.

In order to generate such a Turn-ON mechanism in cyanine molecules, a new methodology has been designed.

The designed methodology is based on a novel cyanine-like molecule, in which a functional group that can be masked is conjugated to a cyanine molecule. An exemplary conjugated cyanine-like molecule, Cy7-like molecule, is presented in FIG. 2A as Compound QCy7.

Cy7 is a known heptamethine cyanine dye, which is widely used for NIR imaging. The conjugated π-electron system of Cy7 has a positive charge that is delocalized between the two nitrogen atoms. Unlike Cy7, in the phenol Compound 1, the nitrogen atoms have two positive charges (one on each), and thus, the conjugation pattern is significantly different. As shown in FIG. 2A, deprotonation of phenol Compound 1, results in generation of phenolate Compound 1a. The negative charge of the phenolate can be delocalized towards one of the nitrogen atoms to form quinones 1b or 1c and thereby eliminating one positive charge. The obtained quinone derivative QCy7 (the resonance hybrid of species 1a, 1b and 1c) has now similar conjugation pattern to that of Cy7 and thus emits NIR fluorescence.

Various protecting groups can be conjugated to phenol Compound 1, so as to allow masking of the NIR fluorescence of QCy7 by a specific trigger moiety, which upon its removal, the free fluorophore (QCy7) will be obtained.

A variety of structurally and functionally related cyanine-like molecules can be prepared based on the above-described methodology, by, for example, replacing Cy7 by Cy5 or Cy9, by incorporating aromatic moieties other than phenol, by replacing the indolenine moiety (of a cyanine molecule) by one or more other acceptor moieties, and/or by incorporating more than two acceptor moieties in the molecule.

Exemplary cyanine-based NIR probes according to some embodiments of the present invention and their turn-ON mechanism are presented in FIGS. 2B-2H.

Exemplary synthetic pathways for obtaining exemplary NIR probes according to some embodiments of the present invention, starting from various phenol compounds to which acceptor moieties are couples, are presented in FIG. 3A. Generally, his- or tris-aldehyde phenolic compound (or any other bis- or tris-aldehyde aromatic compound with a suitable functionality), is condensed with two or more equivalents of an acceptor moiety or moieties.

As illustrated in FIG. 3A, the condensation of the phenol-dialdehyde Compound 2 with two equivalents of a general acceptor molecule affords a compound composed of a phenol moiety that functions as a latent donor in conjugation with two acceptors. Deprotonation of the phenol leads to formation of a phenolate active donor, which can now donate a pair of p-electrons to either one of the conjugated acceptors, to thereby generate a dye compound of the type QCy7, or an analog thereof (e.g., having different acceptor/donor moiety or being a QCy5 or other).

The donor moiety in the dye molecule can be replaced by other phenol derivatives. For example, phenol Compound 2a can be condensed with two equivalents of an acceptor molecule to afford dye compound of the type QCy9, while phenol 2b can be condensed with three equivalents of an acceptor molecule to produce a dye compound of the type QCy7/9. The acceptor molecules in each dye compound can be the same or different.

Exemplary acceptor moieties, according to some embodiments of the present invention are presented in FIG. 3B. Each of these acceptors can be present as one or both acceptors in the dye compounds of types QCy7 and QCy9 as presented in FIG. 3A, and as one, two or all of the acceptors of the dye compound of type QCy7/9 as presented in FIG. 3A.

Following the general methodology described herein, a series of compounds was synthesized, forming a library of new dye molecules with a donor-two-acceptors or donor-three-acceptors mechanism of action. The structures, and spectroscopic data obtained for the dye molecules synthesized are presented in Tables 1-3 hereinbelow.

Synthesis of QCy7:

QCy7 (see, FIG. 2) was synthesized by a simple two-step procedure as presented in Scheme 1 below. In brief, commercially available dialdehyde Compound 2 was condensed with 2 equivalents of indolium-iodide (Compound 8) to give ester Compound 3. The acetate group of Compound 3 was removed with potassium carbonate in methanol to afford QCy7.

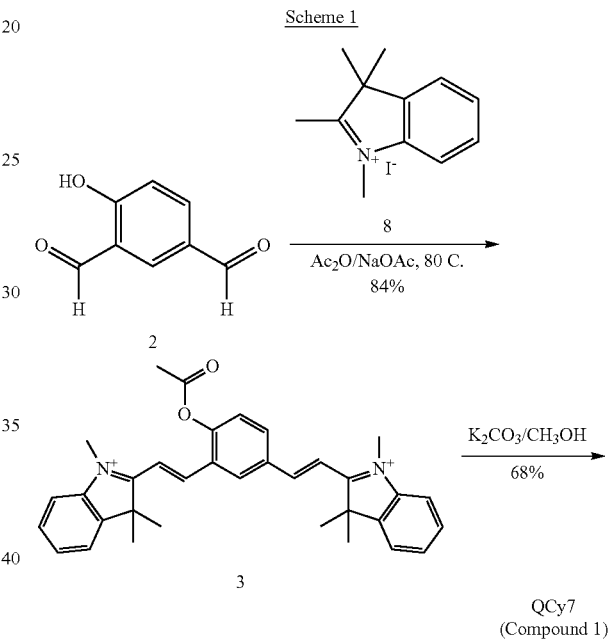

Scheme 1

Preparation of Compound 3:

A mixture of commercially available Compound 2 (50 mg, 0.33 mmol), NaOAc (83.9 mg, 1.02 mmol), and commercially available 1,2,3,3-tetramethyl-3H-indolium iodide (210.6 mg, 0.70 mmol) was dissolved in 2 ml Ac$_2$O. The reaction mixture stirred for 30 minutes at 80° C. under an Ar atmosphere and monitored by RP-HPLC (grad. 10%-90 ACN in water, 20 minutes). After completion, the solvent was evaporated under reduced pressure, and the crude product was dissolved in DCM, filtered and concentrated to give compound 3 (210 mg) as a red solid.

$^1$H NMR (400 MHz, CDCl$_3$+drope of MeOD): δ=9.63 (1H, s), 8.67 (1H, d, J=16.4 Hz), 8.52 (1H, d J=8.6 Hz), 8.27 (2H, m), 8.05 (1H, d, J=16.4 Hz), 7.62-7.70 (8H, m), 7.52 (1H, d, J=8.6 Hz), 4.54 (3H, s), 4.48 (3H, s), 2.49 (3H, s), 1.98 (6H, s), 1.88 (6H, s).

$^{13}$C NMR (400 MHz, CDCl$_3$+drope of MeOD): δ=183.89, 183.32, 186.77, 154.20, 152.68, 145.82, 144.41, 143.96, 142.03, 136.88, 133.39, 133.23, 131.40, 131.05, 130.56, 130.25, 127.94, 127.94, 124.73, 123.48, 117.40, 115.93, 115.58, 115.53, 53.85, 53.52, 38.40, 37.92, 30.31, 27.38, 27.12, 27.12, 21.93, 0.57.

MS (ESI): m/z calc. for $C_{34}H_{36}N_2O_2^{2+}$: 252.2. found: 252.2 $[M]^+$.

Preparation of QCy7:

Compound 3 (150 mg, 0.20 mmol) was dissolved in 6 ml MeOH. $K_2CO_3$ (27 mg, 0.20 mmol) was added to the suspension and the reaction mixture stirred at room temperature for 60 minutes, and monitored by RP-HPLC (grad. 10%-90 ACN in water, 20 minutes). After completion, the reaction mixture concentrated by evaporation under reduced pressure. The crude product was diluted with 6 ml $H_2O$, 1 ml AcOH, and purified by preparative RP-HPLC (grad. 10%-90 ACN in water, 20 minutes) to give QCy7 (80 mg, 68%) as an orange solid.

$^1$H NMR (400 MHz, $CDCl_3$): δ=8.91 (1H, s), 8.65 (1H, d, J=16.2 Hz), 8.28 (1H, d, J=15.9 Hz), 8.00 (1H, d, J=16.2 Hz), 7.82 (1H, d, J=8.5 Hz), 7.50-7.59 (9H, m), 7.40 (1H, d, J=8.5 Hz), 4.16 (3H, s), 4.14 (3H, s), 1.79 (6H, s), 1.76 (6H, s).

$^{13}$C NMR (400 MHz, $CDCl_3$): δ=183.85, 182.82, 168.52, 156.07, 151.79, 143.87, 143.63, 142.16, 142.07, 138.87, 135.42, 130.45, 130.14, 126.28, 123.63, 123.39, 123.30, 120.30, 114.83, 114.57, 112.77, 109.94, 53.14, 52.93, 34.90, 34.73, 27.57, 27.40, 0.70.

MS (ESI): m/z calc. for $C_{32}H_{33}N_2O^+$: 461.3. found: 461.3 $[M]^+$.

It is noted that the obtained QCy7 dye is converted to Compound 1 (its corresponding phenol) during prification by HPLC, presumably due to the presence of the acid in the eluent).

Nonetheless, it is to be noted that hereinthroughout, any of dye compounds as described herein are represented as their phenol tautomer, yet, are readily protonated in aqueous solutions having pH that is higher than the pKa of the phenol form. The phenol forms disclosed herein and the corresponding quinone forms ate therefore to be regarded as interchangeable.

Synthesis of Compound 9 (Also Denoted NK-118; Generating Dye Compound Sulfo-QCy7):

Compound 9 was synthesized similarly as described for QCy7 (see, Scheme 1 above and Schemes 6 and 7 below) by using indolium-3-propyl-sulfate (Compound 7) instead of indolium-iodide.

A mixture of Compound 2 (20 mg, 0.13 mmol), NaOAc (33.9 mg, 0.41 mmol), and Compound 7 (see, Scheme 7 below; 79 mg, 0.27 mmol) was dissolved in 1 ml $Ac_2O$. The reaction mixture stirred for 30 minutes at 80° C. under an Argon atmosphere and monitored by RP-HPLC (grad. 10%-90 ACN in water, 20 minutes). After completion, the reaction mixture was concentrated by evaporation under reduced pressure. The acetate derivative was dissolved in 4 ml MeOH. $K_2CO_3$ (catalytic amount) was added to the suspension and the reaction mixture was stirred at room temperature for 60 minutes, and monitored by RP-HPLC (grad. 10%-90 ACN in water, 20 minutes). After completion, the reaction mixture was diluted with 4 ml $H_2O$, 800 μL AcOH, and purified by preparative RP-HPLC (grad. 10%-90 ACN in water, 20 minutes) to give Sulfo-QCy7 (44 mg, 51% yield) as a red solid.

$^1$H NMR (400 MHz, DMSO-d6): δ=9.20 (1H, s), 8.52-8.59 (3H, m), 8.17 (1H, d, J=16.3 Hz), 8.07 (1H, d, J=7.30 Hz), 8.01 (1H, d, J=7.30 Hz), 7.90 (1H, d, J=7.2 Hz), 7.86 (1H, d, J=7.2 Hz), 7.61-7.68 (4H, m), 7.21 (4H, m, J=8.7 Hz), 4.97 (2H, t, J=7.6 Hz), 4.92 (2H, t, J=7.6 Hz), 2.75 (2H, t, J=6.0 Hz), 2.71 (2H, t, J=6.0 Hz), 2.23-2.28 (4H, m), 1.86 (6H, s), 1.83 (6H, s).

$^{13}$C NMR (400 MHz, DMSO-d6): δ=183.07, 182.91, 164.26, 154.78, 147.93, 145.07, 144.95, 142.12, 142.05, 137.97, 135.54, 130.36, 130.39, 130.27, 128.28, 124.25, 124.19, 123.41, 116.41, 116.07, 114.54, 112.23, 53.28, 53.21, 48.29, 48.28, 46.83, 46.47, 27.45, 27.20, 25.77.

MS (ESI): m/z calc. for $C_{36}H_{39}N_2O_7S_2$: 675.8. found: 675.4 $[M]^-$.

Using similar synthetic methodologies, a library of cyanine-like compounds, having various acceptor moieties, donor moieties and combinations thereof has been prepared. The following describes some exemplary syntheses.

General Procedure for Preparing Cyanine-Like Compounds Comprising a Picolinium Acceptor Moiety:

A mixture of dialdehyde (e.g., 0.067 mmol), piperidine (1-2 mol equivalents), and a picolinium compound (1-2 molequivalents) was dissolved in EtOH. The reaction mixture was stirred for 30 minutes at 80° C. under an Ar atmosphere, while monitoring the reaction progress by RP-HPLC (using a gradient eluent of 10-90% ACN in water, 20 minutes). Once the reaction was completed, the reaction mixture was concentrated by evaporation under reduced pressure. The crude product was diluted with 1:1:0.1 $H_2O$:ACN:AcOH, and was purified by preparative RP-HPLC (using a gradient eluent of 10-90% ACN in water, 20 minutes) to give the desired product.

The most basic picolinium compound used is picolinium iodide:

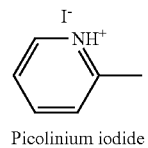

Picolinium iodide

Synthesis of Compound 26:

An exemplary picolinium derivative, Compound 26 was prepared as depicted in Scheme 2 below.

Scheme 2

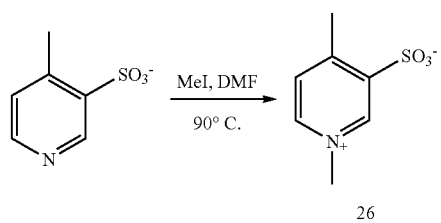

4-methylpyridine-3-sulfonate (0.51 mmol) was dissolved in 2 ml DMF. Iodomethane (5.1 mmol) was added to the suspension and the reaction mixture was stirred at 90° C. overnight, EtOAc was thereafter added and the product precipitated. The obtained solid was filtered to give Compound 26 (90% yield) as a brown solid.

$^1$H NMR (400 MHz, MeOD): δ=9.09 (1H, s), 8.77 (1H, d, J=6.1 Hz), 7.97 (1H, d, J=6.1 Hz), 4.40 (3H, s), 2.99 (3H, s).

$^{13}$C NMR (400 MHz, MeOD): δ=158.41, 145.86, 144.78, 143.55, 130.63, 47.73, 20.39.

MS (ESI): m/z calc. for $C_7H_9NO_3S$: 187.03. found: 210.0 $[M+Na]^+$.

Synthesis of Compound 10 (Entry 2 in Table 1):

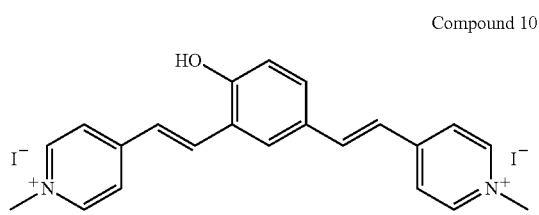

Compound 10

A mixture of commercially available 4-hydroxyisophtalaldehyde (0.067 mmol), piperidine (0.133 mmol) and picolinium iodide (0.133 mmol) was reacted according to general procedure described hereinabove to give Compound 10 (70% yield) as a yellow solid.

$^1$H NMR (400 MHz, MeOD): δ=8.71-8.65 (4H, m), 8.17-8.11 (5H, m), 7.91 (1H, d, J=16.2 Hz), 7.90 (1H, d, J=16.4 Hz), 7.72-7.62 (2H, m), 7.37 (1H, d, J=16.2 Hz), 7.00 (1H, d, J=8.4 Hz), 4.32 (3H, s), 4.29 (3H, s).

$^{13}$C NMR (400 MHz, MeOD): δ=155.06, 154.86, 145.38, 145.22, 141.76, 137.12, 132.25, 130.10, 128.88, 127.98, 124.25, 124.08, 123.93, 123.43, 121.06, 118.98, 117.28.

MS (ESI): m/z calc. for $C_{22}H_{21}N_2O^+$: 329.16. found: 329.2 $[M]^+$.

Synthesis of Compound 11 (Entry 3 in Table 1):

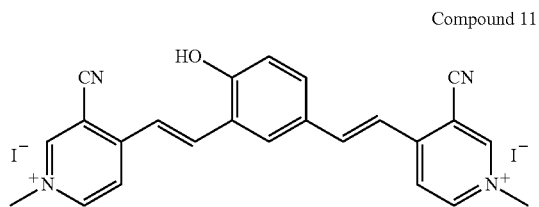

Compound 11

A mixture of commercially available 4-hydroxyisophtalaldehyde (0.066 mmol), piperidine (0.133 mmol) and a 3-cyano-1,4-dimethylpyridinium iodide (0.133 mmol) was reacted according to the general procedure described herein to give Compound 11 (40% yield) as a green solid. The structure was verified by NMR.

Synthesis of Compound 12 (Entry 4 in Table 1):

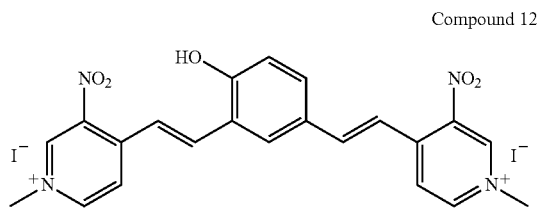

Compound 12

A mixture of commercially available 4-hydroxyisophtalaldehyde (0.066 mmol), piperidine (0.133 mmol) and 1,4-dimethyl-3-nitropyridinium iodide (0.133 mmol) was reacted according to the general procedure described herein to give Compound 11 (40% yield). The structure was verified by NMR.

Synthesis of Compound 13 (Entry 5 in Table 1):

A mixture of commercially available 4-hydroxyisophtalaldehyde (0.066 mmol), piperidine (0.133 mmol) and 4-methyl-1-N-methylquinolinium iodide (0.133 mmol) was reacted according to the general procedure described hereinabove to give Compound 13 (90% yield) as a brown solid. The structure was verified by NMR.

Synthesis of Compound 14 (Entry 6 in Table 1):

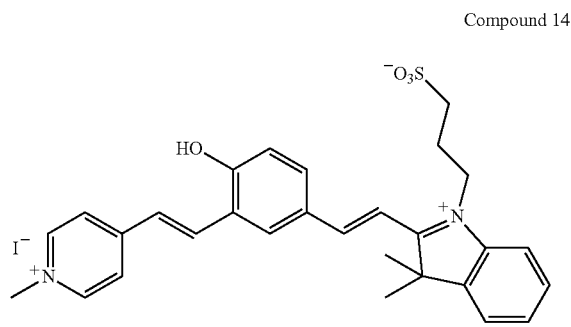

Compound 14

A mixture of commercially available 4-hydroxyisophtalaldehyde (0.20 mmol), piperidine (0.21 mmol) and picolinium iodide (0.21 mmol) was reacted according to the general procedure described hereinabove. The reaction mixture was concentrated by evaporation under reduced pressure and the crude product was further reacted without purification (0.20 mmol) with piperidine (0.21 mmol) and Compound 7 (0.21 mmol) in EtOH (1.5 ml). The reaction mixture stirred for 60 minutes at 80° C. under an Ar atmosphere while being monitored by RP-HPLC (using a gradient eluent of 10-90% ACN in water, 20 minutes). Once the reaction was completed, the reaction mixture was concentrated by evaporation under reduced pressure. The crude product was diluted with 1:1:0.1 $H_2O$:ACN:AcOH, and purified by preparative RP-HPLC (using a gradient eluent of 10-90% ACN in water, 20 minutes) to give Compound 14 (80% yield) as a red solid. The structure was verified by NMR.

Synthesis of Compound 15 (Entry 7 in Table 1):

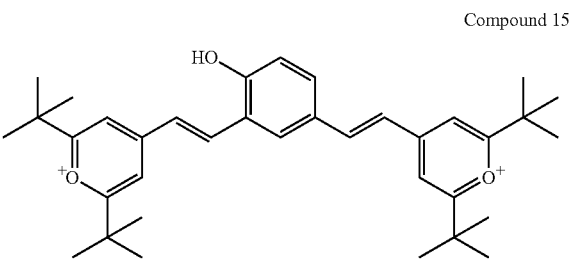

Compound 15

A mixture of commercially available 4-hydroxyisophtalaldehyde (0.066 mmol) and 2,6-ditert-butyl-4-methylpyrylium trifluoromethanesulfonate (0.133 mmol) was reacted according to the general procedure described hereinabove, to give Compound 15 (80% yield) as a brown red solid. The structure was verified by NMR.

Synthesis of Compound 16 (Entry 8 in Table 1):

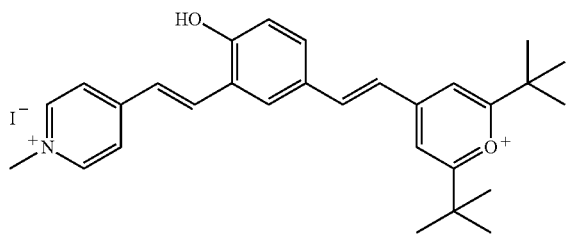

Compound 16

A mixture of commercially available 4-hydroxyisophtalaldehyde (0.066 mmol), 2,6-ditert-butyl-4-methylpyrylium trifluoromethanesulfonate (0.066 mmol) and picolinium iodide (0.066 mmol) was reacted according to the general procedure described hereinabove, to give Compound 16. The structure was verified by NMR.

Synthesis of Compound 17 (Entry 9 in Table 1):

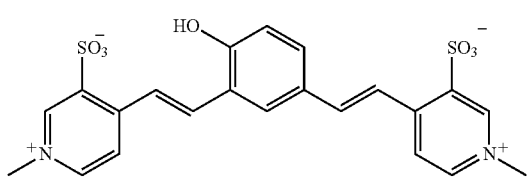

Compound 17

A mixture of commercially available 4-hydroxyisophtalaldehyde (0.066 mmol), piperidine (0.133 mmol) and Compound 26 (0.133 mmol) was reacted according to general procedure described hereinabove to give Compound 17 (75% yield) as a yellow solid.

$^1$H NMR (400 MHz, DMSO): δ=8.71-8.65 (4H, m), 8.17-8.11 (5H, m), 7.91 (1H, d, J=16.2 Hz), 7.90 (1H, d, J=16.4 Hz), 7.72-7.62 (2H, m), 7.37 (1H, d, J=16.2 Hz), 7.00 (1H, d, J=8.4 Hz), 4.32 (3H, s), 4.29 (3H, s).

$^{13}$C NMR (400 MHz, MeOD): δ=155.06, 154.86, 145.38, 145.22, 141.76, 137.12, 132.25, 130.10, 128.88, 127.98, 124.25, 124.08, 123.93, 123.43, 121.06, 118.98, 117.28.

Synthesis of Compound 18 (Entry 10 in Table 1):

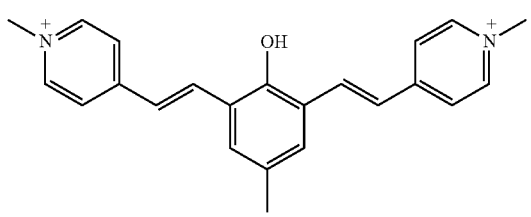

Compound 18

A mixture of Compound 2c (0.06 mmol; see, FIG. 3A), piperidine (0.12 mmol) and picolinium iodide (0.12 mmol) was reacted according to general procedure described hereinabove, to give Compound 18 (87% yield) as an orange solid.

$^1$H NMR (400 MHz, CDCl$_3$+MeOD): δ=8.61-8.72 (4H, m), 8.19 (2H, d, J=15.3 Hz), 8.18-8.22 (4H, m), 7.47 (2H, s), 7.15 (2H, d, J=15.3 Hz), 4.29 (6H, s), 2.65 (3H, s).

$^{13}$C NMR (400 MHz, CDCl$_3$+MeOD): δ=154.93, 144.99, 137.96, 131.25, 130.69, 129.34, 124.74, 124.65, 121.41, 45.06, 23.12.

MS (ESI): m/z calc. for C$_{23}$H$_{23}$N$_2$O$^+$: 343.18. found: 343.2 [M]$^+$.

Synthesis of Compound 2d (a Phenyl Dialdehyde):

A mixture of commercially available ethyl-4-hydroxy benzoate (6 mmol) and HMTA (24.8 mmol) was dissolved in TFA (7 ml). The reaction mixture was refluxed overnight using dean stark system, and was thereafter cooled to room temperature. 40 ml of water were added and the reaction was heated to 80° C. for 2 hours. After cooling to room temperature the product precipitated as a yellow solid (quantitative yield).

$^1$H NMR (400 MHz, CDCl$_3$+MeOD): δ=10.22 (2H, s), 8.59 (2H, s), 4.34 (2H, q, J=7.1 Hz), 1.37 (3H, t, J=7.1 Hz).

$^{13}$C NMR (400 MHz, CDCl$_3$+MeOD): δ=192.56, 165.17, 139.53, 136.54, 135.71, 123.59, 62.42, 14.94. MS (ESI): m/z calc. for C$_{11}$H$_{10}$O$_5$: 222.05. found: 221.1 [M]$^-$.

Synthesis of Compound 19 (Entry 11 in Table 1):

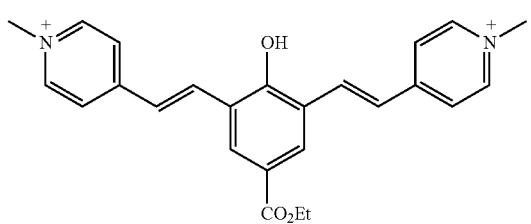

Compound 19

A mixture of dialdehyde Compound 2d (0.06 mmol), piperidine (0.12 mmol) and picolinium iodide (0.12 mmol) was reacted according to the general procedure described herein to give Compound 19 (90% yield) as a yellow solid.

$^1$H NMR (400 MHz, MeOD): δ=8.74 (4H, d, J=6.6 Hz), 8.39 (2H, s), 8.22 (2H, d, J=16.3 Hz), 8.18 (4H, d, J=6.6 Hz), 7.48 (2H, d, J=16.3 Hz), 4.40 (2H, q, J=7.1 Hz), 4.33 (6H, s), 1.42 (3H, t, J=7.1 Hz).

$^{13}$C NMR (400 MHz, MeOD): δ=166.40, 159.51, 154.38, 145.55, 135.79, 131.19, 125.21, 124.63, 123.60, 61.76, 47.17, 14.01. MS (ESI): m/z calc. for C$_{25}$H$_{25}$N$_2$O$_3$$^+$: 401.19. found: 401.2 [M]+.

Synthesis of Compound 20 (Entry 12 in Table 1):

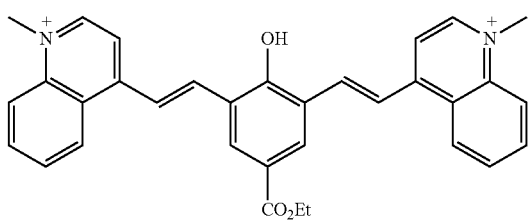

Compound 20

A mixture of dialdehyde Compound 2d (0.06 mmol), piperidine (0.12 mmol) and 4-methyl-N-methylquinolinium iodide (0.12 mmol) was reacted according to the general procedure described herein to give Compound 20 (60% yield) as a brown solid.

$^1$H NMR (400 MHz, CDCl$_3$+MeOD): δ=9.25 (2H, d, J=6.3 Hz), 8.62 (2H, d, J=8.4 Hz), 8.44 (2H, d, J=6.3 Hz), 8.32 (2H, s), 8.29 (2H, d, J=15.9 Hz), 8.19 (2H, d, J=8.4 Hz), 8.13 (2H, t, J=6.9 Hz), 8.09 (2H, d, J=15.9 Hz), 7.95 (2H, t, J=6.9 Hz), 4.58 (6H, s), 4.43 (2H, q, J=7.1 Hz).

$^{13}$C NMR (400 MHz, MeOD): δ=165.96, 159.48, 153.90, 147.89, 139.18, 137.00, 135.32, 131.31, 129.62, 127.03, 126.12, 124.96, 122.83, 121.53, 118.74, 116.64, 61.28, 44.32, 13.43.

MS (ESI): m/z calc. for $C_{33}H_{29}N_2O_3^+$: 501.22. found: 501.2 [M]$^+$.

Synthesis of Compound 21 (Entry 13 in Table 1):

Compound 21

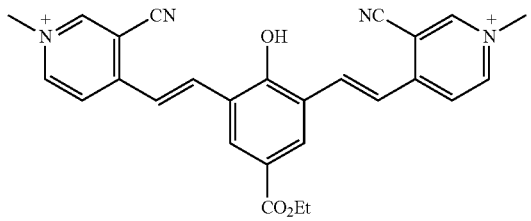

A mixture of dialdehyde Compound 2d (0.06 mmol), piperidine (0.12 mmol) and N-methyl-3-cyano-4-methylpyridinium iodide (0.12 mmol) was reacted according to the general procedure described herein to give Compound 21 (50% yield) as a green-blue solid.

$^1$H NMR (400 MHz, MeOD): δ=9.35 (2H, s), 8.84 (2H, d, J=6.7 Hz), 8.53 (2H, d, J=6.7 Hz), 8.43 (2H, d, J=15.9 Hz), 8.40 (2H, s), 7.86 (2H, d, J=15.9 Hz), 4.42 (2H, q, J=7.1 Hz), 4.33 (6H, s), 1.41 (3H, t, J=7.1 Hz).

$^{13}$C NMR (400 MHz, MeOD): δ=162.43, 162.08, 150.60, 147.12, 146.67, 142.67, 134.09, 122.75, 121.79, 118.95, 118.00, 117.58, 116.04, 61.76, 47.90, 14.01.

MS (ESI): m/z calc. for $C_{27}H_{23}N_4O_3^+$: 451.18. found: 451.2 [M]$^+$.

Synthesis of Compound 22 (Entry 14 in Table 1):

Compound 22

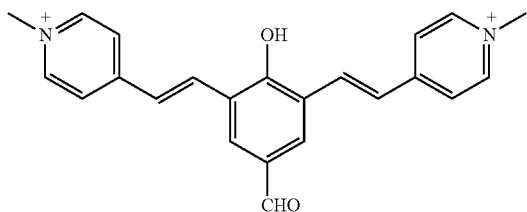

A mixture of trialdehyde Compound 2b (0.06 mmol), piperidine (0.12 mmol) and picolinium iodide (0.12 mmol) was reacted according to general procedure described herein at room temperature to give Compound 22 (90% yield) as a red brown solid. The structure was confirmed by NMR.

Synthesis of Compound 23 (Entry 15 in Table 1):

Compound 23

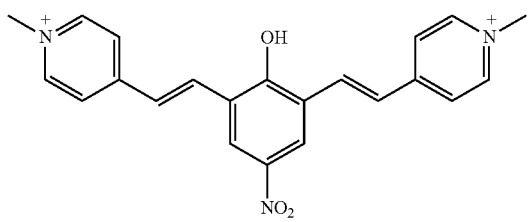

A mixture of (2-hydroxy-5-nitro-1,3-phenylene)dimethanol (0.50 mmol) and MnO$_2$ (3.5 mmol) was dissolved in 2 ml EtOAc and the reaction was refluxed for 24 hours while being monitored by TLC (using EtOAc/Hexane 30:70 as eluent). The reaction mixture, once completed, was concentrated by evaporation under reduced pressure. The crude product was purified by column chromatography on silica gel (using EtOAc/Hexane 30:70 as eluent) to give 2-hydroxy-5-nitroisophthalaldehyde (40% yield) as a yellow solid.

A mixture of 2-hydroxy-5-nitroisophthalaldehyde (0.06 mmol), piperidine (0.12 mmol) and picolinium iodide (0.12 mmol) was reacted according to the general procedure described herein to give Compound 23 (35% yield) as an orange solid.

$^1$H NMR (400 MHz, DMSO): δ=8.84 (4H, d, J=6.7 Hz), 8.56 (2H, s), 8.25 (2H, d, J=6.7 Hz), 8.04 (4H, d, J=16.5 Hz), 7.71 (2H, d, J=16.5 Hz), 4.20 (6H, s).

$^{13}$C NMR (400 MHz, DMSO): δ=164.03, 153.62, 146.37, 135.42, 127.99, 126.74, 126.04, 124.97, 123.68, 48.14.

Synthesis of Compound 24 (Entry 16 in Table 1):

Compound 24

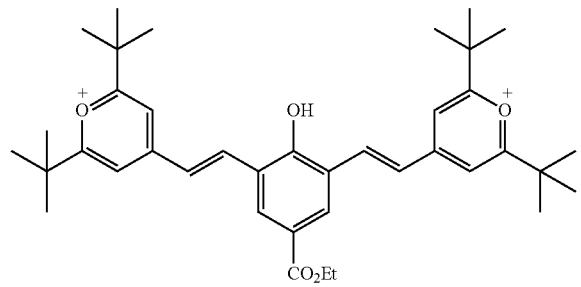

A mixture of dialdehyde Compound 2d (0.06 mmol), piperidine (0.12 mmol) and 2,6-ditert-butyl-4-methylpyrylium trifluoromethanesulfonate (0.133 mmol) was reacted according to the general procedure described hereinabove, to give Compound 24. The structure was verified by NMR.

Synthesis of Compound 27 (Entry 17 in Table 1):

Compound 27

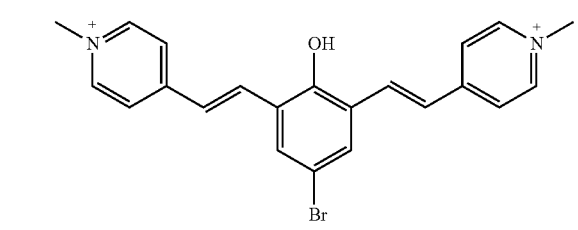

A mixture of 4-hydroxyisophtalaldehyde (0.06 mmol; Compound 2f), piperidine (0.12 mmol) and picolinium iodide (0.12 mmol) was reacted according to the general procedure described herein to give Compound 27 (83% yield) as an orange solid.

$^1$H NMR (400 MHz, MeOD): δ=8.74 (4H, d, J=6.8 Hz), 8.15-8.19 (6H, m), 7.96 (2H, s), 7.47 (2H, d, J=16.2 Hz), 4.33 (6H, s).

$^{13}$C NMR (400 MHz, MeOD): δ=154.33, 145.58, 141.73, 135.15, 132.24, 127.53, 125.29, 124.61, 113.74 47.16.

MS (ESI): m/z calc. for $C_{22}H_{20}N_2OBr^+$: 407.08. found: 407.1 [M]$^+$.

Synthesis of Compound 28 (Entry 18 in Table 1):

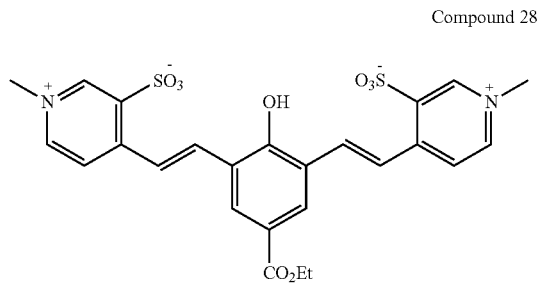

Compound 28

A mixture of dialdehyde Compound 2d (0.06 mmol), piperidine (0.12 mmol) and Compound 26 (0.12 mmol) was reacted according to the general procedure described herein to give Compound 28 (78% yield) as a yellow solid.

$^1$H NMR (400 MHz, DMSO): δ=9.15 (2H, s), 8.89 (2H, d, J=6.6 Hz), 8.54 (2H, d, J=6.6 Hz), 8.41 (2H, d, J=16.2 Hz), 8.27 (2H, s), 8.19 (2H, d, J=16.2 Hz), 4.42 (2H, q, J=7.1 Hz), 4.36 (6H, s), 1.41 (3H, t, J=7.1 Hz).

$^{13}$C NMR (400 MHz, DMSO): δ=151.32, 145.60, 144.68, 143.92, 136.38, 132.25, 126.34, 125.92, 125.47, 123.92, 122.14, 62.22, 48.16, 15.43.

MS (ESI): m/z calc. for $C_{25}H_{24}N_2O_9S_2$: 560.09. found: 561.1 $[M+H]^+$.

Synthesis of Compound 29:

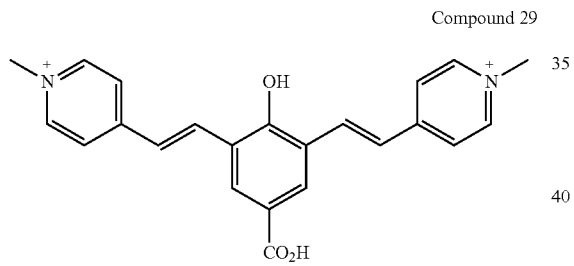

Compound 29

A mixture of commercially available 4-hydroxybenzoic acid (7.2 mmol) and HMTA (29.8 mmol) were dissolved in TFA (7.6 ml). The reaction was refluxed for 3 days using a Dean-Stark system, and was thereafter cooled to room temperature. 44 ml of water were added and the resulting mixture was heated to 80° C. for 4 hours. Cooling to room temperature yielded 3,5-diformyl-4-hydroxybenzoic acid (Compound 2g) as a yellow solid (in quantitative yield).

$^1$H NMR (400 MHz, DMSO): δ=10.25 (2H, s), 8.50 (2H, s). $^{13}$C NMR (400 MHz, DMSO): δ=193.11, 166.70, 157.61, 138.75, 124.75, 123.78.

A mixture of the dialdehyde, 5-diformyl-4-hydroxybenzoic acid (0.06 mmol), piperidine (0.12 mmol) and picolinium iodide (0.12 mmol) was reacted according to the general procedure described herein at room temperature to give Compound 29 (40% yield) as a green solid.

$^1$H NMR (400 MHz, MeOD): δ=8.74 (4H, d, J=6.8 Hz), 8.45 (2H, s), 8.25 (2H, d, J=16.2 Hz), 8.19 (4H, d, J=6.8 Hz), 7.52 (2H, d, J=16.2 Hz), 4.33 (6H, s).

$^{13}$C NMR (400 MHz, MeOD): δ=167.43, 158.89, 153.81, 144.89, 135.24, 130.91, 124.59, 124.45, 123.93, 123.29, 46.48.

Synthesis of Compound 30 (Entry 20 in Table 1):

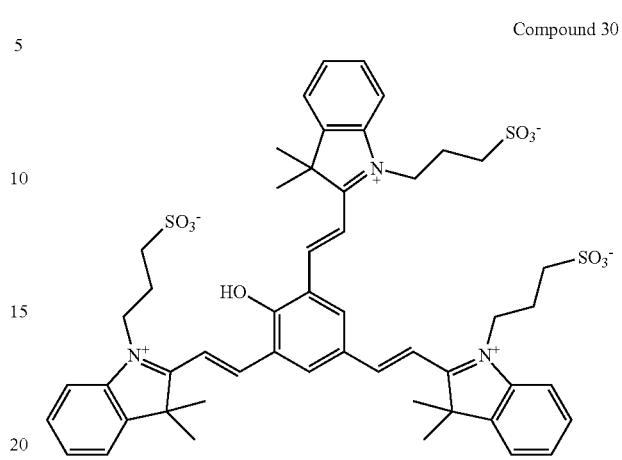

Compound 30

A mixture of trialdehyde Compound 2b (0.056 mmol), piperidine (0.168 mmol), and Compound 7 (0.168 mmol) was reacted according to the general procedure described herein to give Compound 30. The structure was verified by NMR.

Synthesis of Compound 31 (Entry 22 in Table 1):

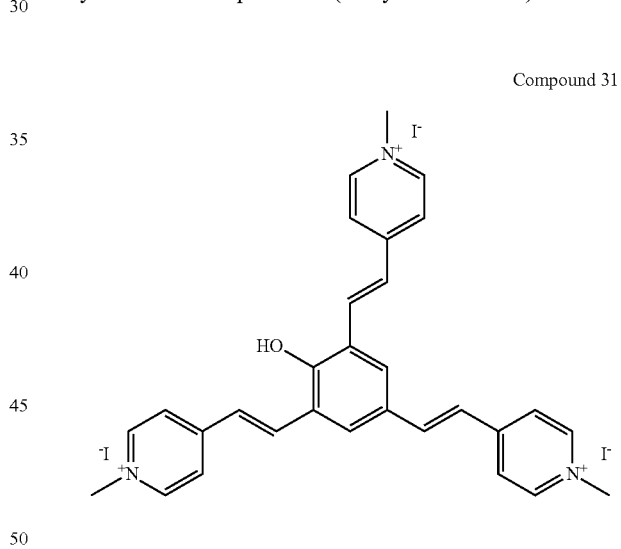

Compound 31

A mixture of trialdehyde Compound 2b (0.056 mmol), piperidine (0.168 mmol), and picolinium iodide (0.168 mmol) was reacted according to the general procedure described herein to give Compound 31 (50% yield) as a red solid.

$^1$H NMR (400 MHz, MeOD): δ=8.75 (4H, d, J=6.6 Hz), 8.72 (2H, d, J=6.6 Hz), 8.27 (2H, d, J=16.2 Hz), 8.18-8.23 (6H, m), 8.15 (2H, d, J=6.7 Hz), 7.95 (1H, d, J=16.3 Hz), 7.58 (2H, d, J=16.2 Hz), 7.52 (1H, d, J=16.3 Hz), 4.34 (6H, s), 4.32 (3H, s).

$^{13}$C NMR (400 MHz, MeOD): δ=154.49, 154.47, 145.60, 145.44, 140.95, 135.94, 130.08, 128.93, 126.00, 125.14, 124.55, 124.18, 122.54, 47.17, 17.06.

Synthesis of Compound 25 (Entry 21 in Table 1):

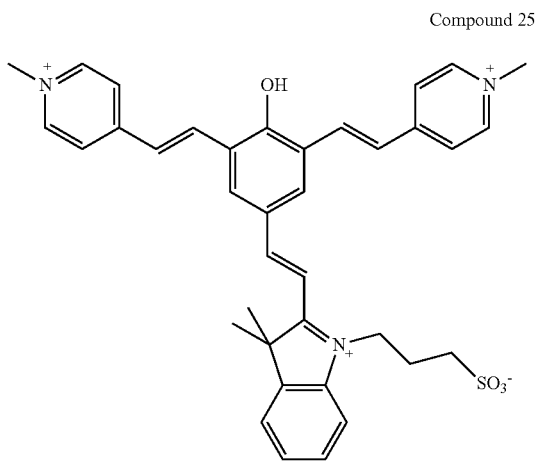

Compound 25

A mixture of trialdehyde Compound 2b (0.06 mmol), piperidine (0.12 mmol) and picolinium iodide (0.12 mmol) was reacted according to the general procedure. described herein. Once completed, the reaction mixture was concentrated by evaporation under reduced pressure, yielding Compound 22 as described herein. The crude product was further reacted without purification (0.20 mmol) with piperidine (0.21 mmol) and Compound 7 (0.21 mmol) according to the general procedure described hereinabove to give Compound 25 (50% yield) as a blue solid.

$^1$H NMR (400 MHz, MeOD): δ=8.69 (4H, d, J=6.5 Hz), 8.65 (2H, m), 8.43 (1H, d, J=15.8 Hz), 8.26-8.22 (6H, m) 7.94 (1H, d, J=15.8 Hz), 7.88 (2H, d, J=16.3 Hz), 7.81 (1H, d, J=7.7 Hz), 7.73 (1H, d, J=6.4 Hz), 7.563-7.57 (2H, m), 4.86 (2H, m), 4.31 (6H, s), 3.12 (2H, m), 2.43 (2H, m).

$^{13}$C NMR (400 MHz, MeOD): δ=180.91, 154.43, 154.21, 144.67, 143.37, 140.96, 135.33, 133.17, 129.18, 128.66, 126.51, 125.33, 124.11, 123.84, 22.65, 113.69, 108.70, 51.77, 46.32, 44.55, 25.72, 23.84, 23.29.

Synthesis of Compound 32 (Entry 23 in Table 1):

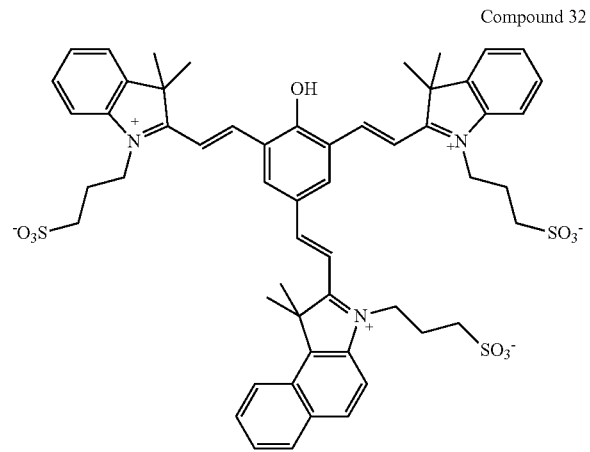

Compound 32

A mixture of crude Compound 22 (0.06 mmol, obtained as described hereinabove for Compound 25), piperidine (0.07 mmol) and indolium Compound 33 (0.07 mmol) was reacted according to the general procedure described herein, to give Compound 32 (40% yield) as a blue solid.

$^1$H NMR (400 MHz, MeOD): δ=8.75-8.73 (6H, m), 8.57 (1H, d, J=16.2 Hz), 8.41 (1H, d, J=8.6 Hz), 8.31-8.23 (7H, m), 8.15 (1H, d, J=8.2 Hz), 8.11 (2H, d, J=16.2 Hz), 8.04 (1H, d, J=8.9 Hz), 7.90 (2H, d, J=16.2 Hz), 7.81 (1H, t, J=7.3 Hz), 7.71 (1H, t, J=7.3 Hz), 4.87 (2H, t, J=9.9 Hz), 4.34 (6H, s), 3.17 (2H, m), 2.53 (2H, m).

$^{13}$C NMR (400 MHz, MeOD): δ=183.30, 154.50, 153.75, 145.50, 139.34, 138.90, 134.95, 132.71, 132.12, 130.70, 128.92, 128.06, 127.81, 126.55, 125.77, 124.76, 123.42, 112.72, 111.02, 54.59, 47.12, 45.86, 26.04, 24.96, 23.55.

MS (ESI): m/z calc. for $C_{41}H_{40}N_3O_4S^+$: 670.27. found: 670.3 $[M]^+$.

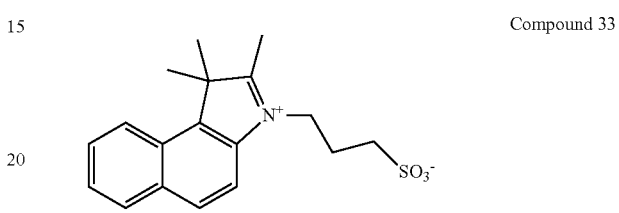

Compound 33

Example 2

Spectral Properties of Dye Compounds

Characterization of the Spectral Properties of QCy7:

Compound 1 (which generates the dye compound QCy7 deprotonation) was obtained as an orange crystalline powder. FIGS. 4A and 4B present the UV-Vis spectrum of Compound 1 (FIG. 4A), compared to that of the acetate Compound 3 (FIG. 4B). The UV-Vis spectrum of the dye QCy7 generated from Compound 1 exhibits two absorption peaks with maximum at 460 nm and 570 nm (FIG. 4A). As expected, the fluorescence spectrum indeed shows emission peak in the NIR region at a wavelength of 715 nm. The obtained large stokes shift between the excitation and the emission wavelengths of about 150 nm is a desirable feature for fluorescence probes, which assists in increasing the signal-to-noise ratio. As predicted, the acetate derivative of phenol Compound 1 did not show any fluorescence emission in the NIR region (FIG. 4B, blue plot). Since acetate Compound 3 is a masked derivative of Compound 1 which does not generate QCy7 upon simple deprotonation in an aqueous solution, it can be used to model the fluorescence activity of a probe with a specific trigger.

Quantum Yield Calculation for QCy7:

Cresyl-violet-perchlorate (as presented hereinbelow) was chosen as a reference compound for the determination of QCy7 quantum yield. This compound exhibits similar spectral properties such as, absorbance around 560 nm and fluorescence at the region of 600-740 nm.

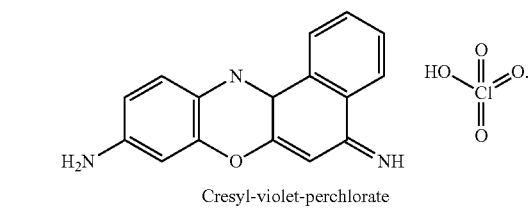 [SMILES: N=C1C=C2Oc3cc(N)ccc3NC2c2ccccc21 ; [O-][Cl+3]([O-])([O-])O]

Cresyl-violet-perchlorate

FIG. 5 presents the data obtained for fluorescence intensity vs. wavelength of standard sample (Cresyl violet; FIG. 5A), and test sample (QCy7; FIG. 5B), at the indicated concentrations. The measurements were performed in a 1 cm cuvette using Fluoromax-3 fluorometer; at an excitation wavelength of 560 nm. Cresyl violet was dissolved in methanol and Compound 1 in PBS 7.4 (just generating QCy7).

FIG. 6 presents linear plots of (Cresyl violet; FIG. 6A) and QCy7 (FIG. 6B).

Conversion to the absolute quantum yield is achieved through the following equation:

$$\Phi_X = \Phi_{ST}(\text{Grad}_X/\text{Grad}_{ST})(\eta^2_X/\eta^2_{ST})$$

where the subscripts ST and X denote standard and test respectively, $\Phi$ is the fluorescence quantum yield, Grad the gradient from the plot of integrated fluorescence intensity vs. absorbance (see, FIG. 6), and $\eta$ the refractive index of the solvents. $\Phi_{Cresyl-violet}$=0.55 [Stefan et al. (1992) J. Phys. Chem. 86, 1738-1742].

$$\Phi_{QCy7} = 0.55\left(\frac{20668866}{170479123}\right) \cdot \left(\frac{1.333^2}{1.314^2}\right) = 0.069$$

Extinction Coefficient Calculations:

FIG. 7 presents linear plots of QCy7 as measured at 1 cm cuvette, at the indicated concentrations in PBS 7.4, at the maximum wavelength of QCy7 (560 nm).

$$\epsilon_{QCy7} = 26848 \ [M^{-1}cm^{-1}]$$

Characterization of the Spectral Properties of Sulfo-QCy7:

Sulfo-QCy7 presented similar spectroscopic behavior to that of QCy7 with NIR fluorescence maxima at wavelength of 720 nm, as presented in FIG. 8.

FIG. 9 presents linear plots of QCy7 (FIG. 9A) and Sulfo-QCy7 (FIG. 9B).

The absolute quantum yield was calculated as described hereinabove and found to be:

$$\Phi_{Sulfo-QCy7} = 0.069\left(\frac{397654}{176082}\right) = 0.16$$

Extinction Coefficient Calculations:

FIG. 10 presents linear plots of Sulfo-QCy7 as measured at 1 cm cuvette, at the indicated concentrations in PBS 7.4, at the maximum wavelength of Sulfo-QCy7 (590 nm).

$$\epsilon_{Sulfo-QCy7} = 52235 \ [M^{-1}cm^{-1}]$$

The quantum yield (16%) and the extinction coefficient (52,000 mol$^{-1}$ cm$^{-1}$) of sulfo-QCy7 have high values that are adequate for in vivo measurements.

FIG. 11 presents the absorption (blue) and fluorescence (red) of Compound 14 (Table 1, Entry 6).

Compound 14 is composed from a phenol latent donor and two different acceptors; a picolinium moiety and an indolium moiety (see, Scheme 3). Deprotonation of the phenolic dye leads to formation of new donor-acceptor pair fluorochrome. As shown in FIG. 11, the UV-Vis spectrum exhibits a major absorption peak with maximum at 550 nm and the fluorescence spectrum shows emission peak in the NIR region at a wavelength of 680 nm.

The quantum yield of Compound 14 was calculated as 17%.

Scheme 3

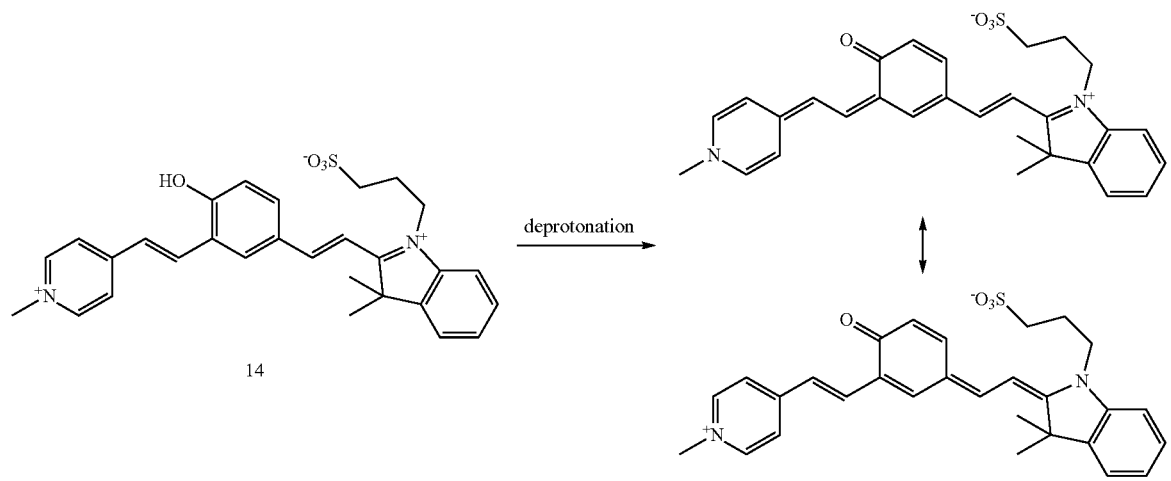

QCy7 was chosen as a reference compound for the determination of Sulfo-QCy7 quantum yield.

FIG. 8 presents the data obtained for fluorescence intensity vs. wavelength of standard sample (QCy7; FIG. 8A), and test sample (Sulfo-QCy7, generated from Compound 9; FIG. 8B), at the indicated concentrations. The measurements were performed at a 96-wells plate reader using Fluoromax-3 fluorometer; at an excitation wavelength of 560 nm. Both samples were dissolved in PBS 7.4.

FIG. 12 presents the absorption (blue) and fluorescence (red) of Compound 17 (Table 1, Entry 10).

Compound 18 is composed of a phenol latent donor and two identical acceptors based on a picolinium moiety (see, Scheme 4). Deprotonation of the phenolic form leads to formation of new donor-acceptor pair fluorochrome. The UV-Vis spectrum exhibits two absorption peaks with maximum at 330 nm and 490 nm and the fluorescence spectrum shows emission peak in the NIR region at a wavelength of 670 nm.

The quantum yield of Compound 18 was calculated as 5%.

Scheme 4

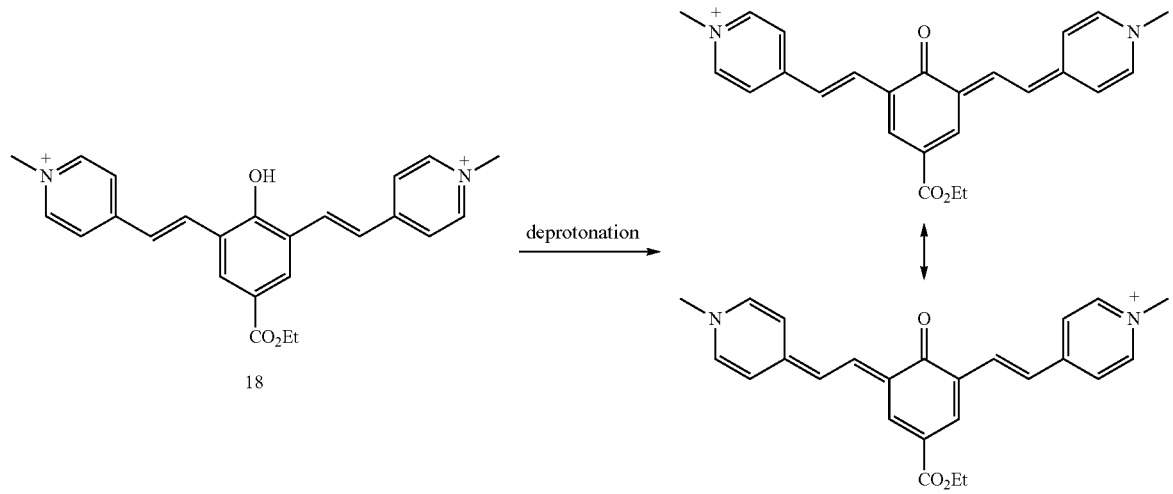

FIG. 13 presents the absorption (blue) and fluorescence (red) of Compound 25 (Table 1, Entry 21).

Compound 25 is composed of a phenol latent donor and three acceptors; two picolinium moieties and one indolium moiety (see, Scheme 5). Deprotonation of the phenolic compound leads to formation of three resonance donor-two-acceptor structures of new fluorochrome. The UV-Vis spectrum exhibits two absorption peaks with maximum at 330 nm and 550 nm and the fluorescence spectrum shows emission peak in the NIR region at a wavelength of 680 nm.

The quantum yield of Compound 25 was calculated as 16%.

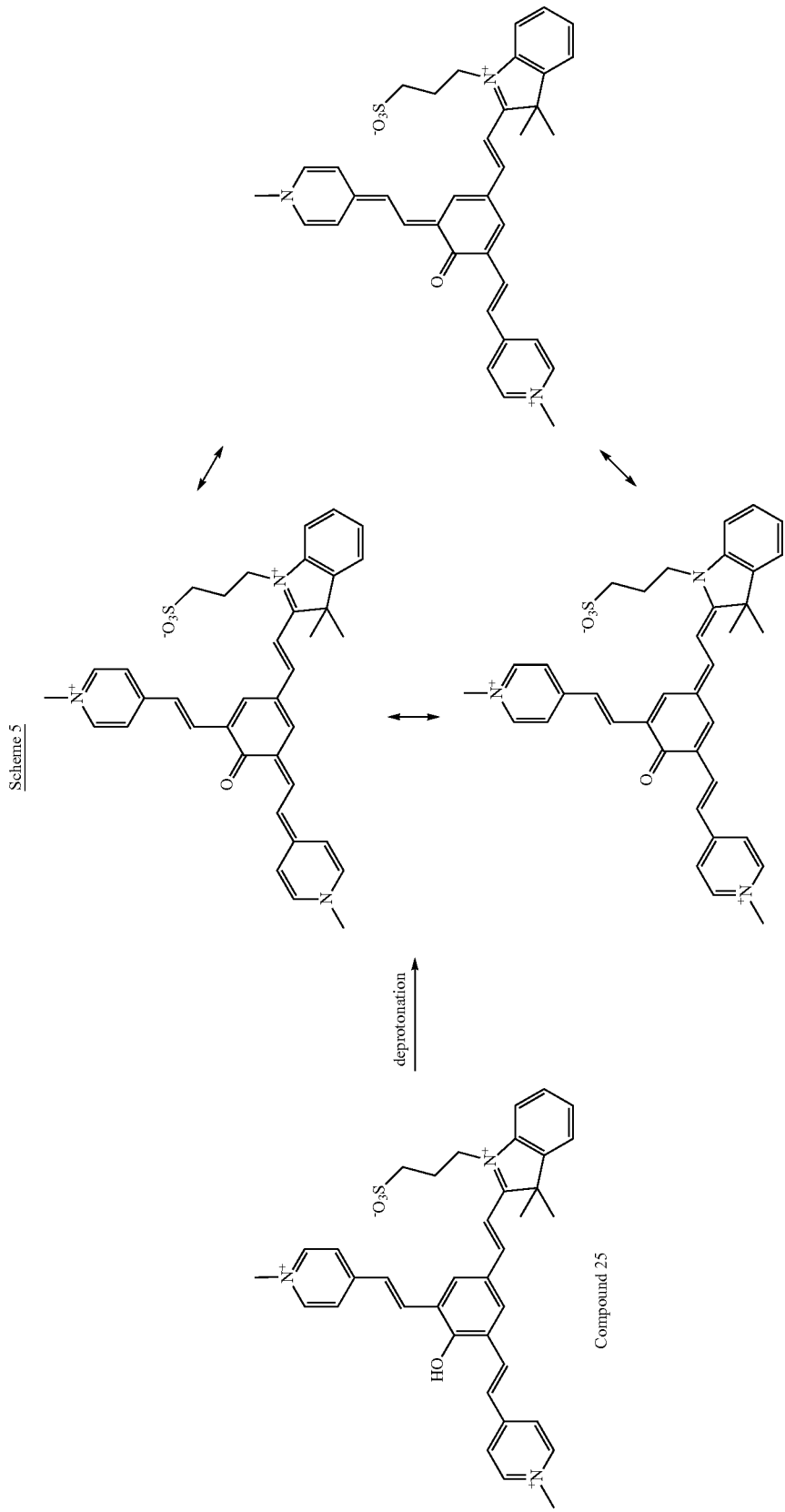

Compound 30 (Table 1, Entry 16) also exhibited a quantum yield of 16%.

Compounds 17, 27 and 29 (Table 1, Entries 9, 17 and 19, respectively) exhibited a quantum yield of 2.6%, 2.9% and 2%, respectively. Compounds 22 and (Table 1, Entries 14 and 23, respectively) exhibited a quantum yield of 7% and 6%, respectively.

The chemical 2D structures and spectroscopic data obtained for exemplary dye molecules according to embodiments of the present invention are presented in Table 1.

Entries 1-9 in Table 1 represent the structures and data obtained for dye Compounds 9-17 prepared from phenol Compound 2; Entries 10-19 represent the structures and data obtained for dye Compounds 18-24 and 27-29 prepared from phenol Compound 2a or its substituted derivatives phenol Compounds 2c, 2d, 2e, 2f and 2g; and Entries 20-24 represent the structures and data obtained for dye Compounds 25 and 30-32 prepared from phenol Compound 2b.

TABLE 1

| Entry | Compound No. | Dye structure | Donor | Acceptor | λmax | λmax |
|---|---|---|---|---|---|---|
| 1 | 9 | | | | 460 nm 590 nm | 710 nm |
| 2 | 10 | | | | 350 nm 420 nm 500 nm | 720 nm |
| 3 | 11 | | | | 350 nm 500 nm 570 nm | 730 nm |
| 4 | 12 | | | | 350 nm | No fluorescence |
| 5 | 13 | | | | 550 nm | No fluorescence |

TABLE 1-continued

| Entry | Compound No. | Dye structure | Donor | Acceptor | λmax | λmax |
|---|---|---|---|---|---|---|
| 6 | 14 | (structure) | (structure) 2 | (structures) | 450 nm 550 nm | 650 nm |
| 7 | 15 | (structure) | (structure) 2 | (structure) | 520 nm 580 nm 620 nm | No fluorescence |
| 8 | 16 | (structure) | (structure) 2 | (structures) | 580 nm | 730 nm |
| 9 | 17 | (structure) | (structure) 2 | (structure) | 350 nm 475 nm 540 nm | 730 nm |
| 10 | 18 | (structure) | (structure) 2c | (structure) | 350 nm 540 nm | 720 nm |
| 11 | 19 | (structure) | (structure) 2d | (structure) | 320 nm 490 nm | 660 nm |

TABLE 1-continued

| Entry | Compound No. | Dye structure | Donor | Acceptor | λmax | λmax |
|---|---|---|---|---|---|---|
| 12 | 20 | | 2d | | 390 nm 550 nm | No fluorescence |
| 13 | 21 | | 2d | | 360 nm 550 nm | 730 nm |
| 14 | 22 | | 2b | | 330 nm 470 nm | 650 nm |
| 15 | 23 | | 2e | | 390 nm 430 nm | 600 nm |
| 16 | 24 | | 2d | | 475 nm 650 nm | No fluorescence |
| 17 | 27 | | 2f | | 340 nm 530 nm | 720 nm |

TABLE 1-continued

| Entry | Compound No. | Dye structure | Donor | Acceptor | λmax | λmax |
|---|---|---|---|---|---|---|
| 18 | 28 | | 2d | | 300 nm 350 nm 530 nm | 720 nm |
| 19 | 29 | | 2g | | 350 nm 510 nm | 700 nm |
| 20 | 30 | | 2b | 7 | 460 nm 590 nm | 710 nm |
| 21 | 25 | | 2b | | 550 nm | 650 nm |
| 22 | 31 | | 2b | | 350 nm 420 nm 500 nm | 720 nm |

TABLE 1-continued

| Entry | Compound No. | Dye structure | Donor | Acceptor | λmax | λmax |
|---|---|---|---|---|---|---|
| 23 | 32 | (structure) | (structure 2b with CHO, HO, OHC, CHO groups) | (two indole-based acceptor structures with SO$_3^-$) | 350 nm 550 nm | 660 nm |

The Stokes shifts between the excitation and the emission wavelengths of about 150-200 nm, obtained for most of the dye compounds, are significantly larger than observed for the known cyanines like Cy5 and Cy7 (10-20 nm). The increased Stokes shift is a desirable feature for fluorescence probes, which assists in increasing the signal-to-noise ratio.

Fluorescent dyes, which absorb at wavelengths of 350-550 nm, can be excited in NIR region with a two-photon laser. This option enables to apply the advantages of NIR excitation for chromphores that do not absorb in the NIR range. To demonstrate the potential of the library of dye compounds as described herein to undergo a two-photon excitation with a NIR laser, Compound 25 was evaluated.

Compound 25 was incubated with HeLa cells and PBS 7.4. As can be seen in FIGS. 14A and 14B, Compound 25 exhibits a two-photon excitation spectrum in wavelengths between 800-1000 nm, thus indicating that it can be used to provide confocal cell images.

Thus, it is shown herein that the methodology described herein enables to prepare a library of fluorogenic compounds and fluorescent compounds generated therefrom which offer vast flexibility for choosing a dye compound with desired characteristics.

Example 3

Characterization of Cyanine-Like Compounds in Aqueous Solution

Aqueous Stability:

The aqueous stability of the cyanine-like dye compound presented herein was tested and compared to that of the cyanine molecule Cy7.

All tested compounds were incubated in PBS 7.4 [25 µM], at 37° C., and their NIR fluorescent emission was monitored over 72 hours. FIG. 15 presents the normalized intensity of NIR fluorescent emission of dyes generated from Compound 9 (green circles; Sulfo-QCy7), Compound 14 (blue diamonds), Compound 18 (red squares), Compound 25 (orange triangles) and Compound 1 (blank navy squares; QCy7) as a function of incubation time. Three dyes presented increase aqueous stability than that of Cy7 (Compounds 14, 18 and 25), while Compound 9 showed similar stability. Compounds 14 and 18 were found to be highly stable and did not show any loss of NIR fluorescence during the whole incubation period.

pKa Measurements:

As illustrated in FIG. 2A, the intramolecular charge transfer (ICT) from the phenolate-donor to one of the two acceptors moieties leads to formation of a new fluorochrome with NIR fluorescence. Importantly, the protonated form of the dyes (as a phenol structure) does not emit fluorescence in the NIR region. These compounds can therefore be used as NIR fluorescent probes for determination of pH in aqueous solution in the region of the pKa value of the phenols. The type of the acceptors moieties, present in the dye molecule, affects the pKa of each phenol.

The pKa values of exemplary compounds according to some embodiments of the present invention, Compounds 14, 18 and 25, was measured by monitoring their UV-Vis absorbance as a function of the environment pH. The tested compounds, at a concentration of 50 µM were dissolved in the respective buffers at the indicated pH and their absorbance was measured.

FIG. 16 presents the data obtained and show that the phenols of Compounds 14, 18 and 25 are characterized by pKa values of 2.9, 4.3 and 5.4, respectively.

The relative low pKa values indicate that these compounds will undergo an ICT (intramolecular charge transfer) mode of action under physiological conditions, so as to emit NIR fluorescence, since at physiological pH deprotonation will occur and the fluorescent compounds will be generated.

Example 4

Cell Permeability

Fluorogenic probes are often used for imaging of various biological functions. Fluorogenic compounds which are cell permeable could efficiently generate in-vitro fluorescent images. Thus, the cell permeability of the compounds described herein was tested.

HeLa cells were incubated overnight with Compound 9 in PBS 7.4, and the cells was thereafter imaged by confocal microscope.

FIG. 17A presents confocal image of the cells. FIG. 17B presents the fluorescence intensity vs. wavelength of Sulfo- QCy7, generated from Compound 9 (NK-118) inside (green) and outside the cells, indicating the higher fluorescence inside the cells.

A colocalization assay of Compound 25 was conducted with the lysosome marker lysosensor. Sample was excited with a 561 nm laser line and fluorescence acquired from 570 nm to 800 nm.

Figures 18A, 18B, 18C:

FIGS. 18A-C show confocal images of HeLa cells incubated with Compound 25. The accumulation of the dye in the lisosomal vesicles indicates cell-penetration through endocytosis mechanism. As expected, the dye emitted NIR fluorescence even under the acidic condition of the lysosome (pH of about 5).

Figures 18D, 18E, 18F:
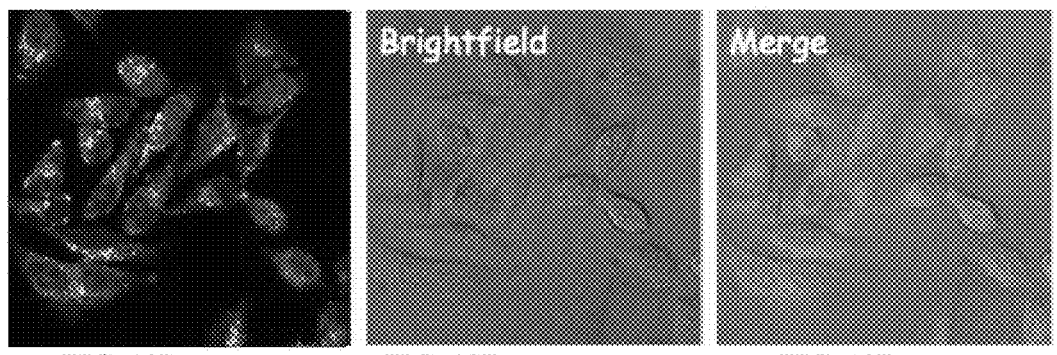

To further demonstrate the ability of the fluorophore for NIR in vitro imaging, cells were incubated with Compound 25 for overnight, washed and imaged with a confocal microscope. The obtained images are shown in FIG. 18D-F, and show the NIR fluorescence emitted by the dye, indicating its chemical stability after overnight in cell-medium.

Example 5

Cyanine-Based Probes Having Hydrogen Peroxide-Sensitive Triggering Moiety

An exemplary diagnostic probe was designed and prepared based on the above-described NIR fluorophore.

It is well-known that inflammation events lead to oxidative stress and over production of hydrogen peroxide, which can damage living tissues. Thus, the development of optical probes that can image hydrogen peroxide in vivo is a major challenge in the field of molecular imaging. There are numerous reports in the scientific literature that describe development and evaluation of such imaging probes [Dickinson et al. *J. Am. Chem. Soc.* 132, 5906-15 (2010); Dickinson et al. *Nat. Chem. Biol.* 7, 106-12 (2011); Miller et al. *Nat. Chem. Biol.* 3, 263-7 (2007); Van de Bittner et al. *Proc. Natl. Acad. Sci.* (2010)], most of them are based on boronic acid/ester as a specific masking group that can be removed upon reaction with hydrogen peroxide [Avital-Shmilovici, M. & Shabat, D. *Biorg. Med. Chem.* 18, 3643-7 (2010); Sella et al. *J. Am. Chem. Soc.* 132, 3945-52 (2010); Sella, E. & Shabat, D. *Chem. Commun.*, 5701-3 (2008); and Sella, E. & Shabat, D. *J. Am. Chem. Soc.* 131, 9934-6 (2009)].

Preparation of a QCy7-Based System with a Phenylboronic Acid Trigger Unit:

Accordingly, a molecular probe which has a phenylboronic acid trigger unit attached through a self-immolative linkage to a derivative of QCy7 has been designed. Scheme 6 depicts molecular probe Compound 4, which has phenylboronic acid attached through an ether-linkage to a sulfonated derivative of QCy7. The purpose of sulfonated alkyl-chains is to increase the aqueous solubility and to prevent aggregation of the relatively hydrophobic QCy7 molecules. Probe Compound 4 is designed such that incubation with hydrogen peroxide under physiological conditions results in oxidation of the phenylboronic acid, followed by hydrolysis and 1,6-elimination of p-quinone-methide to release the active fluorophore sulfo-QCy7, as depicted in Scheme 6.

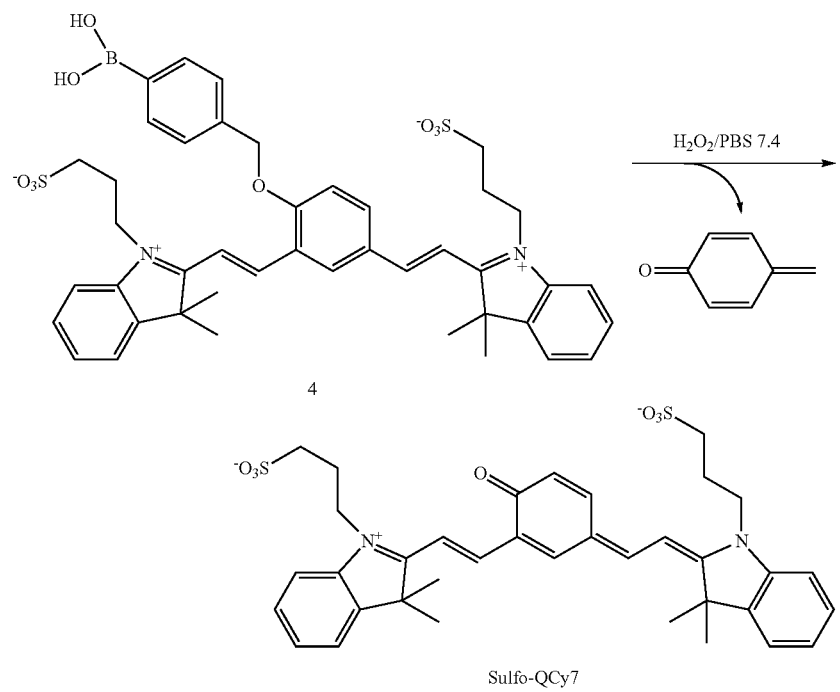

Scheme 6

Probe Compound 4 was synthesized as depicted in Scheme 7. In brief, dialdehyde Compound 2 was alkylated with previously synthesized benzyl-iodide Compound 5 [see, Sella, E. & Shabat, D. *Chem. Commun.*, 5701-3 (2008)], to generate ether Compound 6. The aldehydes groups of Compound 6 were condensed with of indolium-propane-sulfate (Compound 7) to give probe Compound 4.

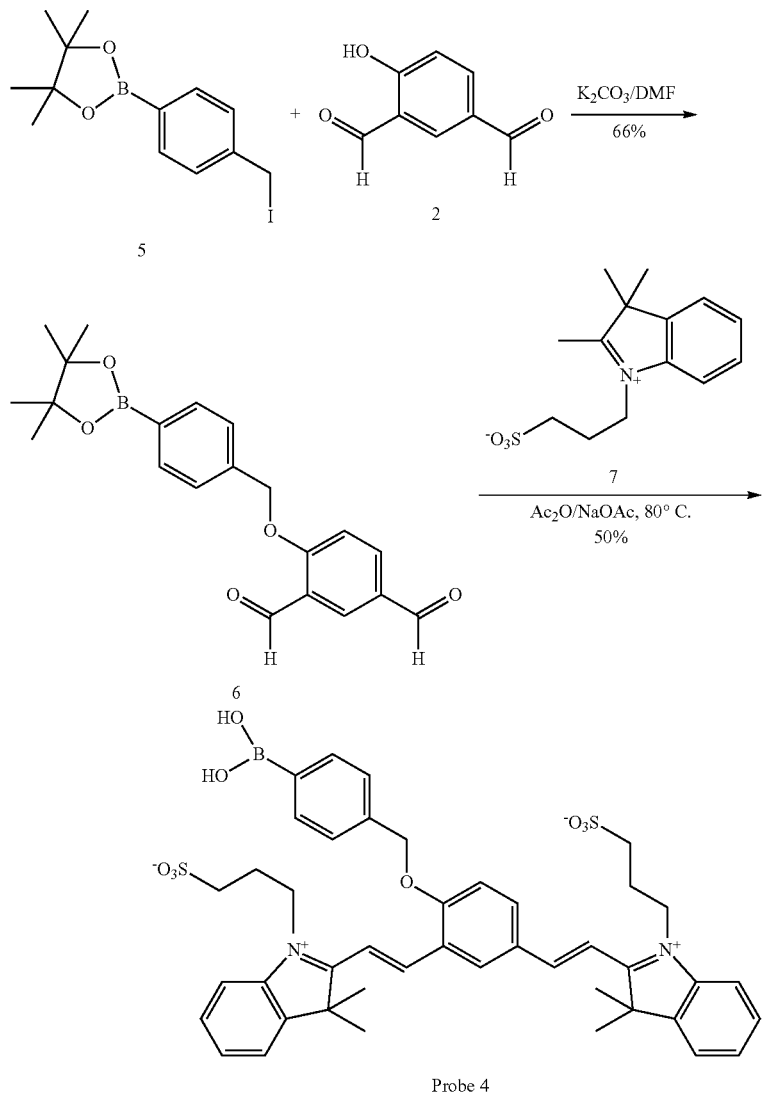

Scheme 7

Probe 4

Synthesis of Compound 6:

Compound 2 (50 mg, 0.33 mmol) was dissolved in 1 ml dry DMF and cooled to 0° C. $K_2CO_3$ (101 mg, 0.73 mmol) was added and the solution stirred at 0° C. for 10 minutes, before Compound 5 (229 mg, 0.66 mmol) was added. The reaction mixture was stirred for 12 hours at room temperature and monitored by TLC (EtOAc/Hex 30:70). After completion, the reaction mixture was diluted with $Et_2O$, and was washed with saturated solution of $NH_4Cl$. The organic layer was separated, washed with brine, dried over $MgSO_4$, and evaporated under reduced pressure. The crude product was purified by column chromatography on silica gel (EtOAc/Hex 30:70) to give Compound 6 (80 mg, 66%) as a white solid.

$^1$H NMR (400 MHz, $CDCl_3$): δ=10.55 (1H, s), 9.93 (1H, s), 8.35 (1H, s), 8.07 (1H, d, 8.7 Hz), 7.86 (2H, d, 7.7 Hz), 7.44 (2H, d, 7.7 Hz), 7.17 (1H, d, 8.7 Hz), 5.32 (2H, s), 1.35 (12H, s).

$^{13}$C NMR (400 MHz, $CDCl_3$): δ=190.81, 189.19, 165.62, 138.68, 136.31, 136.05, 132.59, 130.59, 127.21, 125.90, 114.40, 84.72, 71.74, 25.59.

MS (ESI): m/z calc. for $C_{21}H_{23}BO_5$: 366.2. found: 389.2 [M+Na]$^+$.

Synthesis of Probe Compound 4:

A mixture of Compound 6 (23 mg, 0.06 mmol), NaOAc (11.3 mg, 0.13 mmol), and compound 7 [Mason et al. (2005) *J. Org. Chem.* 70, 2939-49] (39 mg, 0.13 mmol) was dissolved in 1 ml $Ac_2O$. The reaction mixture stirred for 30 minutes at 80° C. under an Argon atmosphere and monitored by RP-HPLC (grad. 10%-90 ACN in water, 20 minutes). After completion, the reaction mixture was concentrated by evaporation under reduced pressure. The crude product was diluted with 1.5 ml $H_2O$, 1.5 ml ACN, 300 μL AcOH, and purified by preparative RP-HPLC (grad. 10%-90 ACN in water, 20 min) to give probe Compound 4 (23 mg, 68%) as a orange solid.

$^1$H NMR (400 MHz, DMSO-d6): δ=9.25 (1H, s), 8.54-8.65 (3H, m), 8.18 (1H, d J=16.5 Hz), 8.00-8.10 (4H, m), 7.85-7.89 (4H, m), 7.60-7.66 (4H, m), 7.53-7.56 (3H, m), 5.50 (2H, s), 4.94 (4H, t, J=6.8 Hz), 2.70 (4H, m), 2.24 (4H, m), 1.85 (6H, s), 1.74 (6H, s).

$^{13}$C NMR (200 MHz, DMSO-d6): δ=182.41, 182.18, 162.02, 153.57, 153.35, 146.74, 144.44, 144.16, 141.25, 138.16, 137.77, 134.79, 133.37, 130.06, 129.66, 129.43, 128.74, 126.97, 124.35, 123.43, 123.39, 115.78, 115.50, 115.24, 114.91, 114.80, 112.76, 112.53, 71.37, 52.70, 52.47, 47.56, 46.20, 45.85, 26.50, 26.68, 25.10

MS (ESI): m/z calc. for $C_{34}H_{47}BN_2O_9S_2$: 810.3. found: 809.4 [M−H]$^-$.

Characterization of the Spectral Properties of Sulfo-QCy7 and Probe 4:

FIG. 19A (right vial) shows the typical cyan color for a solution of Compound 9 (generating sulfo-QCy7) obtained in PBS 7.4. Expectedly due to the 150 nm blue stokes shift, the masked form of sulfo-QCy7, probe 4 had a yellow color in aqueous solution (FIG. 19A, left vial). When placed under NIR imaging camera, a solution of probe 4 is clearly transparent while the solution of Compound 9 (generating sulfo-QCy7) exhibits well-observed NIR fluorescence (see, FIG. 19B).

NIR Fluorescence Assays:

In order to evaluate the NIR fluorescence obtained by probe Compound 4 upon reaction with hydrogen peroxide under physiological conditions, the probe was incubated in PBS 7.4 at 37° C., in the presence and absence of hydrogen peroxide at varying concentrations, and the emitted NIR fluorescence was measured by a spectrophotometer (M2 of Molecular Device). The results, presented in FIG. 20A, indicate full conversion of probe Compound 4 to sulfo-QCy7 within 30 minutes (red plot). No NIR fluorescence is observed in the absence of hydrogen peroxide (blue plot).

The sensitivity of probe Compound 4 towards detection of hydrogen peroxide was then evaluated. FIG. 20B shows that the probe can straightforwardly detect hydrogen peroxide concentrations below 1 µM.

Example 6

In Vivo Studies Utilizing a Cyanine-Based Probe System with a Phenylboronic Acid Trigger Unit Since the overproduction of hydrogen peroxide in vivo is concerned with the development of numerous inflammatory diseases, the ability of the above-described Turn-ON NIR-probe to image endogenously produced hydrogen peroxide in a mice model was investigated, as described hereinabove.

Initially, as a simple control experiment, a premixed solution of probe 4 with hydrogen peroxide was injected into the peritoneal cavity, and the mice were imaged in a CRI Maestro™ non-invasive fluorescence imaging system.

The obtained images are presented in FIG. 21, and clearly show that exogenously activated probe Compound 4 can generate NIR fluorescence in vivo image. Mice treated only with the probe or with the buffer did not show any detectable NIR fluorescence.

Next, it was tested whether probe Compound 4 can be used to differentiate in vivo various concentrations of hydrogen peroxide in order to test the system's sensitivity. Therefore, two different concentrations of hydrogen peroxide were premixed with probe Compound 4; immediately injected intramuscularly, into the leg, and then imaged by the CRI Maestro™ non-invasive fluorescence imaging system.

The obtained images are presented in FIG. 22, and show that the intensity of the NIR emitted fluorescence from probe Compound 4 was indeed dependent on the hydrogen peroxide initial concentration.

The, the use of probe Compound 4 for visualizing endogenously-produced hydrogen peroxide was tested. To this end, a previously described model of acute inflammation in mice that can be simply induced by lipopolysaccharide (LPS) was used [Lee et al. *Nat. Mater.* 6, 765-9 (2007)]. Mice were injected intraperitoneally (i.p.) with LPS (1 ml of 0.1 mg/ml), followed 6 hours later by additional i.p. injection of probe Compound 4 (400 µl of 1 mM) and were thereafter imaged by the CRI Maestro™ non-invasive fluorescence imaging system.

The obtained images and associated data are presented in FIGS. 23A and 23B, respectively, and show that mice treated with LPS and with LPS and probe Compound 4 generated a significantly greater intensity of NIR fluorescence signal compared with non-LPS treated mice injected with probe 4 or PBS. The slight NIR fluorescence observed in mice treated only with probe Compound 4 is attributed to basal levels of hydrogen peroxide produced in living animals. The signal-to-noise ratio of the NIR fluorescence intensity observed by the hydrogen peroxide imaging probe in mice was about 10-fold higher compared with the control group. Such a high ratio of a Turn-ON probe has never been observed heretofore for an in vivo hydrogen peroxide imaging probe. Such ratio is adequate to obtain strong contrast image.

The use of a boronate triggering group to mask various fluorophores has been previously successfully practiced for detection and imaging of hydrogen peroxide. It has been shown that boronate-based probes are highly selective to hydrogen peroxide among several other reactive oxygen species [See, Dickinson et al. *J. Am. Chem. Soc.* 132, 5906-15 (2010)]. The data presented herein corroborates the previous reports and demonstrate the capability of the designed probes to image biological processes in vivo, while using hydrogen peroxide as an exemplary analyte.

Example 7

Cathepsin B-Activated Cyanine-Based Probes

Based on the design presented in FIG. 2, a turn-ON probe that is activated by cathepsin B was prepared. An exemplary such probe is constructed of the dipeptide Z-Phe-Lys attached to Compound 1 through a short self-immolative linker, as depicted in FIG. 24A. The dipeptide is a known substrate of cathepsin B and upon its cleavage and 1,6-elimination of the p-amino-benzylalcohol (PABA) linker, QCy7 is released. According to the previously described mode of action, the NIR fluorescence of probe Compound 34 should be in an OFF position when attached to the dipeptide and thus in an ON position upon exposure to cathepsin B.

The synthesis of probe 34 is illustrated in Scheme 8. Z-Phe-Lys-PABA 35 is reacted with tetra-bromomethane and triphenylphosphine to generate iodide 36. Dialdehyde Compound 2 is alkylated with iodide 36 to give dialdehyde 37, which is then condensed with 2 equivalents of indolium-iodide to yield probe Compound 34.

Scheme 8

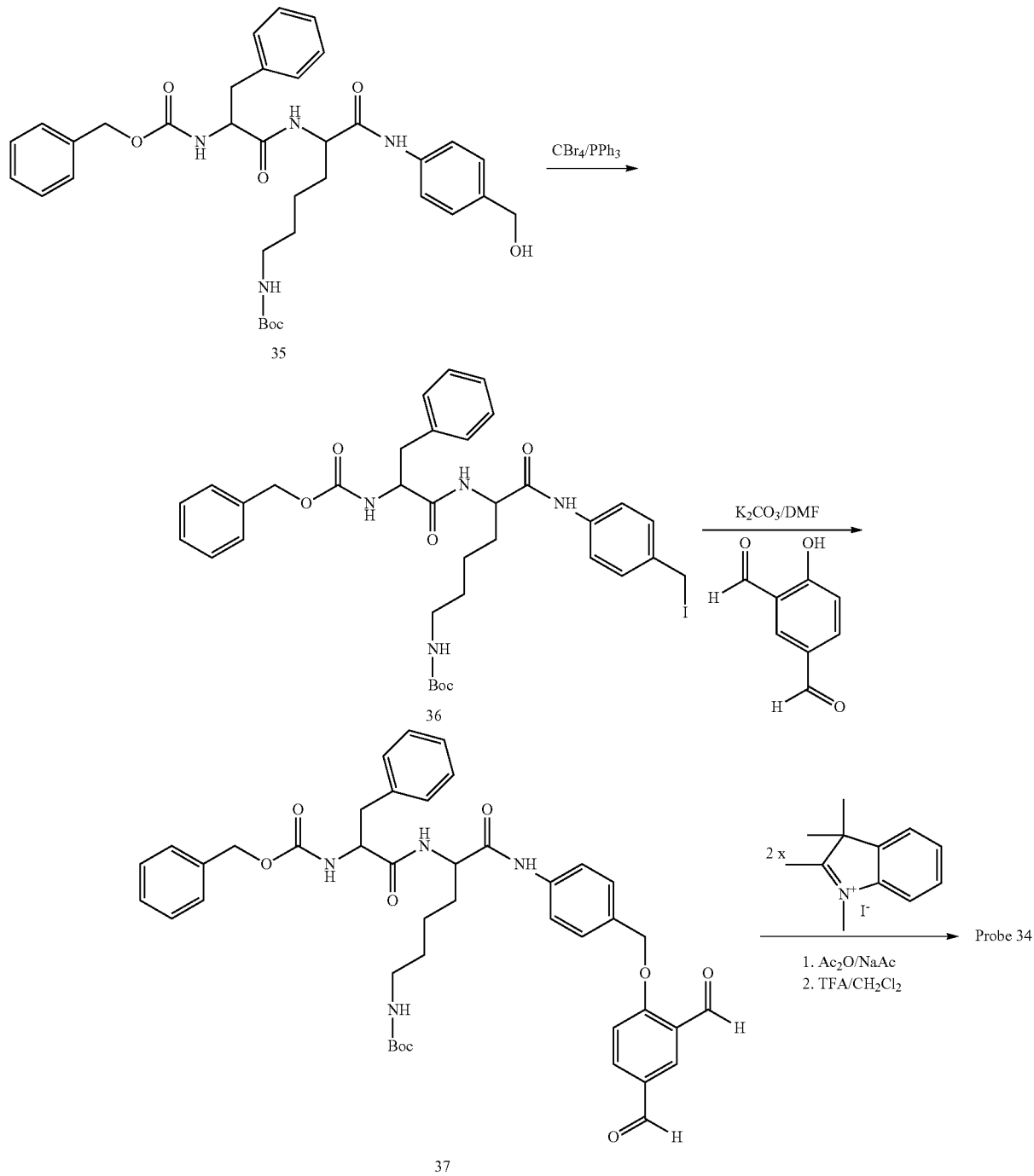

The fluorescence behavior of probe Compound 34 upon incubation with cathepsin B was studied. The data are presented in FIG. 24B.

Evaluating cathepsin B activity in vitro, while utilizing the probe, is performed as follows:

Two populations of cancerous cells are subjected to treatment with probe Compound 7 in a cell culture assay. The first cell population is grown in complete medium (RPMI supplemented with 10% fetal bovine serum) before treatment and the second cell population is grown in starvation medium (RPMI supplemented with 2% fetal bovine serum) during the 24 hours prior to treatment. Under these stress conditions, cells are known to increase the expression of proteolytic enzymes. Cell starvation is thus used to mimic the elevated expression of cathepsin B observed in cancerous tissue. Both cell populations are then incubated in the presence and absence of varying concentrations of probe Compound 7 in PBS 7.4 at 37° C., and the emitted NIR fluorescence is measured by a spectrophotometer.

The design of the cathepsin B-activated probes can be applied for imaging/detection of other enzymes that are associated with cancer like matrix-metalloproteinase and legumain. In principle, any enzyme with proteolytic or hydrolytic activity could be identified with the NIR probe methodology disclosed herein, by simply replacing the trigger moiety with a specific substrate of the appropriate enzyme.

Example 8

Prodrugs Containing Cyanine-Based Probe Moiety

In order to better evaluate the therapeutic effect of drug delivery systems, it is desired to obtain data on time and location of drug release from the delivery system in living cells and in vivo.

A coumarin-based moiety with latent fluorescence for assembly of drug-delivery systems has recently been reported (see, Wainstein et al., Chem. Commun. 2010; 46: 553-5). When the system undergoes specific activation, the drug is released and fluorescence is generated through formation of a coumarin derivative. By coupling latent fluorophore activation to the drug-release event in a prodrug drug delivery system, real-time information about the release process is obtained using non-invasive fluorescence detection techniques, as depicted in FIG. 15. When the system undergoes specific activation, the drug is released and fluorescence is generated through formation of a cyanine derivative. Consequently, the prodrug activation reports its cytotoxic activity toward cancerous cells, by emitting fluorescence.

Since a direct correlation between antitumor cell growth inhibition activity and emitted fluorescence was previously observed [Wainstein et al., 2010, supra], the amount of drug release is calculated by quantifying the emitted fluorescence. This allows prediction of a drug delivery systems' therapeutic effect and potential side effects and further serves as a reporter system for drug release and prodrug activation.

A suitable derivative of QCy7, which in addition to a triggering moiety has an appropriate functionality that can carry and release a drug molecule, is thus synthesized and is presented as Compound 41 in FIG. 26, along with the mode of action of the NIR prodrug system. Prodrug 41 is constructed base on QCy7 as linker that connects between a trigger unit (denoted as "trigger") and a drug molecule. Activation of the trigger unit results in formation of phenolate 42a that can undergo 1,4-elimination to release the drug molecule. The obtained reactive o-quinone-methide 42b rapidly reacts with a water molecule to generate phenolate 42c. The obtained quinone derivative has similar conjugation pattern to that of Cy7 and thus emits MR fluorescence. This design allows masking the NIR fluorescence of QCy7 by a specific trigger moiety, which upon its removal the drug unit is released and the NIR fluorophore is obtained.

As an example, a prodrug of Taxol (prodrug 43), activated by cathepsin B so as to release both a pluorochrome and the Taxol drug is designed, as depicted in FIG. 27.

Taxol® (paclitaxel) is an appropriate candidate as a chemotherapeutic drug that can be incorporated in prodrug 41 hereinabove since it has an available hydroxyl functional group, ready for linkage. Furthermore, Taxol is not soluble in water and its assembly with the hydrophilic skeleton of prodrug 41 assists to solubilize it in aqueous media. Based on the design presented in FIG. 26, prodrug 43 is prepared. The prodrug is constructed of the dipeptide Z-Phe-Lys attached to Taxol and sulfo-QCy7 through a short self-immolative linker. Activation of the prodrug with cathepsin B results in release of free Taxol and generation of NIR fluorescence by formation of sulfo-QCy7 (FIG. 27).

Prodrug 43 is synthesized from Compound 35 (see, Scheme 8 above), which is reacted with hydroxymethylated dialdehyde Compound 2 (see, FIG. 3A) to give the corresponding ether. The latter is reacted 4-nitrophenyl carbonate of Taxol and the obtained coupled compound is then condensed with sulfonylindolium-iodide (Compound 7) to yield prodrug 43.

The fluorescence behavior of Prodrug 43 upon incubation with cathepsin B is then studied. Evaluating cathepsin B activity in vitro, while utilizing Prodrug 43, is thereafter performed as described in Example 7 hereinabove. The NIR fluorescence emitted from the treated cells is monitored in real-time. The cytotoxicity obtained by prodrug 43 is evaluated and correlated with the emitted fluorescence. The observed signal is then calibrated to report the prodrug activation in real time.

Example 9

Cyanine-Based Probes Having Various Triggering Moieties

Three different QCy7 probes for detection and imaging of hydrogen peroxide, ubiquitous sulfhydryl, and β-galactosidase were prepared and tested.

The three QCy7-based probes are presented in FIG. 28. Probe 44, designed for detection of hydrogen peroxide, features a phenyl-boronic-ester triggering moiety as substrate of hydrogen peroxide; probe 45, designed for detection of ubiquitous sulfhydryl, exhibits a dinitro-benzene-sulfonyl triggering moiety; and probe 46, designed for detection of the enzyme β-galactosidase, exhibits β-galactose as a triggering unit. Reaction of the specific analyte/enzyme with the appropriate probe results in the release of active QCy7 fluorochrome.

All reactions requiring anhydrous conditions were performed under an Argon atmosphere. All reactions were carried out at room temperature unless stated otherwise.

Chemicals and solvents were either A.R. grade or purified by standard techniques.

Thin layer chromatography (TLC): silica gel plates Merck 60 F254: compounds were visualized by irradiation with UV light.

Flash chromatography (FC): silica gel Merck 60 (particle size 0.040-0.063 mm), eluent given in parentheses.

$^1$H-NMR spectra were measured using Bruker Avance operated at 400 MHz as mentioned. $^{13}$C-NMR spectra were measured using Bruker Avance operated at 100 MHz as mentioned. The chemical shifts are expressed in δ relative to TMS (δ=0 ppm) and coupling constants J in Hz. The spectra were recorded in CDCl$_3$ as solvent at room temperature unless stated otherwise.

Synthesis of Probe 44:

The synthesis of Probe 44 is depicted in FIG. 29A. 4-Hydroxy-isophthalaldehyde 2 is initially reacted with the phenyl-boronic-ester 5 and then condensed with two equivalents of sulfo-indolium 7 to afford the corresponding Probe 44.

Synthesis of Compound 6:

Compound 2 (175 mg, 1.16 mmol) was dissolved in 5 ml dry DMF, the solution was stirred and then cooled to 0° C. K$_2$CO$_3$ (320 mg, 2 equivalents) was added and the mixture was maintained at 0° C. for 10 minutes, to obtain a yellow mixture. Compound 5 (1.39 mmol, 2 equivalents) was added to the cooled mixture, and after 2 minutes the mixture was allowed to warm to room temperature and was stirred for 10-12 hours at room temperature. After completion, the reaction mixture was diluted with Et$_2$O (100 ml), and washed with saturated solution of NH₄Cl (100 ml). The organic layer was separated, washed with brine, dried over sodium sulfate, filtered and evaporated under reduced pressure. The crude product was purified by column chromatography on silica gel (using a gradient EtOAc/Hex eluent, starting from EtOAc/Hex 30:70 and up to EtOAc/Hex 40:10) to give Compound 6 (330 mg, 77%) as a white solid.

¹H NMR (400 MHz, CDCl₃): δ=10.55 (1H, s), 9.93 (1H, s), 8.35 (1H, d, J=2.2 Hz), 8.09 (1H, dd, J=8.6, 2.2 Hz), 7.86 (2H, d, J=8.0 Hz), 7.44 (2H, d, J=8.0 Hz), 7.17 (1H, d, J=8.7 Hz), 5.32 (2H, s), 1.34 (12H, s) ppm.

¹³C NMR (CDCl₃, 100 MHz): δ=190.81, 189.19, 165.62, 138.68, 136.31, 136.05, 132.59, 130.59, 127.21, 125.90, 114.40, 84.72, 71.74, 25.59 ppm.

MS (ES⁺): m/z calc. for C₂₁H₂₃BO₅: 366.2. found 389.2 [M+Na]⁺.

Synthesis of Probe 44:

A mixture of Compound 6 (30 mg, 0.08 mmol), NaOAc (16.4 mg, 0.2 mmol), compound 7 [Mason et al. (2005) *J. Org. Chem.* 70, 2939-49] (58 mg, 0.2 mmol) and 2 ml Ac₂O was refluxed for 30 minutes at 80° C. while monitoring the reaction by RP-HPLC (grad. 10-90% ACN in 0.1% TFA in water, 20 minutes; product appears as pinacol boronic ester and as boronic acid). After completion, the reaction mixture was concentrated by evaporation under reduced pressure. The crude product was dissolved in 3 ml dichloromethane and a minimal amount of methanol, and purified by column chromatography on silica gel (upon mixing the silica with methanol, removing the methanol and washing the silica with dichloromethane) using 100 ml dichloromethane for washing the product, and then a gradient of 1:9 to 1:1 MeOH:DCM, as eluent, to give Probe 44 (69 mg, 94%) as a brown solid.

¹H NMR (CD₃OD, 400 MHz): δ=9.21 (1H, s), 8.80 (1H, d, J=16.4 Hz), 8.59 (1H, d, J=16.3 Hz), 8.42 (2H, d, J=9.08 Hz), 8.23 (1H, d, J=16.5 Hz), 8.07 (1H, d, J=16.2 Hz), 7.95-7.92 (2H, m), 7.86 (2H, d, J=8.0 Hz), 7.80-7.76 (2H, m), 7.67-7.63 (4H, m), 7.60 (2H, d, J=7.9 Hz), 7.49 (1H, d, J=8.8 Hz), 5.46 (2H, s), 5.00 (4H, t, J=6.3 Hz), 3.10-3.06 (4H, m), 2.44 (4H, m), 1.98 (6H, s), 1.80 (6H, s), 1.37 (12H, s) ppm.

¹³C NMR (DMSO-d6, 100 MHz): δ=182.41, 182.18, 162.02, 153.57, 153.35, 146.74, 144.44, 144.16, 141.25, 138.16, 137.77, 134.79, 133.37, 130.06, 129.66, 129.43, 128.74, 126.97, 124.35, 123.43, 123.39, 115.78, 115.50, 115.24, 114.91, 114.80, 112.76, 112.53, 71.37, 52.70, 52.47, 47.56, 46.20, 45.85, 26.50, 26.50, 26.68, 25.10 ppm.

MS (ES⁺): m/z calc. for C₄₉H₅₇BN₂O₉S₂: 892.3. found 915.6 [M+Na]⁺.

HPLC grad. 10-90% ACN in water 20 minutes: RT—11.9 minutes (boronic acid) and 15.9 minutes (boronic ester), λ=425 nm.

Synthesis of Probe 45:

The synthesis of Probe 45 is depicted in FIG. 29B. 4-Hydroxy-isophthalaldehyde 2 is initially reacted with dinitrobenzene-sulfone-amide 47 and then condensed with two equivalents of sulfo-indolium 7 to afford the corresponding Probe 45. Compound 47 was prepared as depicted in Scheme 9.

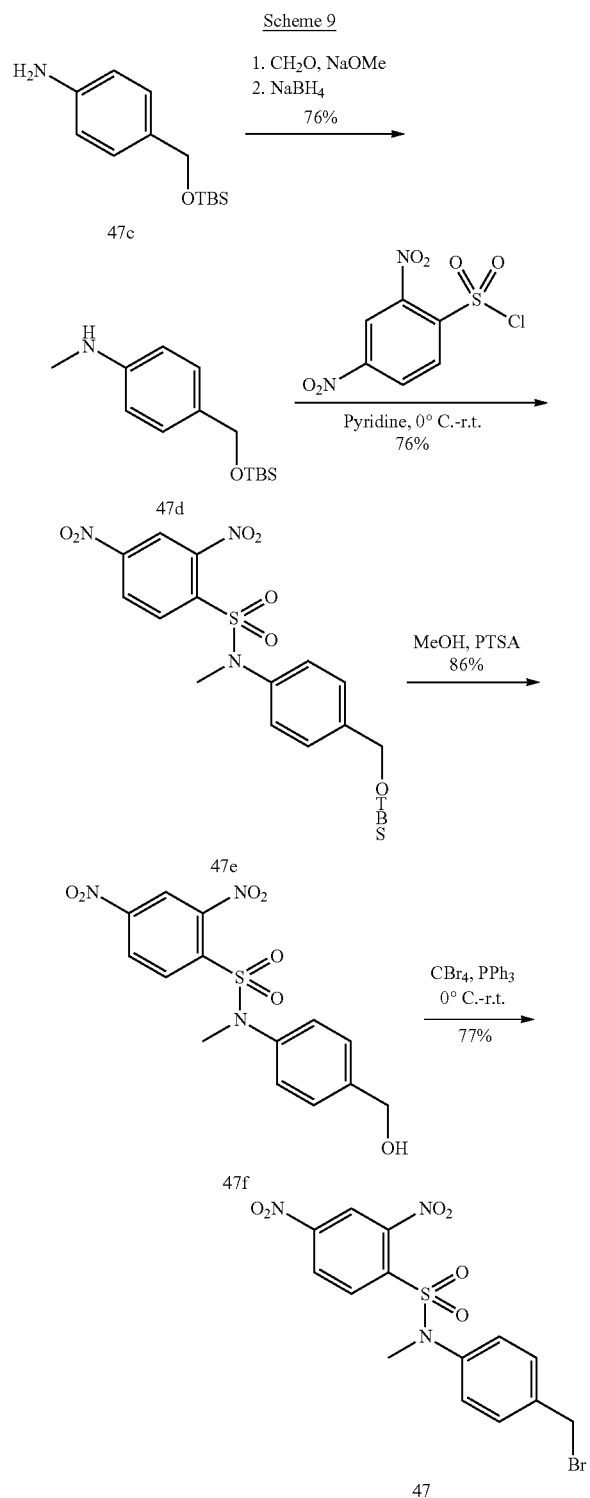

Synthesis of Compound 47:

Compound 47c (500 mg, 1 equivalent, [Bernardo, P. H. et al. *J. Med. Chem.*, 2008, 51, 6699-6710]), was dissolved in MeOH (100 ml). NaOMe (580 mg, 5 equivalents) and formaldehyde (35% in H₂O, 840 μL, 5 equivalents) were added, and the solution was heated to reflux. After 2 hours in reflux, the solution was cooled to 0° C., and NaBH₄ (400 mg, 5 equivalents) was added slowly. The solution was heated to reflux for 1 hour, and was then poured into ice water, and extracted with EtOAc. The organic layer was dried over sodium sulfate and the solvent was removed under reduced pressure. The crude product was purified by column chromatography on silica gel (EtOAc/Hex 20:80) to afford compound 47d (400 mg, 76%).

$^1$H NMR (400 MHz, CDCl$_3$): δ=7.19 (2H, d, J=8.4 Hz), 6.62 (2H, d, J=8.4), 4.67 (2H, s), 2.84 (3H, s), 0.97 (9H, s), 0.12 (6H, s) ppm.

$^{13}$C NMR (100 MHz, CDCl$_3$): δ=149.27, 130.87, 128.49, 113.0, 65.88, 31.63, 26.8, 19.22, −4.3 ppm.

MS (ES$^+$): m/z calc. for C$_{14}$H$_{25}$NOSi: 251.17. found: 252.3 [M+H]$^+$.

Compound 47d (400 mg, 1 equivalent) was then dissolved in pyridine, and the solution was cooled to 0° C. 2,4-Dinitrobenzenesulfonyl chloride (467 mg, 1.1 equivalents) was added, and the reaction mixture was stirred at 0° C. for 30 minutes, before warming it to room temperature. The reaction was monitored by TLC (EtOAc/Hex 20:80). Upon completion, the reaction mixture was diluted with EtOAc and washed twice with a solution of 1M HCl. The organic layer was dried over sodium sulfate and the solvent was removed under reduced pressure. The crude product was purified by column chromatography on silica gel (EtOAc/Hex 20:80) to afford compound 47e (584 mg, 76%).

$^1$H NMR (400 MHz, CDCl$_3$): δ=8.42 (1H, d, J=2 Hz), 8.3 (1H, dd, J=2, 8.8 Hz), 7.68 (1H, d, J=8.8 Hz), 7.33 (2H, d, J=8.4 Hz), 7.18 (2H, d, J=8.4 Hz), 4.74 (2H, s), 3.39 (3H, s), 0.93 (9H, s), 0.1 (6H, s) ppm.

$^{13}$C NMR (100 MHz, CDCl$_3$): δ=150.43, 148.95, 143.02, 138.84, 137.28, 134.13, 128.13, 127.79, 126.24, 120.09, 64.92, 40.56, 26.63, 19.09, −4.56 ppm.

MS (ES$^+$): m/z calc. for C$_{20}$H$_{27}$N$_3$O$_7$SSi: 481.13. found: 504.3 [M+Na]$^+$.

Compound 47e (370 mg) was then dissolved in 3 mL MeOH. A catalytic amount of PTSA was added to the suspension, and the reaction mixture was stirred at room temperature and monitored by TLC (EtOAc/Hex 40:60). After completion of the reaction, the solvent was removed under reduced pressure. The crude product was purified by column chromatography on silica gel (EtOAc/Hex 70:30) to give compound 47f (243 mg, 86%) as yellow oil.

$^1$H NMR (400 MHz, CDCl$_3$): δ=8.57 (1H, d, J=2.2 Hz), 8.4 (1H, dd, J=2.2, 8.7 Hz), 7.83 (1H, d, J=8.7 Hz), 7.34 (2H, d, J=8.5 Hz), 7.2 (2H, d, J=8.5 Hz), 4.57 (2H, s), 3.35 (3H, s) ppm.

$^{13}$C NMR (100 MHz, CDCl$_3$): δ=151.05, 148.91, 143.31, 139.3, 136.18, 133.43, 128.21, 128.08, 127.01, 120.41, 63.72, 40.0 ppm.

MS (ES$^+$): m/z calc. for C$_{14}$H$_{13}$N$_3$O$_7$S: 367.05. found: 390.2 [M+Na]$^+$.

Compound 47f (400 mg, 1 equivalent) was dissolved in THF, and the solution was cooled to 0° C. PPh$_3$ (655 mg, 2.3 equivalents) was added and after 3 minutes CBr$_4$ (830 mg, 2.3 equivalents) was added. The reaction mixture was stirred at room temperature and the progress was monitored by TLC (EtOAc/Hex 30:70). After completion, the reaction mixture was evaporated under reduced pressure. The crude product was purified by column chromatography on silica gel (EtOAc/Hex 40:60) to afford compound 47 (330 mg, 77%) as yellow solid.

$^1$H NMR (400 MHz, CDCl$_3$): δ=8.43 (1H, d, J=2.2 Hz), 8.32 (1H, dd, J=2.2, 8.6 Hz), 7.74 (1H, d, J=8.6 Hz), 7.39 (2H, d, J=8.5 Hz), 7.25 (2H, d, J=8.4 Hz), 4.46 (2H, s), 3.41 (3H, s) ppm.

$^{13}$C NMR (100 MHz, CDCl$_3$): δ=150.53, 149.07, 140.21, 139.15, 137.33, 134.09, 131.07, 128.51, 126.23, 120.16, 40.46, 32.68 ppm.

MS (ES$^+$): m/z calc. for C$_{14}$H$_{12}$BrN$_3$O$_6$S: 430.96. found: 454.0 [M+Na]$^+$.

Synthesis of Compound 48:

Compound 2 (115 mg, 0.76 mmol) was dissolved in 3 ml dry DMF, the solution was stirred and then cooled to 0° C. K$_2$CO$_3$ (127 mg, 2 equivalents, 0.92 mmol) was added and the mixture was maintained at 0° C. for 10 minutes, to obtained a yellow mixture. Compound 47 (330 mg, 0.76 mmol, prepared as described hereinabove) was added to the cooled mixture, and after 2 minutes the mixture was allowed to warm to room temperature and was stirred for 10-12 hours at room temperature. After completion, the reaction mixture was diluted with Et$_2$O (100 ml), and washed with saturated solution of NH$_4$Cl (100 ml). The organic layer was separated, washed with brine, dried over sodium sulfate, filtered and evaporated under reduced pressure. The crude product was purified by column chromatography on silica gel (using a gradient EtOAc/Hex eluent, starting from EtOAc/Hex 30:70 and up to EtOAc/Hex 40:10) to give Compound 48 (240 mg, 63%) as yellow oil.

$^1$H NMR (400 MHz, CDCl$_3$): δ=10.51 (1H, s), 9.96 (1H, s), 8.44 (1H, d, J=2 Hz), 8.35 (1H, d, J=2 Hz), 8.34 (1H, dd, J=2.1, 8.7 Hz), 8.13 (1H, dd, J=2.1, 8.7 Hz), 7.8 (1H, d, J=8.6 Hz), 7.47 (2H, d, J=8.3 Hz), 7.31 (2H, d, J=8.3 Hz), 7.19 (1H, d, J=8.6 Hz), 5.29 (2H, s), 3.44 (3H, s) ppm.

$^{13}$C NMR (100 MHz, CDCl$_3$): 190.69, 188.95, 150.59, 140.61, 137.37, 136.4, 133.98, 132.9, 130.9, 129.23, 128.68, 126.25, 125.97, 120.22, 114.21, 70.88, 30.39 ppm.

MS (ES$^+$): m/z calc. for C$_{22}$H$_{17}$N$_3$O$_9$S: 499.07. found: 522.3 [M+Na]$^+$.

Synthesis of Probe 45:

A mixture of Compound 48 (50 mg, 0.1 mmol), NaOAc (17 mg, 0.21 mmol), compound 7 [Mason et al. (2005) *J. Org. Chem.* 70, 2939-49] (59 mg, 0.21 mmol) and 1 ml Ac$_2$O was refluxed for approx. 30 minutes at 80° C. while monitoring the reaction by RP-HPLC (grad. 10-90% ACN in 0.1% TFA in water, 20 minutes). After completion, the reaction mixture was concentrated by evaporation under reduced pressure. The crude product was dissolved in 3 ml dichloromethane and a minimal amount of methanol, and purified by silica gel column chromatography (upon mixing the silica with methanol, removing the methanol and washing the silica with dichloromethane) using 100 ml dichloromethane for washing the product, and then a gradient of 1:9 to 3:7 MeOH:DCM, as eluent, to give Probe 45 (96 mg, 93%) as an orange solid.

$^1$H NMR (400 MHz, MeOD): δ=9.19 (1H, d, J=1.8 Hz), 8.77 (1H, d, J=16.4 Hz), 8.69 (1H, d, J=2.2 Hz), 8.58 (1H, d, J=16.2 Hz), 8.51 (1H, dd, J=2.2, 8.7 Hz), 8.39 (1H, dd, J=1.8, 8.8 Hz), 8.2 (1H, d, J=16.4 Hz), 8.07 (1H, d, J=16.2 Hz), 7.98 (1H, d, J=8.6 Hz), 7.95-7.91 (2H, m), 7.78-7.75 (2H, m), 7.66-7.6 (6H, m), 7.47 (1H, d, J=8.8 Hz), 7.39 (2H, d, J=8.4 Hz), 5.47 (2H, s), 5.02-4.95 (4H, m), 3.44 (3H, s), 3.1-3.03 (4H, m), 2.44 (4H, m), 1.92 (6H, s), 1.8 (6H, s) ppm.

$^{13}$C NMR (100 MHz, MeOD): δ=144.74, 143.49, 141.53, 140.55, 133.41, 132.87, 129.54, 128.3, 128.14, 126.54, 123.5, 122.97, 122.16, 121.63, 120.38, 115.56, 109.58, 109.05, 93.88, 63.8, 53.27, 41.85, 31.59, 30.07, 22.93 ppm.

MS (ES$^+$): m/z calc. for C$_{50}$H$_{51}$N$_5$O$_{13}$S$_3$: 1025.26. found: 1048.5 [M+Na]$^+$.

HPLC grad. 10-90% ACN in water 20 minutes: R$_T$=15.7 minutes, λ=425 nm.

Synthesis of Probe 46:

The synthesis of Probe 46 is depicted in FIG. 29C. 4-Hydroxy-isophthalaldehyde 2 is initially reacted with β-galactose derivative 49 to give ether 50, which is condensed with two equivalents of sulfo-indolium 7 to give intermediate 51, which is then deprotected of the acetate groups to afford Probe 46. The β-galactose derivative 49 was prepared as depicted in Scheme 10.

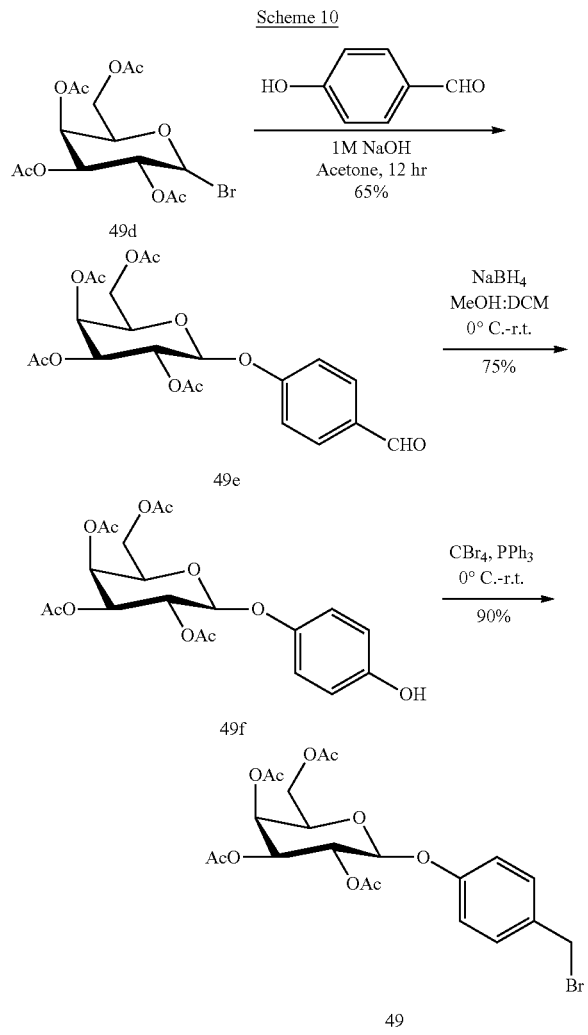

Synthesis of β-galactose derivative 49:

4-hydroxybenzaldehyde (772 mg, 1 equivalent) dissolved in 1M NaOH solution (6 ml), was added dropwise to a solution of Compound 49d (2.6 grams, 1 equivalent [Orth, R.; Pitscheider, M.; Sieber, S. A.; SYNTHESIS, 2010, 13, 2201-2206]) in acetone (11 ml). The reaction mixture was stirred for 12 hours at room temperature was monitored by TLC (EtOAc/Hex 50:50). Upon completion, the reaction mixture was diluted with DCM and washed with water. The organic layer was dried over sodium sulfate and the solvent was removed under reduced pressure. The crude product was purified by column chromatography on silica gel (EtOAc/Hex 50:50) to afford compound 49e (1.72 grams, 60%).

$^1$H NMR (400 MHz, CDCl$_3$): δ=9.86 (1H, s), 7.81 (2H, d, J=8.6 Hz), 7.08 (2H, d, J=8.6 Hz), 5.49-5.42 (2H, m), 5.17 (1H, d, J=7.9 Hz), 5.12 (1H, dd, J=10.4, 3.3 Hz), 4.18-4.02 (3H, m), 2.14 (3H, s), 2.01 (6H, s), 1.97 (3H, s) ppm.

$^{13}$C NMR (100 MHz, CDCl$_3$): δ=191.51, 171.06, 170.92, 170.8, 170.05, 162.01, 132.52, 117.44, 99.22, 72.0, 71.37, 69.13, 67.51, 62.08, 21.31 ppm.

MS (ES$^+$): m/z calc. for C$_{21}$H$_{24}$O$_{11}$: 452.13. found: 475.3 [M+Na]$^+$.

Compound 49e (1.65 grams, 1 equivalent), was dissolved in MeOH, and the solution was cooled to 0° C. NaBH$_4$ (267 mg, 2 equivalents) was added slowly. The reaction was monitored by TLC (EtOAc/Hex 60:40). Upon completion, the reaction mixture was diluted with EtOAc and washed with a saturated NH$_4$Cl solution, followed by Brine. The organic layer was dried over sodium sulfate and the solvent was removed under reduced pressure. The crude product was purified by column chromatography on silica gel (EtOAc/Hex 75:25) to afford compound 49f (800 mg, 50%).

$^1$H NMR (400 MHz, CDCl$_3$): δ=7.25 (2H, d, J=8.6 Hz), 6.95 (2H, d, J=8.6 Hz), 5.45-5.4 (2H, m), 5.08 (1H, dd, J=10.4, 3.3 Hz), 5.01 (1H, d, J=7.9 Hz), 4.57 (2H, s), 4.19-4.01 (3H, m), 2.13 (3H, s), 2.01 (3H, s), 2.0 (3H, s), 1.96 (3H, s) ppm.

$^{13}$C NMR (100 MHz, CDCl$_3$): δ=171.15, 171.04, 170.89, 170.18, 157.07, 136.77, 129.12, 117.67, 100.38, 71.68, 71.53, 69.4, 67.64, 65.2, 21.33 ppm.

MS (ES$^+$): m/z calc. for C$_{21}$H$_{26}$O$_{11}$: 454.15. found: 477.3 [M+Na]$^+$.

Compound 49f (688 mg, 1 equivalent) was dissolved in THF, and the solution was cooled to 0° C. PPh$_3$ (913 mg, 2.3 equivalents) was added and after 3 minutes CBr$_4$ (1.155 grams, 2.3 equivalents) was added. The reaction mixture was stirred for 10 minutes at room temperature and the progress was monitored by TLC (EtOAc/Hex 40: 60). After completion, the reaction mixture was evaporated under reduced pressure. The crude product was purified by column chromatography on silica gel (EtOAc/Hex 50:50) to afford compound 49 (701 mg, 90%).

$^1$H NMR (400 MHz, CDCl$_3$): δ=7.33 (2H, d, J=8.6 Hz), 6.96 (2H, d, J=8.6 Hz), 5.49-5.44 (2H, m), 5.11 (1H, dd, J=10.4, 3.3 Hz), 5.04 (1H, d, J=7.9 Hz), 4.47 (2H, s), 4.23-4.04 (3H, m), 2.17 (3H, s), 2.05 (6H, s), 2.0 (3H, s) ppm.

$^{13}$C NMR (100 MHz, CDCl$_3$): δ=171.06, 170.95, 170.83, 170.09, 157.55, 133.48, 131.18, 117.85, 100.15, 71.81, 71.5, 69.29, 67.57, 62.08, 33.84, 21.33 ppm.

MS (ES$^+$): m/z calc. for C$_{21}$H$_{26}$O$_{11}$: 516.06. found: 541.2 [M+Na]$^+$.

Synthesis of Compound 50:

Compound 2 (190.3 mg, 1.26 mmol) was dissolved in 5 ml dry DMF, the solution was stirred and then cooled to 0° C. K$_2$CO$_3$ (210 mg, 2 equivalents, 1.52 mmol) was added and the mixture was maintained at 0° C. for 10 minutes, to obtained a yellow mixture. Compound 49 (656 mg, 1.26 mmol) was added to the cooled mixture, and after 2 minutes the mixture was allowed to warm to room temperature and was stirred for 10-12 hours at room temperature. After completion, the reaction mixture was diluted with Et$_2$O (100 ml), and washed with saturated solution of NH$_4$Cl (100 ml). The organic layer was separated, washed with brine (100 ML), dried over sodium sulfate, filtered and evaporated under reduced pressure. The crude product was purified by column chromatography on silica gel (using a gradient EtOAc/Hex eluent, starting from EtOAc/Hex 30:70 and up to EtOAc/Hex 90:10) to give Compound 50 (596 mg, 88%) as yellow oil.

$^1$H NMR (400 MHz, CDCl$_3$): δ=10.5 (1H, s), 9.94 (1H, s), 8.34 (1H, d, J=2 Hz), 8.11 (1H, dd, J=8.8, 2 Hz), 7.39 (2H, d, J=8.6 Hz), 7.21 (2H, d, J=8.7 Hz), 7.06 (2H, d, J=8.6 Hz), 5.51-5.45 (2H, m), 5.23 (2H, s), 5.13 (1H, dd, J=10.4, 3.4 Hz), 5.08 (1H, d, J=7.9 Hz), 4.25-4.05 (3H, m), 2.18 (3H, s), 2.06 (3H, s), 2.05 (3H, s), 2.01 (3H, s) ppm.

$^{13}$C NMR (100 MHz, CDCl$_3$): δ=190.8, 189.15, 171.04, 170.83, 170.87, 170.13, 165.59, 157.84, 136.3, 132.7, 130.6, 130.53, 129.88, 125.87, 117.99, 114.28, 100.19, 71.82, 71.49, 71.38, 69.31, 67.53, 62.01, 21.38 ppm.

MS (ES$^+$): m/z calc. for $C_{29}H_{30}O_{13}$: 586.17. found: 609.3 [M+Na]$^+$.

Synthesis of Probe 46:

A mixture of Compound 50 (50 mg, 0.09 mmol), NaOAc (16 mg, 0.19 mmol), compound 7 [Mason et al. (2005) J. Org. Chem. 70, 2939-49] (55 mg, 0.19 mmol) and 1 ml $Ac_2O$ was refluxed for approx. 30 minutes at 80° C. while monitoring the reaction by RP-HPLC (grad. 10-90% ACN in 0.1% TFA in water, 20 minutes). After completion, the reaction mixture was concentrated by evaporation under reduced pressure to yield Compound 51, which is used without purification. Compound 51 was dissolved in 5 ml MeOH, potassium carbonate (25 mg, 0.18 mmol) was added, and the mixture was stirred, while monitoring the reaction by RP-HPLC (grad. 10-90% ACN in 0.1% TFA in water, 20 minutes). After completion, the solvent was removed under reduced pressure and the crude product was purified by silica gel column chromatography (upon mixing the silica with methanol, removing the methanol and washing the silica with dichloromethane) using 100 ml hexanes and 100 ml dichloromethane for washing the product, and then a gradient of 1:9 to 9:1 MeOH: DCM, as eluent, to give Probe 46 (80 mg, 94%) as an orange solid.

$^1$H NMR (400 MHz, MeOD): δ=9.16 (1H, s), 8.68 (1H, d, J=16.4 Hz), 8.55 (1H, d J=16.2 Hz), 8.35 (1H, dd, J=8.6, 2.2 Hz), 8.13 (1H, d, J=16.4 Hz), 8.04 (1H, d, J=16.2 Hz), 7.93-7.49 (11H, m), 7.23 (2H, d, J=8.6 Hz), 5.37 (2H, s), 4.98-4.95 (4H, m), 3.97-3.56 (7H, m), 3.14-2.86 (4H, m), 2.52-2.22 (4H, m), 2.14 (6H, s), 1.91 (6H, s) ppm.

$^{13}$C NMR (100 MHz, MeOD): δ=183.47, 183.22, 163.58, 158.98, 154.54, 148.92, 144.70, 144.63, 141.44, 138.98, 133.61, 130.53, 130.36, 130.27, 130.02, 128.96, 128.38, 124.81, 123.44, 117.43, 115.69, 115.40, 114.86, 114.50, 102.05, 76.42, 74.19, 72.11, 71.64, 69.60, 61.87, 53.26, 46.35, 45.99, 30.04, 26.46, 26.22, 24.88, 23.56, 22.09 ppm.

MS (ESI): m/z calc. for $C_{49}H_{56}N_2O_{13}S_2$: 945.1. found: 967.5 [M+Na]$^+$.

HPLC grad. 10-90% ACN in water 20 mM: RT—10.6 mM, λ=425 nm.

NIR Fluorescence Assays:

The turn-ON response of Probes 44, 45, and 46 upon incubation with their corresponding analytes was evaluated in vitro and in vivo.

Probes 44, 45, and 46 were incubated with hydrogen peroxide, cysteine, and β-galactosidase, respectively, in PBS, pH 7.4 and NIR-fluorescent emission was recorded, using the following procedures:

For Probe 44:

A 10 mM stock solution of Probe 44 in DMSO (MW 892 g/mol) was prepared. A 10 mM stock solution of $H_2O_2$ was prepared by adding 1.1 μl of 30% (wt/vol) $H_2O_2$ into 998.9 μl of water.

1 μl of Probe 44 (10 mM stock solution) and 5 μl of $H_2O_2$ (10 mM stock solution) were added into 94 μl of 0.1 M PBS buffer, pH 7.4 (Probe 44 final concentration 100 μM, and $H_2O_2$ final concentration 500 μM). A control solution containing 1 μl of Probe 44 (10 mM stock solution from step 22) and 99 μl of 0.1 M PBS, pH 7.4, without $H_2O_2$ was also prepared.

For Probe 45:

A 10 mM stock solution of Probe 45 in DMSO (MW 1026.16 g/mol) and a 10 mM stock solution of cysteine were prepared.

1 μl of Probe 45 (10 mM stock solution) and 1 μl of cysteine (10 mM stock solution) were added into 98 μl of 0.1 M PBS buffer, pH 7.4 (Probe 45 final concentration 100 μM). A control solution containing 1 μl of Probe 45 (10 mM stock solution from step 22) and 99 μl of 0.1 M PBS, pH 7.4, without cysteine, was also prepared.

For Probe 46:

A 10 mM stock solution of Probe 46 in DMSO (MW 945 g/mol) was prepared. A 10 mM stock solution of the beta-galactosidase enzyme was prepared by adding 1 mg of the enzyme into 1 ml of 0.1 M PBS, pH 7.4, yielding approximately 115 enzyme units per 1 ml.

1 μl of Probe 46 (10 mM stock solution) and 5 μl of the enzyme stock solution were added into 94 μl of 0.1 M PBS buffer, pH 7.4 (Probe 46 final concentration 100 μM; enzyme final concentration 0.57 units per 100 μl). A control solution containing 1 μl of Probe 46 (10 mM stock solution) and 99 μl of 0.1 M PBS, pH 7.4, without the enzyme, was also prepared.

Immediately upon preparation, the fluorescence intensity of the samples was recorded using a fluorometric plate reader, operated at excitation wavelength of 590 nm, and emission of 720 nm.

FIGS. 30A-C present the obtained data and demonstrate that the NIR-fluorescent emission of each probe upon reaction with its corresponding analyte gradually increased over time. No fluorescence increase was observed in the absence of analyte (data not shown).

FIGS. 31A-B, 32A-B and 33A-B presents data obtained with various concentrations of the analytes and show the probe's sensitivity.

To demonstrate the in vivo turn-ON imaging option, the probes were then injected subcutaneously into mice. Each mouse was injected with the probe and a probe with its corresponding analyte immediately following addition and imaged over time using intravital Cri Maestro™ imaging system. The obtained data is presented in FIGS. 34A-C and show good in vivo compatibility with high signal-to-background ratio. Probes injected with their corresponding analyte exhibited an increased NIR-fluorescent signal in mice. In contrast, when probes injected without the analyte, no fluorescence increase was observed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A fluorogenic compound comprising at least two acceptor-containing moieties and a donor-containing moiety arranged such that:
   (i) said at least two acceptor-containing moieties and said donor-containing moiety form a conjugated π-electron system devoid of resonating electrons, such that the compound is incapable of emitting NIR infrared light; and
   (ii) upon a chemical event, said donor-containing moiety rearranges so as to transfer π-electrons to one of said acceptor-containing moieties and, as a result, said acceptor-containing moiety becomes a donor-containing moiety to at least one another acceptor-containing moiety, to thereby enable emission of near infrared light, the fluorogenic compound having the general Formula I:

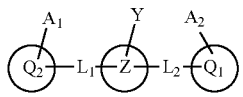

Formula I wherein:
$Q_1$ and $Q_2$ are each independently an acceptor-containing moiety, and $A_1$ and $A_2$ are each an acceptor group in said acceptor-containing moieties, said acceptor group being an ammonium ion and said acceptor-containing moiety being independently a substituted or unsubstituted, positively charged, nitrogen-containing heterocyclic moiety represented by

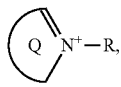

wherein R is hydrogen, alkyl and cycloalkyl, at least one of said $Q_1$ and $Q_2$ being an ammonium form of an indolenine or ammonium form of a pyridine;

Z and Y form said donor-containing moiety, said donor-containing moiety comprising an aryl substituted by at least one electron-donating group, and is such that upon said chemical event, it rearranges by undergoing a 1,4-quinonemethidine-like rearrangement; and;

$L_1$ and $L_2$ are each independently a linking moiety or absent, said linking moiety comprising a carbomethine-containing chain of at least one —CR'=CR"—moiety, whereine R' and R" are each independently hydrogen, alkyl or cycloallkyl, or alternatively, R' and R" form toegther an aryl, wherein said donor-containing moiety forms a part of, or is attached to, said carbomethine-containing chain and wherein each of $L_1$ and $L_2$ is such that said $Q_1$ and $Q_2$ acceptor-containing moieties and said Z-Y donor containing moiety form said conjugated-π-electron system.

2. The fluorogenic compound of claim 1, having the general Formula IIIA:

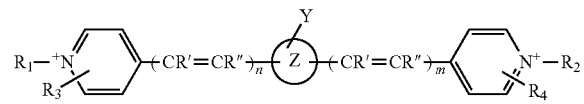

Formula IIIA wherein:
$R_1$ and $R_2$ are each independently selected from the group consisting of hydrogen, alkyl, cycloalkyl and aryl, heteroalicyclic, heteroaryl;

n and m are each independently an integer of from 0 to 4;

$R_3$ and $R_4$ are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide;

R' and R" are each independently hydrogen, alkyl or cycloalkyl, or, alternatively, R' and R" form together an aryl; and Z and Y form together said donor-containing moiety.

3. The fluorogenic compound of claim 1, having the general formula IIIB:

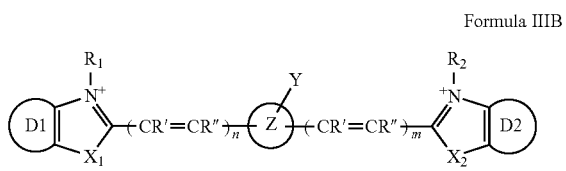

Formula IIIB wherein:
$D_1$ and $D_2$ are each independently substituted or unsubstituted aryl; and $X_1$ and $X_2$ are each independently selected from the group consisting of $CR_3R_4$, $NR_3$, and S, at least one of $X_1$ and $X_2$ being $CR_3R_4$, wherein $R_3$ and $R_4$ are each independently selected from the group consisting of hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, and a saccharide;

n and m are each independently an integer of from 0 to 4;

R' and R" are each independently hydrogen, alkyl or cycloalkyl, or, alternatively, R' and R" form together an aryl; and Z and Y form together said donor-containing moiety.

4. The fluorogenic compound of claim 1, selected from

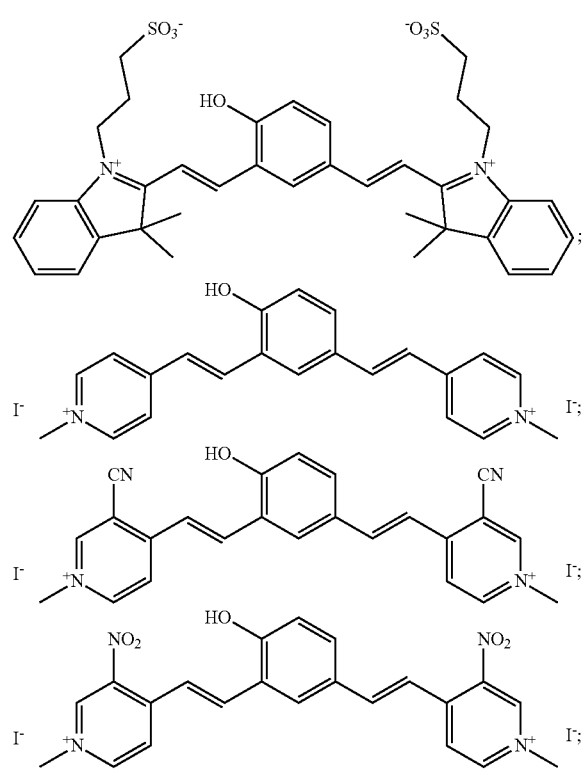

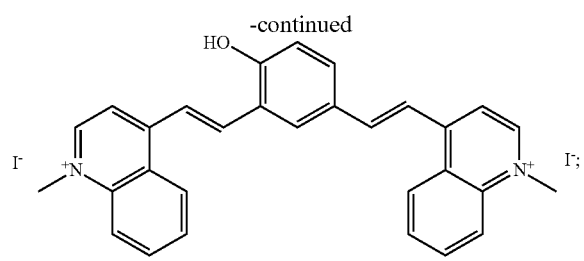
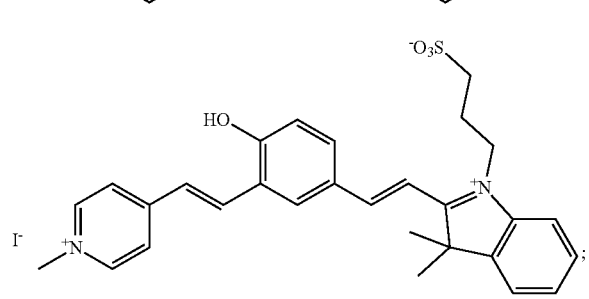
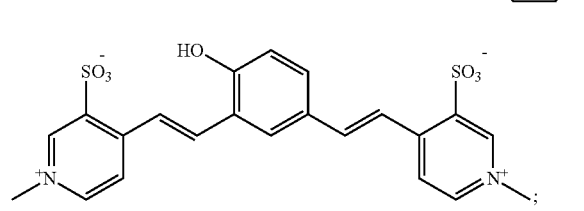
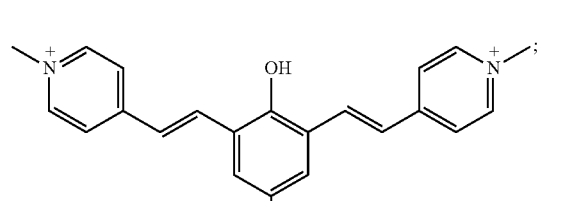
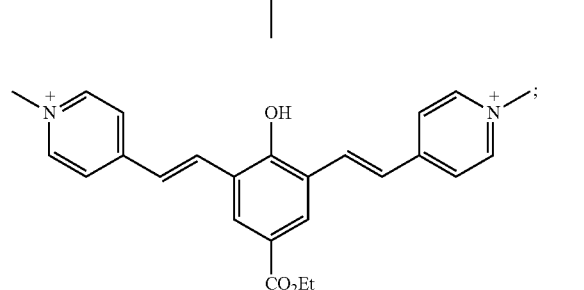
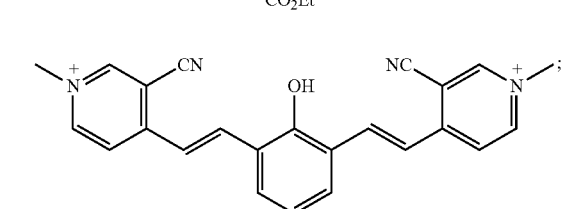
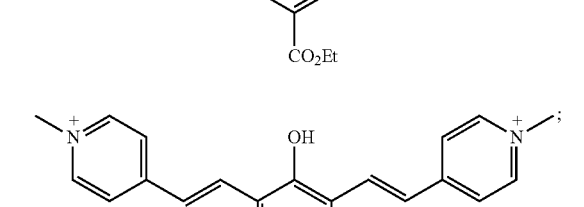
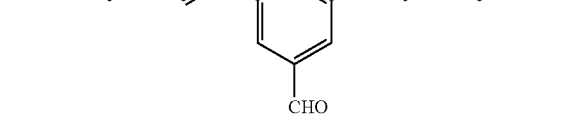

-continued

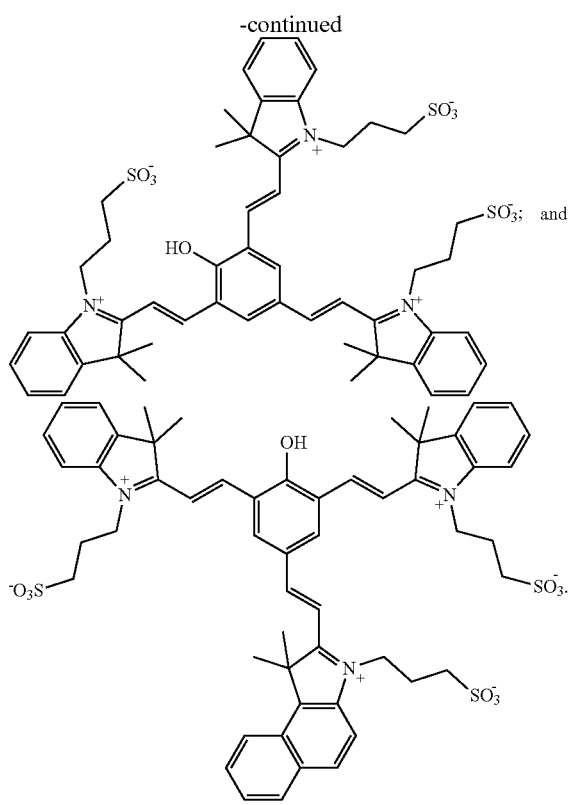

5. The fluorogenic compound of claim 1, wherein said chemical event is generated by an analyte.

6. The fluorogenic compound of claim 1, wherein said chemical event comprises cleavage in said donor-containing moiety.

7. The fluorogenic compound of claim 1, wherein said donor-containing moiety comprises a trigger unit, and wherein said chemical event comprises cleavage of said trigger unit.

8. The fluorogenic compound of claim 7, wherein said cleavage of said trigger unit is effected in the presence of an analyte.

9. The compound of claim 5, wherein said analyte is associated with a medical condition.

10. The compound of claim 9, wherein said analyte is an enzyme overexpressed in organs or tissues afflicted by said medical condition.

11. The compound of claim 9, wherein said analyte is a substance that is produced in organs or tissues in response to said medical condition.

12. The fluorogenic compound of claim 1, further comprising a therapeutically active agent being attached to said donor-containing moiety.

13. The fluorogenic compound of claim 12, wherein said therapeutically active agent is attached to said donor-containing moiety such that upon said chemical event, said therapeutically active agent is released.

14. The fluorogenic compound of claim 1, wherein Z and Y are such that said chemical event comprises cleavage of said Y.

15. The fluorogenic compound of claim 1, comprising acceptor-containing moieties and being such that the first, second and third acceptor-containing moieties and said donor-containing moiety form said conjugated π-electrons system devoid of resonating electrons.

16. A method of determining a presence and/or level of an analyte in a sample, the method comprising contacting the sample with the fluorogenic compound of claim 5; and collecting a light emitted from said sample, wherein a presence and/or level of said light is indicative of the presence and/or level of said analyte.

17. The method of claim 16, wherein said light has a wavelength within a near infrared range.

18. The method of claim 16, wherein said analyte is associated with a medical condition, and wherein determining a presence and/or level of said analyte is being for determining a presence or progression of said medical condition.

19. The method of claim 18, wherein said analyte is an enzyme overexpressed in organs or tissues afflicted by said medical condition.

20. The method of claim 19, wherein said analyte is produced in response to said medical condition.

21. A method of imaging a sample, the method comprising contacting the sample with the fluorogenic compound of claim 1, and collecting a light emitted from said sample.

22. The method of claim 21, wherein said light has a wavelength within a near infrared range.

23. A pharmaceutical composition comprising the fluorogenic compound of claim 1 and a pharmaceutically acceptable carrier.

24. The pharmaceutical composition of claim 23, wherein said chemical event is generated by an analyte and wherein the composition is identified for use in determining a presence and/or level of said analyte in a sample.

* * * * *